(12) United States Patent
Baltes et al.

(10) Patent No.: US 11,312,972 B2
(45) Date of Patent: Apr. 26, 2022

(54) METHODS FOR ALTERING AMINO ACID CONTENT IN PLANTS THROUGH FRAMESHIFT MUTATIONS

(71) Applicant: CELLECTIS, Paris (FR)

(72) Inventors: Nicholas Baltes, Maple Grove, MN (US); Song Luo, Chicago, IL (US)

(73) Assignee: Cellectis, Paris (FR)

( * ) Notice: Subject to any disclaimer, the term of this patent is extended or adjusted under 35 U.S.C. 154(b) by 0 days.

(21) Appl. No.: 16/461,553

(22) PCT Filed: Nov. 16, 2017

(86) PCT No.: PCT/IB2017/057190
§ 371 (c)(1),
(2) Date: May 16, 2019

(87) PCT Pub. No.: WO2018/092072
PCT Pub. Date: May 24, 2018

(65) Prior Publication Data
US 2019/0264220 A1    Aug. 29, 2019

Related U.S. Application Data

(60) Provisional application No. 62/422,854, filed on Nov. 16, 2016, provisional application No. 62/485,001, filed on Apr. 13, 2017.

(51) Int. Cl.
*C12N 15/82* (2006.01)
*C12N 15/52* (2006.01)

(52) U.S. Cl.
CPC .......... *C12N 15/8251* (2013.01); *C12N 15/52* (2013.01); *C12N 15/8205* (2013.01); *C12N 15/8213* (2013.01); *C12N 2310/20* (2017.05)

(58) Field of Classification Search
CPC .................................................. C12N 15/8251
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,082,993 A | 1/1992 | Strissel et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,001,768 B2 | 2/2006 | Wolffe |
| 7,013,219 B2 | 3/2006 | Case et al. |
| 7,067,722 B2 | 6/2006 | Fillatti |
| 7,070,934 B2 | 7/2006 | Cox, III et al. |
| 7,163,824 B2 | 1/2007 | Cox, III et al. |
| 7,189,691 B2 | 3/2007 | Hemenway |
| 7,220,719 B2 | 5/2007 | Case et al. |
| 7,262,054 B2 | 8/2007 | Jamieson et al. |

(Continued)

FOREIGN PATENT DOCUMENTS

| | | |
|---|---|---|
| EP | 0 242 246 | 10/1987 |
| EP | 2 206 723 | 7/2010 |

(Continued)

OTHER PUBLICATIONS

Liu et al (A knockout mutation in the lignin biosynthesis gene CCR1 explains a major QTL for acid detergent lignin content in *Brassica napus* seeds. Theor Appl Genet 124:1573-1586, 2012) (Year: 2012).*
Castro-Chavez (The rules of variation: Amino acid exchange according to the rotating circular genetic code. J Theor Biol. 264(3):711-721, 2010). (Year: 2010).*
Shewry (Improving the protein content and composition of cereal grain. Journal of Cereal Science, 46, 239-250, 2007) (Year: 2007).*
Clark, A B, et al (Nucleic Acids Res. 27: 736-742, 1999) (Year: 1999).*
Foster et al (Adaptive Reversion of a Frameshift Mutation in *Escherichia coli* by Simple Base Deletions in Homopolymeric Runs. Science 265:407-409, 1994). (Year: 1994).*

(Continued)

*Primary Examiner* — Bratislav Stankovic
*Assistant Examiner* — Wayne Zhong
(74) *Attorney, Agent, or Firm* — Dicke, Billig & Czaja, PLLC

(57) ABSTRACT

Materials and methods are provided for making plants with altered levels of amino acids, particularly by making controlled frameshift mutations in genes that are highly expressed in plant leaves or plant seeds.

15 Claims, 13 Drawing Sheets
Specification includes a Sequence Listing.

(56) References Cited

U.S. PATENT DOCUMENTS

| | | |
|---|---|---|
| 7,273,923 B2 | 9/2007 | Jamieson et al. |
| 7,285,416 B2 | 10/2007 | Choo et al. |
| 7,361,635 B2 | 4/2008 | Miller et al. |
| 7,521,241 B2 | 4/2009 | Choo et al. |
| 7,842,489 B2 | 11/2010 | Arnould et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,586,363 B2 | 11/2013 | Voytas et al. |
| 8,697,853 B2 | 4/2014 | Voytas et al. |
| 9,035,129 B2 | 5/2015 | Bilyeu et al. |
| 9,198,365 B2 | 12/2015 | Bilyeu et al. |
| 2001/0016956 A1 | 8/2001 | Ward et al. |
| 2003/0236208 A1* | 12/2003 | Kmiec ............... C12N 15/102 514/44 R |
| 2005/0064474 A1 | 3/2005 | Umov et al. |
| 2006/0160222 A1* | 7/2006 | Rozwadowski ... C12N 15/8213 435/468 |
| 2007/0141038 A1 | 6/2007 | Choulika et al. |
| 2009/0060921 A1 | 3/2009 | Dickey et al. |
| 2009/0133158 A1 | 5/2009 | Lahaye et al. |
| 2009/0205070 A1 | 8/2009 | Dubcovsky et al. |
| 2009/0271881 A1 | 10/2009 | Arnould et al. |
| 2009/0305402 A1 | 12/2009 | Liljedahl et al. |
| 2010/0132069 A1 | 5/2010 | Lahaye et al. |
| 2010/0154081 A1 | 6/2010 | Weterings et al. |
| 2011/0041195 A1 | 2/2011 | Doyon |
| 2011/0129898 A1 | 6/2011 | Doyon et al. |
| 2011/0136895 A1 | 6/2011 | Gregory et al. |
| 2011/0145940 A1 | 6/2011 | Voytas et al. |
| 2011/0158957 A1 | 6/2011 | Bonini et al. |
| 2011/0167521 A1 | 7/2011 | DeKelver et al. |
| 2011/0201055 A1 | 8/2011 | Doyon et al. |
| 2011/0201118 A1 | 8/2011 | Yang et al. |
| 2011/0203012 A1 | 8/2011 | Dotson et al. |
| 2011/0207221 A1 | 8/2011 | Cost et al. |
| 2011/0239315 A1 | 9/2011 | Bonas et al. |
| 2011/0247089 A1 | 10/2011 | Doyon |
| 2011/0265198 A1 | 10/2011 | Gregory et al. |
| 2011/0269234 A1 | 11/2011 | Doyon et al. |
| 2011/0287545 A1 | 11/2011 | Cost et al. |
| 2011/0301073 A1 | 12/2011 | Gregory et al. |
| 2012/0110685 A1 | 5/2012 | Bonas et al. |
| 2012/0122205 A1 | 5/2012 | Bonas et al. |
| 2012/0178131 A1 | 7/2012 | Voytas et al. |
| 2012/0178169 A1 | 7/2012 | Voytas et al. |
| 2012/0214228 A1 | 8/2012 | Voytas et al. |
| 2012/0246764 A1 | 9/2012 | Hlubek et al. |
| 2012/0284877 A1 | 11/2012 | Hlubek et al. |
| 2012/0324603 A1 | 12/2012 | Hlubek et al. |
| 2013/0122581 A1 | 5/2013 | Voytas et al. |
| 2014/0090116 A1 | 3/2014 | Ainley et al. |
| 2015/0291967 A1 | 10/2015 | Mathis et al. |
| 2017/0096649 A1* | 4/2017 | Quake ............... C12Y 301/00 |

FOREIGN PATENT DOCUMENTS

| | | |
|---|---|---|
| EP | 2 392 208 | 12/2011 |
| EP | 2 562 260 | 2/2013 |
| WO | WO 1994/18313 | 8/1994 |
| WO | WO 1995/09233 | 4/1995 |
| WO | WO 00/40709 | 7/2000 |
| WO | WO 01/25460 | 4/2001 |
| WO | WO 01/85970 | 11/2001 |
| WO | WO 03/000905 | 1/2003 |
| WO | WO 2004/067736 | 8/2004 |
| WO | WO 2005/047472 | 5/2005 |
| WO | WO 2005/098015 | 10/2005 |
| WO | WO 2007/060495 | 5/2007 |
| WO | WO 2007/147064 | 12/2007 |
| WO | WO 2008/141806 | 11/2008 |
| WO | WO 2009/095793 | 8/2009 |
| WO | WO 2010/079430 | 7/2010 |
| WO | WO 2010/091018 | 8/2010 |
| WO | WO 2010/145846 | 12/2010 |
| WO | WO 2011/005998 | 1/2011 |
| WO | WO 2011/017293 | 2/2011 |
| WO | WO 2011/019385 | 2/2011 |
| WO | WO 2011/072246 | 6/2011 |
| WO | WO 2011/100058 | 8/2011 |
| WO | WO 2011/117249 | 9/2011 |
| WO | WO 2011/146121 | 11/2011 |
| WO | WO 2011/154393 | 12/2011 |
| WO | WO 2012/106105 | 8/2012 |
| WO | WO 2013/029800 | 3/2013 |
| WO | WO 2013/050155 | 4/2013 |
| WO | WO 2014/039692 | 3/2014 |
| WO | WO 2014/039702 | 3/2014 |
| WO | WO 2014/144155 | 9/2014 |
| WO | WO 2014/182897 | 11/2014 |
| WO | WO 2016/041952 | 3/2016 |
| WO | WO 2016/057106 | 4/2016 |
| WO | WO 2018/005589 | 1/2018 |

OTHER PUBLICATIONS

Ansai et al (Efficient Targeted Mutagenesis in Medaka Using Custom-Designed Transcription Activator-Like Effector Nucleases. Genetics, vol. 193, 739-749, 2013). (Year: 2013).*

Castro-Chavez (The rules of variation: Amino acid exchange according to the rotating circular genetic code. J Theor Biol. Jun. 7, 2010; 264(3): 711-721, 2010). (Year: 2010).*

U.S. Appl. No. 61/225,043, filed Jul. 13, 2009, Bonas et al.

"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).

Alam and Sittman, "Characterization of the cytotoxic effect of a chimeric restriction enzyme, H1°-FokI," Gene. Ther. Mol. Biol., 10:147-160, 2006.

Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.

Al-Saadi et al., "All five host-range variants of Xanthomonas citri carry one pthA homolog with 17.5 repeats that determines pathogenicity on citrus, but none determine host-range variation," Mol. Plant Microbe Interact, 20(8):934-943, Aug. 2007.

Antony et al., "Rice xa13 recessive resistance to bacterial blight is defeated by induction of the disease susceptibility gene Os-11N3," Plant Cell, 22(11):3864-3876, Nov. 2010.

Antony, "Molecular basis of avrXa7 mediated virulence in bacterial blight of rice," [abstract of dissertation] Kansas State University, 99 pages, 2010.

Arimondo et al., "Exploring the cellular activity of camptothecin-triple-helix-forming oligonucleotide conjugates," Mol. Cell Biol., 26(1):324-333, Jan. 2006.

Athinuwat et al., "*Xanthomonas axonopodis* pv. *glycines* soybean cultivar virulence specificity is determined by avrBs3 homolog avrXg1," Phytopathology, 99(8):996-1004, Aug. 2009.

Bai et al., "*Xanthomonas oryzae* pv. *oryzae* avirulence genes contribute differently and specifically to pathogen aggressiveness," Mol. Plant Microbe Interact, 13(12):1322-1329, Dec. 2000.

Baker, "Gene-editing nucleases," Nature Methods, 9(4):23-26, Jan. 2012.

Ballvora et al., "Genetic mapping and functional analysis of the tomato Bs4 locus governing recognition of the *Xanthomonas campestris* pv. *vesicatoria* AvrBs4 protein," Mol. Plant Microbe Interact, 14(5):629-638, May 2001.

Barton et al., "The Biosynthesis and Processing of High Molecular Weight Precursors of Soybean Glycinin Subunits," J. Biol. Chem., 257(11):6089-6095, Jun. 1982.

Beachy et al., "Biosynthesis of Subunits of the Soybean 7S Storage Protein," J. Mol. Appl. Genet., 1(1):19-27, 1981.

(56) References Cited

OTHER PUBLICATIONS

Belhaj et al., "Plant genome editing made easy: targeted mutagenesis in model and crop plants using the CRISPR/Cas system," Plant Methods, 9(1):39, Dec. 2013.
Beretta et al., "Tethering a type IB topoisomerase to a DNA site by enzyme fusion to a heterologous site-selective DNA-binding protein domain," Cancer Res., 59(15):3689-3697, Aug. 1999.
Bethke and Busse, "Validation of a simple, colorimetric, microplate assay using amplex red for the determination of glucose and sucrose in potato tubers and other vegetables," Am. J. Pot Res., 85(6):414-421, Dec. 2008.
Beuselinck et al., "An Assessment of Phenotype Selection for Linolenic Acid Using Genetic Markers," Crop Sci., 46(2):747-750, Mar. 2006.
Bhaskar et al., "Suppression of the vacuolar invertase gene prevents cold-induced sweetening in potato," Plant Physiol., 154(2):939-948, Oct. 2010.
Bibikova et al., "Enhancing gene targeting with designed zinc finger nucleases," Science, 300(5620):764, May 2003.
Bibikova et al., "Stimulation of homologous recombination through targeted cleavage by chimeric nucleases," Mol. Cell Biol., 21(1):89-297, Jan. 2001.
Bitinaite et al., "FokI dimerization is required for DNA cleavage," Proc. Natl. Acad. Sci. USA, 95(18):10570-10575, Sep. 1998.
Boch and Bonas, "Xanthomonas AvrBs3 family-type III effectors: discovery and function," Annu. Rev. Phytopathol., 48:419-436, Sep. 2010.
Boch et al., "Breaking the code of DNA binding specificity of TAL-type III effectors," Science, 326(5959):1509-1512, Dec. 2009.
Boch et al., "Molecular characterization of three AvrBs3-like effectors from the *Arabidopsis* pathogen *Xanthomonas campestris* pv. *armoraciae*," (abstract), XIV International Congress on Molecular Plant-Microbe Interactions, Quebec City, Canada, Jul. 19-23, 2009, 2 pages.
Bogdanove and Voytas, "TAL effectors: Customizable Proteins for DNA Targeting," Science, 333(6051):1843-1846, Sep. 2011.
Bogdanove et al., "TAL effectors: finding plant genes for disease and defense," Curr. Opin. Plant Biol., 13(4):394-401, Aug. 2010.
Boller and He, "Innate immunity in plants: an arms race between pattern recognition receptors in plants and effectors in microbial pathogens," Science, 324(5928):742-744, May 2009.
Bonas et al., "Genetic and structural characterization of the avirulence gene avrBs3 from *Xanthomonas campestris* pv. *vesicatoria*," Mol. Gen. Genet., 218(1):127-136, Jul. 1989.
Bonas et al., "How the bacterial plant pathogen *Xanthomonas campestris* pv. *vesicatoria* conquers the host," Mol. Plant Pathol., 1(1):73-76, Jan. 2000.
Bonas et al., "Resistance in tomato to *Xanthomonas campestris* pv *vesicatoria* is determined by alleles of the pepper-specific avirulence gene avrBs3," Mol. Gen. Genet., 238(1-2):261-269, Apr. 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12(12):2383-2394, Dec. 2000.
Bright et al., "Threonine Accumulation in the Seeds of a Barley Mutant With an Altered Aspartate Kinase," Biochem. Genet., 20(3-4):229-243, Apr. 1982.
Busk et al., "Regulatory elements in vivo in the promoter of the abscisic acid responsive gene rab17 from maize," Plant J., 11(6):1285-1295, Dec. 1997.
Büttner and Bonas, "Getting across—bacterial type III effector proteins on their way to the plant cell," EMBO J., 21(20):5313-5322, Oct. 2002.
Büttner et al., "Functional analysis of HrpF, a putative type III translocon protein from *Xanthomonas campestris* pv. *vesicatoria*," J. Bacteriol., 184(9):2389-2398, May 2002.

Büttner et al., "HpaB from *Xanthomonas campestris* pv. *vesicatoria* acts as an exit control protein in type III-dependent protein secretion," Mol. Microbiol., 54(3):755-768, Nov. 2004.
Büttner et al., "Targeting of two effector protein classes to the type III secretion system by a HpaC-and HpaB-dependent protein complex from *Xanthomonas campestris* pv. *vesicatoria*," Mol. Microbiol., 59(2):513-527, Jan. 2006.
Canteros et al., "A Gene from *Xanthomonas campestris* pv. *vesicatoria* that Determines," Mol. Plant Microbe Interact., 4(6):628-632, Aug. 1991.
Carlson et al., "Targeting DNA with fingers and TALENs," Mol. Ther. Nucl. Acids, 1:1-4, Jan. 2012.
Cathomen and Joung, "Zinc-finger nucleases: the next generation emerges," Mol. Ther., 16(7):1200-1207, Jul. 2008.
Cavalier et al., "Disrupting two *Arabidopsis thaliana* xylosyltransferase genes results in plants deficient in xyloglucan, a major primary cell wall component," The Plant Cell, 20(6):1519-1537, Jun. 2008.
Cermak et al., "Efficient design and assembly of custom TALEN and other TAL effector-based constructs for DNA targeting," Nucleic Acids Res., 39(12):e82, Jul. 2011.
Cermak et al., Poster and Abstract—"Engineered TAL effector nucleases: new tools for genome editing," Northwest Genome Engineering Consortium Workshop on Genome Engineering, 3 pages, 2010.
Chevalier et al., "Design, activity, and structure of a highly specific artificial endonuclease," Mol. Cell, 10(4):895-905, Oct. 2002.
Choo et al., "In vivo repression by a site-specific DNA-binding protein designed against an oncogenic sequences," Nature, 372(6507):642-645, Dec. 1994.
Choulika et al., "Induction of homologous recombination in mammalian chromosomes by using the I-ScelI system of *Saccharomyces cerevisiae*," Mol Cell Biol, 15(4):1968-1973, Apr. 1995.
Christian et al., "Targeting DNA double-strand breaks with TAL effector nucleases," Genetics, 186(2):757-761, Oct. 2010.
Christian et al., Poster and Abstract—"Fusions of TAL effectors to the FokI endonuclease confer site specificity in DNA cleavage," IAPB 12th World Congress and In Vitro Biology Meeting, 4 pages, Jun. 2010.
Cole et al., "The Jpred 3 secondary structure prediction server," Nucl. Acids Res., 36(Suppl_2):W197-W201, May 2008.
Cornelis, "The type III secretion injectisome,"Nat. Rev. Microbiol., 4(11):811-825, Nov. 2006.
Curtin et al., "Targeted mutagenesis of duplicated genes in soybean with zinc-finger nucleases," Plant Physiology, 156(2):466-473, Jun. 2011.
De Feyter et al., "Gene-for genes interactions between cotton R genes and *Xanthomonas campestris* pv. *malvacearum* avr genes," Mol. Plant Microbe Interact, 6(2):225-237, Mar.-Apr. 1993.
De Onis et al., "The worldwide magnitude of protein-energy malnutrition: an overview from the WHO Global Database on Child Growth," Bulletin of the World health Organization, 71(6):703, 1993.
DeFrancesco, "Move over ZFNs," Nat. Biotechnol., 29(8):681-684, Aug. 2011.
Desjarlais and Berg, "Toward rules relating zinc finger protein sequences and DNA binding site preferences," Proc. Natl. Acad. Sci. USA, 89(16):7345-7349, Aug. 1992.
Dhir et al., "Plantlet Regeneration From Immature Cotyledon Protoplasts of Soybean (*Glycine max* L.)," Plant Cell Rep., 10(1):39-43, May 1991.
Domingues et al., "The Xanthomonas citri effector protein PthA interacts with citrus proteins involved in nuclear transport, protein folding and ubiquitination associated with DNA repair," Mol. Plant Pathol., 11(5):663-675, Sep. 2010.
Doyle et al., "TAL Effector-Nucleotide Targeter (TALE-NT) 2.0: tools for TAL effector design and target prediction," Nucleic Acids Res., 40(W1):W117-22, Jul. 2012.
Draffehn et al., "Natural diversity of potato (*Solanum tuberosum*) invertases," BMC Plant Biol., 10(271):1-15, Dec. 2010.
Dubois et al., "Molecular diversity of α-gliadin expressed genes in genetically contrasted spelt (*Triticum aestivum* ssp. *spelta*) accessions and comparison with bread wheat (*T. aestivum* ssp. *aestivum*)

(56) References Cited

OTHER PUBLICATIONS and related diploid Triticum and Aegilops species," Molecular Breeding, 36(11):152, Nov. 2016.
Durai et al., "Zinc finger nucleases: custom-designed molecular scissors for genome engineering of plant and mammalian cells," Nucl. Acids Res., 33(18):5978-5990, Jan. 2005.
Eisenschmidt et al., "Developing a programmed restriction endonuclease for highly specific DNA cleavage," Nucl. Acids Res., 33(22):7039-7047, Jan. 2005.
Engler et al., "A One Pot, One Step, Precision Cloning Method with High Throughput Capability," PLoS One, 3(11):e3647, Nov. 2008.
Engler et al., "Golden Gate Shuffling: A One-Pot DNA Shuffling Method Based on Type IIs Restriction Enzymes," PLoS One, 4(5):e5553, May 2009.
Fajardo-Sanchez et al., "Computer design of obligate heterodimer meganucleases allows efficient cutting of custom DNA sequences," Nucl. Acids Res., 36(7):2163-2173, Apr. 2008.
Foley et al., "Rapid Mutation of Endogenous Zebrafish Genes Using Zinc Finger Nucleases Made by Oligomerized Pool ENgineering (OPEN)," PLoS One, 4(2):e4348, Feb. 2009.
Fonfara et al., "Creating highly specific nucleases by fusion of active restriction endonucleases and catalytically inactive homing endonucleases," Nucl. Acids Res., 40(2):847-860, Jan. 2012.
Fujikawa et al., "Suppression of defense response in plants by the avrBs3/pth A gene family of *Xanthomonas* spp," Mol. Plant Microbe Interact, 19(3):342-349, Mar. 2006.
Gabriel et al., "An unbiased genome-wide analysis of zinc-finger nuclease specificity," Nat. Biotechnol., 29(9):816-823, Sep. 2011.
Galili et al., "Improving the Levels of Essential Amino Acids and Sulfur Metabolites in Plants," Biol. Chem., 386(9):817-831, Sep. 2005.
Gao et al., "Auxin binding protein 1 (ABP1) is not required for either auxin signaling or *Arabidopsis* development," Proceedings of the National Academy of Sciences, 112(7):2275-80, Feb. 2015.
Geißler et al., "Transcriptional activators of human genes with programmable DNA-specificity," PLoS One, 6(5):e19509, May 2011.
GenBank Accession No. JN831386.1, "Triticum aestivum clone 1-8 alpha-gliadin (gli-2) gene, complete cds," dated Feb. 12, 2012, 2 pages.
GenBank Accession No. X12928.5, "Triticum aestivum Glu-1D-1d gene for high molecular weight glutenin subunit 5," dated Feb. 13, 2010, 4 pages.
GenBank Accession No. AAT46122.1, "avirulence protein AvrXa7-1M [*Xanthomonas oryzae* pv. *oryzae*]," Nov. 12, 2004, 2 pages.
GenBank Accession No. ACD58243.1, "TAL effector AvrBs3/PthA [*Xanthomonas oryzae* pv. *oryzae* PXO99A]," May 19, 2008, 2 pages.
GenBank Accession No. AY986492.1, "Oryza sativa (indica cultivar-group) Xa27 (Xa27) gene, Xa27-IRBB27 allele, complete cds," Jun. 24, 2005, 2 pages.
GenBank Accession No. CP000967.1, "*Xanthomonas oryzae* pv. *oryzae* PXO99A, complete genome," May 19, 2008, 606 pages.
GenBank Accession No. J04623.1, "F.okeanokoites methylase (MFokI) and endonuclease (RFokI) genes, complete cds," Apr. 26, 1993, 2 pages.
GenBank Accession No. M28828.1, "F.okeanokoites fokIR and fokIM genes encoding endonuclease and methyltransferase, complete cds," Apr. 26, 1993, 3 pages.
GenBank Accession No. P14727.2, "RecName: Full=Avirulence protein AvrBs3; AltName: Full=TAL effector protein AvrBs3," Jun. 28, 2011, 3 pages.
GenBank Accession No. X16130.1, "Xanthomonas vesicatoria plasmid pXV11 avrBs3 gene for avirulence protein avrBs3," Oct. 15, 2007, 3 pages.
Ghislain et al., "A dinucleotide mutation in dihydrodipicolinate synthase of Nicotiana sylvestris leads to lysine overproduction," Plant J., 8(5):733-743, Nov. 1995.

Gil-Humanes et al., "Effective Shutdown in the Expression of Celiac Disease-Related Wheat Gliadin T-cell Epitopes by RNA Interference," Proc. Natl. Acad. Sci. USA, 107(39):17023-17028, Sep. 2010.
Göhre and Robatzek, "Breaking the barriers: microbial effector molecules subvert plant immunity," Ann. Rev. Phytopathol., 46:189-215, Sep. 2008.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
Gonzalez et al., "Molecular and pathotypic characterization of new Xanthomonas oryzae strains from West Africa," Mol. Plant Microbe. Interact., 20(5):534-546, May 2007.
Goto et al., "A single-nucleotide mutation in a gene encoding S-adenosylmethionine synthetase is associated with methionine over-accumulation phenotype in *Arabidopsis thaliana*," Genes. Genet. Syst., 77(2):89-95, 2002.
Govindarajulu et al., "Evaluation of constitutive viral promoters in transgenic soybean roots and nodules," Mol. Plant Microbe Interact, 21(8):1027-1035, Aug. 2008.
Greiner et al., "Ectopic expression of a tobacco invertase inhibitor homolog prevents cold-induced sweetening of potato tubers," Nature Biotechnology, 17(7):708-711, Jul. 1999.
Greisman and Pabo, "A general strategy for selecting high-affinity zinc finger proteins for diverse DNA target sites," Science, 275(5300):657-661, Jan. 1997.
Gu et al., "R gene expression induced by a type-III effector triggers disease resistance in rice," Nature, 435(7045):1122-1125, Jun. 2005.
Gu et al., "Transcription activator-like type III effector AvrXa27 depends on OsTFIIAγ5 for the activation of Xa27 transcription in rice that triggers disease resistance to *Xanthomonas oryzae* pv. *oryzae*," Mol. Plant Pathol., 10(6):829-835, Nov. 2009.
Guan et al., "Heritable endogenous gene regulation in plants with designed polydactyl zinc finger transcription factors," Proc Natl Acad Sci USA, 99(20):13296-13301, Oct. 2002.
Gürlebeck et al., "Dimerization of the bacterial effector protein AvrBs3 in the plant cell cytoplasm prior to nuclear import," Plant J., 42(2):175-187, Apr. 2005.
Gürlebeck et al., "Type III effector proteins from the plant pathogen Xanthomonas and their role in the interaction with the host plant," J. Plant Physiol., 163(3):233-255, Feb. 2006.
Gürlebeck et al., "Visualization of novel virulence activities of the Xanthomonas type III effectors AvrBs1, AvrBs3 and AvrBs4," Mol. Plant Pathol., 10(2):175-188, Mar. 2009.
Haber, "In vivo biochemistry: physical monitoring of recombination induced by site-specific endonucleases," Bioessays, 17(7):609-620, Jul. 1995.
Haberlach et al., "Isolation, culture and regeneration of protoplasts from potato and several related Solanum species," Plant Science, 39(1):67-74 May 1985.
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem. Soc. Trans., 39(2):584-588, Apr. 2011.
Händel et al., "Expanding or restricting the target site repertoire of zinc-finger nucleases: the inter-domain linker as a major determinant of target site selectivity," Mol. Ther., 17(1):104-111, Jan. 2009.
Haun et al., "Improved soybean oil quality by targeted mutagenesis of fatty acid desaturase 2 gene family," Plant Biotechnology Journal, 12(7):934-40, Sep. 2014.
Herbers et al., "Race-specificity of plant resistance to bacterial spot disease determined by repetitive motifs in a bacterial avirulence protein," Nature, 356(6365):172-174, Mar. 1992.
Heuer et al., "Repeat domain diversity of avrBs3-like genes in Ralstonia solanacearum strains and association with host preferences in the field," Appl. Environ. Microbiol., 73(13):4379-4384, Jul. 2007.

(56) References Cited

OTHER PUBLICATIONS

Hill and Breidenbach, "Proteins of Soybean Seeds: II. Accumulation of the Major Protein Components During Seed Development and Maturation," Plant Physiol., 53(5):747-751, May 1974.
Hockemeyer et al., "Genetic engineering of human pluripotent cells using TALE nucleases," Nat. Biotechnol., 29(8):731-734, Aug. 2011.
Hopkins et al., "Identification of a Family of Avirulence Genes From *Xanthomonas oryzae* Pv. *Oryzae*," Mol. Plant Microbe Interact, 5(6):451-459, Nov.-Dec. 1992.
Hu et al., "A virulence gene and insertion element-based RFLP as well as RAPD markers reveal high levels of genomic polymorphism in the rice pathogen *Xanthomonas oryzae* pv. *oryzae*," Syst. Appl. Microbiol., 30(8):587-600, Dec. 2007.
Huang et al., "Improving nutritional quality of maize proteins by expressing sense and antisense zein genes," J. Agric. Food Chem., 52(7):1958-1964, Apr. 2004.
Huang et al., "Heritable gene targeting in zebrafish using customized TALENs," Nat. Biotechnol., 29(8):699-700, Aug. 2011.
Hummel et al., "Rice gene activation by transcription activator-like effectors of *Xanthomonas oryzae* pvs. *oryzae* and *oryzicola*," poster presentation, and "A cipher-like mechanism governs TAL effector-DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc. Natl. Acad. Sci. USA, 100(21):12271-12276, Oct. 2003.
International Preliminary Report on Patentability in International Application No. PCT/IB2017/057190 dated May 21, 2019, 17 pages.
International Search Report & Written Opinion in International Application No. PCT/IB2017/057190 dated Mar. 28, 2018, 17 pages.
Isalan et al., "A rapid, generally applicable method to engineer zinc fingers illustrated by targeting the HIV-1 promoter," Nat. Biotechnol., 19(7):656-660, Jul. 2001.
Jäckel et al., "Protein Design by Directed Evolution," Annu. Rev. Biophys., 37:155-173, 2008.
Jones and Dangl, "The plant immune system," Nature, 444(7117):323-329, Nov. 2006.
Jordan et al., "Physical delimitation of the pepper Bs3 resistance gene specifying recognition of the AvrBs3 protein from *Xanthomonas campestris* pv. *vesicatoria*," Theor. Appl. Genet., 113(5):895-905, Sep. 2006.
Kay and Bonas, "How Xanthomonas type III effectors manipulate the host plant," Curr. Opin. Microbiol., 12(1):37-43, Feb. 2009.
Kay et al., "A bacterial effector acts as a plant transcription factor and induces a cell size regulator," Science, 318(5850):648-651, Oct. 2007.
Kay et al., "Characterization of AvrBs3-like effectors from a Brassicaceae pathogen reveals virulence and avirulence activities and a protein with a novel repeat architecture," Mol. Plant Microbe Interact, 18(8):838-848, Aug. 2005.
Kay et al., "Detailed analysis of the DNA recognition motifs of the Xanthomonas type III effectors AvrBs3 and AvrBs3Δrep16," Plant J, 59(6):859-871, Sep. 2009.
Keshavarzi et al., "Basal defenses induced in pepper by lipopolysaccharides are suppressed by *Xanthomonas campestris* pv. *vesicatoria*," Mol. Plant Microbe Interact, 17(7):805-815, Jul. 2004.
Kim and Chandrasegaran, "Chimeric restriction endonuclease," Proc. Natl. Acad. Sci. USA, 91(3):883-887, Feb. 1994.
Kim et al., "Constitutive Overexpression of Cystathionine Gamma-Synthase in *Arabidopsis* Leads to Accumulation of Soluble Methionine and S-methylmethionine," Plant Physiol., 128(1):95-107, Jan. 2002.
Kim et al., "Comparative analysis of three indigenous plasmids from *Xanthomonas axonopodis* pv. *glycines*," Plasmid, 56(2):79-87, Sep. 2006.

Kim et al., "Construction of a Z-DNA-specific restriction endonuclease," Proc. Natl. Acad. Sci. USA, 94(24):12875-12879, Nov. 1997.
Kim et al., "Hybrid restriction enzymes: zinc finger fusions to FokI cleavage," Proc. Natl. Acad. Sci. USA, 93(3):1156-1160, Feb. 1996.
Kim et al., "Site-specific cleavage of DNA-RNA hybrids by zinc finger/FokI cleavage domain fusions," Gene, 203(1):43-49, Dec. 1997.
Kim et al., "Targeted genome editing in human cells with zinc finger nucleases constructed via modular assembly," Genome Res., 19(7):1279-1288, Jul. 2009.
Knoop et al., "Expression of avirulence gene avrBs3 from *Xanthomonas campestris* pv. *vesicatoria* is not under the control of hrp genes and is independent of plant factors," J. Bacteriol., 173(22):7142-7150, Nov. 1991.
Lahaye and Bonas, "Molecular secrets of bacterial type III effector proteins," Trends Plant Sci., 6(10):479-485, Oct. 2001.
Ledford, "Plant genes get fine tailoring," Nature News [online], Apr. 29, 2009 [retrieved on May 21, 2009], Retrieved from the Internet: <URL: http://www.nature.com/news/2009/090429/full/news.2009.415.html>, 3 pages.
Lee et al., "Environmental effects on oleic acid in soybean seed oil of plant introductions with elevated oleic concentration," Crop Science, 49(5):1762-1768, Sep. 2009.
Li et al., "Functional domains in FokI restriction endonuclease," Proc. Natl. Acad. Sci. USA, 89(10):4275-4279, May 1992.
Li et al., "Modularly assembled designed TAL effector nucleases for targeted gene knockout and gene replacement in eukaryotes," Nucl. Acids Res., 39(14):6315-6325, Aug. 2011.
Li et al., "TAL nucleases (TALNs): hybrid proteins composed of TAL effectors and FokI DNA-cleavage domain," Nucleic Acids Res., 39(1):359-372, Jan. 2011.
Liang et al., "Cloning and characterization of a novel avirulence gene (arp3) from *Xanthomonas oryzae* pv. *oryzae*," DNA Seq., 15(2):110-117, Apr. 2004.
Liu et al., "Design of polydactyl zinc-finger proteins for unique addressing within complex genomes," Proc. Natl. Acad. Sci. USA, 94(11):5525-5530, May 1997.
Livak and Schmittgen, "Analysis of relative gene expression data using real-time quantitative PCR and the 2(-Delta Delta C(T)) Method," Method. Methods, 25(4):402-408, Dec. 2001.
Mahfouz et al., "De novo-engineered transcription activator-like effector (TALE) hybrid nuclease with novel DNA binding specificity creates double-strand breaks," Proc. Natl. Acad. Sci. USA, 108(6):2623-2628, Feb. 2011.
Mahfouz et al., "TALE nucleases and next generation GM crops," GM Crops, 2(2):99-103, Apr. 2011.
Mak, "Sequence-specific DNA-binding TALEs," Nat. Biotechnol., 29(1):43, Jan. 2011.
Marois et al., "The Xanthomonas type III effector protein AvrBs3 modulates plant gene expression and induces cell hypertrophy in the susceptible host," Mol. Plant Microbe Interact, 15(7):637-646, Jul. 2002.
Miller et al., "A TALE nuclease architecture for efficient genome editing," Nat. Biotechnol., 29(2):143-148, Feb. 2011.
Miller et al., "An improved zinc-finger nuclease architecture for highly specific genome editing," Nature Biotechnol., 25(7):778-785, Jul. 2007.
Minczuk et al., "Development of a single-chain, quasi-dimeric zinc-finger nuclease for the selective degradation of mutated human mitochondrial DNA," Nucleic Acids Res., 36(12):3926-3938, Jul. 2008.
Mino et al., "Efficient double-stranded DNA cleavage by artificial zinc-finger nucleases composed of one zinc-finger protein and a single-chain FokI dimer," J. Biotechnol., 140(3-4):156-161, Mar. 2009.
Moore et al., "Transactivated and chemically inducible gene expression in plants," Plant J., 45(4):651-683, Feb. 2006.
Morbitzer et al., "Assembly of custom TALE-type DNA binding domains by modular cloning," Nucleic Acids Res., 39(13):5790-5799, Jul. 2011.

(56) References Cited

OTHER PUBLICATIONS

Morbitzer et al., "Regulation of selected genome loci using de novo-engineered transcription activator-like effector (TALE)-type transcription factors," Proc. Natl. Acad. Sci. USA., 107(50):21617-21622, Dec. 2010.
Moscou and Bogdanove, "A Simple Cipher Governs DNA Recognition by TAL Effectors," Science, 326(5959):1501, Dec. 2009.
Murakami et al., "The repeat domain of the type III effector protein PthA shows a TPR-like structure and undergoes conformational changes upon DNA interaction," Proteins, 78(16):3386-3395, Dec. 2010.
Murray and Thompson, "Rapid isolation of high molecular weight plant DNA," Nucl. Acids. Res., 8(19):4321-4325, Oct. 1980.
Mussolino et al., "A novel TALE nuclease scaffold enables high genome editing activity in combination with low toxicity," Nucleic Acids Res., 39(21):9283-9293, Nov. 2011.
Nakagawa et al., "Development of series of gateway binary vectors, pGWBs, for realizing efficient construction of fusion genes for plant transformation," J. Biosci. Bioeng., 104(1):34-41, Jul. 2007.
Nino-Liu et al., "Xanthomonas oryzae pathovars: model pathogens of a model crop," Mol. Plant Pathol., 7(5):303-324, Sep. 2006.
Nissan et al., "The type III effectors HsvG and HsvB of gall-forming Pantoea agglomerans determine host specificity and function as transcriptional activators," Molecular Microbiology, 61(5):1118-1131, Sep. 2006.
Noel et al., "XopC and XopJ, two novel type III effector proteins from Xanthomonas campestris pv. vesicatoria," J. Bacteriol., 185(24):7092-7102, Dec. 2003.
Ovchinnikov et al., "PspXI, a novel restriction endonuclease that recognizes the unusual DNA sequence 5-VCTCGAGB-3," Bull Biotech. Physio-Chemical Biol., 2005, 1(1):18-24, retrieved from the Internet: http://science.sibenzyme.com/article8_article_3_1.phtml.
Padidam, "Chemically regulated gene expression in plants," Curr. Opin. Plant Biol., 6(2):169-177, Apr. 2003.
Pâques and Duchateau, "Meganucleases and DNA double-strand break-induced recombination: perspectives for gene therapy," Curr. Gene Ther., 7(1):49-66, Feb. 2007.
Park et al., "Avirulence gene diversity of Xanthomonas axonopodis pv. glycines isolated in Korea," J. Microbiol. Biotechnol., 18(9):1500-1509, Sep. 2008.
Pattanayak et al., "Revealing off-target cleavage specificities of zinc-finger nucleases by in vitro selection," Nat. Methods, 8(9):765-770, Sep. 2011.
Paulus et al., "Silencing β1, 2-xylosyltransferase in transgenic tomato fruits reveals xylose as constitutive component of IgE-binding epitopes," Fronties in Plant Science, 2(42):1-12, Aug. 2011.
Pavletich and Pabo, "Zinc finger-DNA recognition: crystal structure of a Zif268-DNA complex at 2.1 A," Science, 252(5007):809-817, May 1991.
Paz et al., "Improved Cotyledonary Node Method Using an Alternative Explant Derived From Mature Seed for Efficient Agrobacterium-mediated Soybean Transformation," Plant Cell Re., 25(3):206-213, Mar. 2006.
Pearson, "The fate of fingers: proteins with 'zinc fingers' designed to bind almost any DNA sequence will soon be available to any lab that wants them—from two very different sources. Helen Pearson reports on a revolution in designer biology," Nature, 455(7210):160-165, Sep. 2008.
Pennisi, "The tale of the TALEs," Science, 338(6113):1408-1411, Dec. 2012.
Pham et al., "Mutant alleles of FAD2-1A and FAD2-1B combine to produce soybeans with the high oleic acid seed oil trait.," BMC Plant Biol., 10(1):195, Dec. 2010.
Pingoud and Silva, "Precision genome surgery," Nature Biotechnol., 25(7):743-744, Jul. 2007.
Podhajska and Szybalski, "Conversion of the FokI endonuclease to a universal restriction enzyme: cleavage of phage M13mp7 DNA at predetermined sites," Gene, 40(2-3):175-182, Jan. 1985.
Pomerantz et al., "Structure-based design of transcription factors," Science, 267(5194):93-96, Jan. 1995.
Porteus and Baltimore, "Chimeric Nucleases Stimulate Gene Targeting in Human Cells," Science, 300(5620):763, May 2003.
Porteus and Carroll, "Gene targeting using zinc finger nucleases," Nature Biotechnol., 23(8):967-973, Aug. 2005.
Porteus, "Zinc fingers on target," Nature, 459(7245):337-338, May 2009.
Potenza et al., "Targeting transgene expression in research, agricultural, and environmental applications: promoters used in plant transformation," In vitro Cell Dev. Biol., 40(1):1-22, Jan. 2004.
Prilusky et al., "FoldIndex©: a simple tool to predict whether a given protein sequence is intrinsically unfolded," Bioinformatics., 21(16):3435-8, Aug. 2005.
Puchta et al., "Homologous recombination in plant cells is enhanced by in vivo induction of double strand breaks into DNA by a site-specific endonuclease," Nucl. Acids Res., 21(22):5034-5040, Nov. 1993.
Radecke et al., "Zinc-finger nuclease-induced gene repair with oligodeoxynucleotides: wanted and unwanted target locus modifications," Mol. Ther., 18(4):743-753, Apr. 2010.
Reyes et al., "Genetic Manipulation of Lysine Catabolism in Maize Kernels," Plant Mol. Biol., 69(1-2):81-89, Jan. 2009.
Reyon et al., "FLASH assembly of TALENs for high-throughput genome editing," Nat. Biotechnol., 30(5):460-465, May 2012.
Romer et al., "Plant pathogen recognition mediated by promoter activation of the pepper Bs3 resistance gene," Science, 318(5850):645-648, Oct. 2007.
Romer et al., "A single plant resistance gene promoter engineered to recognize multiple TAL effectors from disparate pathogens," Proc. Natl. Acad. Sci. USA, 106(48):20526-31, Dec. 2009.
Römer et al., "Promoter elements of rice susceptibility genes are bound and activated by specific TAL effectors from the bacterial blight pathogen, Xanthomonas oryzae pv. oryzae," New Phytol., 187(4):1048-1057, Sep. 2010.
Römer et al., "Recognition of AvrBs3-Like Proteins is Mediated by Specific Binding to Promoters of Matching Pepper Bs3 Alleles," Plant Physiol., 150(4):1697-1712, Aug. 2009.
Romero et al., "Temperature sensitivity of the hypersensitive response of bell pepper to Xanthomonas axonopodis pv. vesicatoria," Phytopathology, 92(2):197-203, Feb. 2002.
Rossier et al., "HrpB2 and HrpF from Xanthomonas are type III-secreted proteins and essential for pathogenicity and recognition by the host plant," Mol. Microbiol., 38(4):828-838, Nov. 2000.
Rossier et al., "The Xanthomonas Hrp type III system secretes proteins from plant and mammalian bacterial pathogens," Proc. Natl. Acad. Sci. USA, 96(16):9368-9373, Aug. 1999.
Rouet et al., "Expression of a site-specific endonuclease stimulates homologous recombination in mammalian cells," Proc. Natl. Acad. Sci. USA, 91(13):6064-6068, Jun. 1994.
Rouet et al., "Introduction of double-strand breaks into the genome of mouse cells by expression of a rare-cutting endonuclease," Mol. Cell Biol., 14(12):8096-8106, Dec. 1994.
Rybak et al., "Identification of Xanthomonas citri ssp. citri host specificity genes in a heterologous expression host," Mol. Plant Pathol., 10(2):249-262, Mar. 2009.
Sandhu et al., "Enhanced oleic acid content in the soybean mutant M23 is associated with the deletion in the Fad2-1a gene encoding a fatty acid desaturase," JAOCS, 84(3):229-235, Mar. 2007.
Santiago et al., "Targeted gene knockout in mammalian cells by using engineered zinc-finger nucleases," Proc. Natl. Acad. Sci. USA, 105(15):5809-5814, Apr. 2008.
Schmidt and Herman, "Proteome Rebalancing in Soybean Seeds Can Be Exploited to Enhance Foreign Protein Accumulation," Plant Biotech. J., 6(8):832-842, Oct. 2008.
Schmidt et al., "Silencing of Soybean Seed Storage Proteins Results in a Rebalanced Protein Composition Preserving Seed Protein Content Without Major Collateral Changes in the Metabolome and Transcriptome," Plant Physiology, 156(1):330-345, May 2011.
Scholze and Boch, "TAL effector-DNA specificity," Virulence, 1(5):428-432, Sep. 2010.
Scholze and Boch, "TAL effectors are remote controls for gene activation," Curr. Opin. Microbiol., 14(1):47-53, Feb. 2011.

(56) References Cited

OTHER PUBLICATIONS

Schomack et al., "Characterization of AvrHah1, a novel AvrBs3-like effector from Xanthomonas gardneri with vimlence and avimlence activity," New Phytol., 179(2):546-556, Jul. 2008.
Schomack et al., "Expression levels of avrBs3-like genes affect recognition specificity in tomato Bs4—but not in pepper Bs3-mediated perception," Mol. Plant-Microbe Interact, 18(11):1215-1225, Nov. 2005.
Schomack et al., "Gene-for-gene-mediated recognition of nuclear-targeted AvrBs3-like bacterial effector proteins," J. Plant Physiol., 163(3):256-272, Feb. 2006.
Schomack et al., "The tomato resistance protein Bs4 is a predicted non-nuclear TIR-NB-LRR protein that mediates defense responses to severely tmncated derivatives of AvrBs4 and overexpressed AvrBs3," Plant J., 37(1):46-60, Jan. 2004.
Segal et al., "Endonuclease-induced, targeted homologous extrachromosomal recombination in Xenopus oocytes," Proc. Natl. Acad. Sci. USA, 92(3):806-810, Jan. 1995.
Sera, "Inhibition of virus DNA replication by artificial zinc finger proteins," J. Virol., 79(4):2614-2619, Feb. 2005.
Shaul and Galili, "Threonine Overproduction in Transgenic Tobacco Plants Expressing a Mutant Desensitized Aspartate Kinase of *Escherichia coli*," Plant Physiol., 100(3):1157-1163, Nov. 1992.
Shepard and Totten, "Mesophyll cell protoplasts of potato: isolation, proliferation, and plant regeneration," Plant Physiol., 60(2):313-316, Aug. 1977.
Shukla et al., "Precise genome modification in the crop species *Zea mays* using zinc-finger nucleases," Nature, 459(7245):437-441, May 2009.
Simon et al., "Targeting DNA with triplex-forming oligonucleotides to modify gene sequence," Biochimie, 90(8):1109-1116, Aug. 2008.
Skipper, "The holy grail for plant biologists," Nature Reviews Genetics, 10(6):350, Jun. 2009.
Staswick et al., "Identification of the Acidic and Basic Subunit Complexes of Glycinin," J. Biol. Chem., 256(16):8752-8755, Aug. 1981.
Strasser et al., "Generation of glyco-engineered Nicotiana benthamiana for the production of monoclonal antibodies with a homogeneous human-like N-glycan structure," Plant Biotechnology Journal, 6(4):392-402, May 2008.
Studholme et al., "Genome-wide sequencing data reveals vimlence factors implicated in banana *Xanthomonas wilt*," FEMS Microbiol. Lett., 310(2):182-192, Sep. 2010.
Sugio et al., "Two type III effector genes of *Xanthomonas oryzae* pv. *oryzae* control the induction of the host genes OsTFIIAgamma1 and OsTFX1 during bacterial blight of rice," Proc. Natl. Acad. Sci. USA, 104(25):10720-10725, Jun. 2007.
Swamp et al., "An Xanthomonas citri pathogenicity gene, pthA, pleiotropically encodes gratuitous avimlence on nonhosts," Mol. Plant Microbe Interact, 5(3):204-213, May 1992.
Szurek et al., "Eukaryotic features of the Xanthomonas type III effector AvrBs3: protein domains involved in transcriptional activation and the interaction with nuclear import receptors from pepper," Plant J., 26(5):523-534, Jun. 2001.
Szurek et al., "Type III-dependent translocation of the Xanthomonas AvrBs3 protein into the plant cell," Mol. Microbiol., 46(1):13-23, Oct. 2002.
Takenaka et al., "Inhibition of tomato yellow leaf curl virus replication by artificial zinc-finger proteins," Nucl. Acids Symposium Series, 51(1):429-430, Nov. 2007.
Thieme et al., "New type III effectors from *Xanthomonas campestris* pv. *vesicatoria* trigger plant reactions dependent on a conserved N-myristoylation motif," Mol. Plant Microbe Interact, 20(10):1250-1261, Oct. 2007.
Thierry et al., "Cleavage of yeast and bacteriophage T7 genomes at a single site using the rare cutter endonuclease I-Sce I," Nucl. Acids Res., 19(1):189-190, Jan. 1991.
Tovkach et al., "A toolbox and procedural notes for characterizing novel zinc finger nucleases for genome editing in plant cells," Plant J., 57(4):747-757, Feb. 2009.

Townsend et al., "High-frequency modification of plant genes using engineered zinc-finger nucleases," Nature, 459(7245):442-445, May 2009.
Tzfira et al., "Genome modifications in plant cells by custom-made restriction enzymes," Plant Biotechnol J., 10(4):373-389, May 2012.
Urnov et al., "Highly efficient endogenous human gene correction using designed zinc-finger nuclease," Nature, 435(7042):646-651, Jun. 2005.
Van den Ackerveken et al., "Recognition of the bacterial avimlence protein AvrBs3 occurs inside the host plant cell," Cell, 87(7):1307-1316, Dec. 1996.
Van Den Elzen et al., "A chimaeric hygromycin resistance gene as a selectable marker in plant cells," Plant Molecular Biology, 5(5):299-302 Sep. 1985.
Vergunst et al., "VirB/D4-Dependent Protein Translocation from Agrobacterium into Plant Cells," Science, 290(5493):979-982, Nov. 2000.
Voytas and Joung, "Plant science. DNA binding made easy," Science, 326(5959):1491-1492, Dec. 2009.
Wah et al., "Structure of FokI has implications for DNA cleavage," Proc. Natl. Acad. Sci. USA, 95(18):10564-10569, Sep. 1998.
Wah et al., "Structure of the Multimodular Endonuclease FokI Bound to DNA," Nature, 388(3):97-100, Jul. 1997.
Wang et al., "Characterization of low-molecular-weight glutenin subunit Glu-B3 genes and development of STS markers in common wheat (*Triticumaestivum* L.)," Theoretical and Applied Genetics, 118(3):525-39, Feb. 2009.
Wang et al., "Chemically regulated expression systems and their applications in transgenic plants," Transgenic Res., 12(5):529-540, Oct. 2003.
Weber et al., "The type III-dependent Hrp pilus is required for productive interaction of *Xanthomonas campestris* pv. *vesicatoria* with pepper host plants," J. Bacteriol., 187(7):2458-2468, Apr. 2005.
White and Yang, "Host and pathogen factors controlling the rice/ *Xanthomonas oryzae* interaction," Plant Physiol., 150(4):1677-1686, Aug. 2009.
White et al., "The type III effectors of Xanthomonas," Mol. Plant. Pathol., 10(6):749-766, Nov. 2009.
Wright et al., "High-frequency homologous recombination in plants mediated by zinc-finger nucleases," Plant J., 44(4):693-705, Nov. 2005.
Yang and White, "Diverse members of the AvrBs3/Pth A family of type III effectors are major virulence determinants in bacterial blight disease of rice," Mol. Plant Microbe Interact, 17(11):1192-1200, Nov. 2004.
Yang et al., "Avoidance of host recognition by alterations in the repetitive and C-terminal regions of AvrXa7, a type III effector of *Xanthomonas oryzae* pv. *oryzae*," Mol. Plant Microbe Interact, 18(2):142-149, Feb. 2005.
Yang et al., "Os8N3 is a host disease-susceptibility gene for bacterial blight of rice," Proc. Natl. Acad. Sci. USA, 103(27):10503-10508, Jul. 2006.
Yang et al., "The virulence factor AvrXa7 of *Xanthomonas oryzae* pv. *oryzae* is a type III secretion pathway-dependent nuclear-localized double-stranded DNA-binding protein," Proc. Natl. Acad. Sci. USA, 97(17): 9807-9812, Aug. 2000.
Yoo et al., "*Arabidopsis mesophyll* protoplasts: a versatile cell system for transient gene expression analysis," Nature Protocols, 2(7):1565-1572, Jul. 2007.
Yuan et al., "Characterization of Xanthomonas oryzae-responsive cis-acting element in the promoter of rice race-specific susceptibility gene Xa13," Mol. Plant, 4(2):300-309, Mar. 2011.
Zeh et al., "Antisense Inhibition of Threonine Synthase Leads to High Methionine Content in Transgenic Potato Plants," Plant Physiol., 127(3):792-802, Nov. 2001.
Zhang et al., "Efficient construction of sequence-specific TAL effectors for modulating mammalian transcription.," Nat. Biotechnol., 29(2):149-153, Feb. 2011.
Zhang et al., "High frequency targeted mutagenesis in *Arabidopsis thaliana* using zinc finger nucleases," Proc. Natl. Acad. Sci. USA, 107(26):12028-12033, Jun. 2010.

(56) References Cited

OTHER PUBLICATIONS

Zhang et al., "RNAi effects on regulation of endogenous acid invertase activity in potato (*Solanum tuberosum* L.) tubers," Chin. J. Agric. Biotechnol., 5(2):107-112, Aug. 2008.
Zhu et al., "Increased Lysine Synthesis Coupled With a Knockout of Its Catabolism Synergistically Boosts Lysine Content and Also Transregulates the Metabolism of Other Amino Acids in *Arabidopsis* Seeds," Plant Cell, 15(4):845-853, Apr. 2003.
Zhu et al., "The C terminus of AvrXa10 can be replaced by the transcriptional activation domain of VP16 from the herpes simplex virus," Plant Cell, 11(9):1665-1674, Sep. 1999.
Zhu et al., "AvrXa10 Contains an Acidic Transcriptional Activation Domain in the Functionally Conserved C Terminus," Molecular Plant-Microbe Interactions, 11(8): 824-832, Aug. 1998.
Zhu et al., "The rsma-like gene rsmA(XOO) of *Xanthomonas oryzae* pv. *oryzae* regulates bacterial virulence and production of diffusible signal factor," Mol. Plant Pathol., 12(3):227-237, Apr. 2011.
Zou et al., "Identification of an avirulence gene, avrxa5, from the rice pathogen *Xanthomonas oryzae* pv. *oryzae*," Sci. China Life Sci., 53(12):1440-1449, Dec. 2010.
Zrenner et al., "Soluble acid intervase determines the hexos-to sucrose ratio in cold-stored potato tubers," Planta, 198(2):246-252, Feb. 1996.
Zuo and Chua, "Chemical-inducible systems for regulated expression of plant genes," Curr. Opin. Biotechnol., 11(2):146-151, Apr. 2000.
Zuo et al., "Technical advance: An estrogen receptor-based transactivator XVE mediates highly inducible gene expression in transgenic plants," Plant J., 24(2):265-273, Oct. 2000.

* cited by examiner

FIG. 2

>Gy4 genomic sequence; Glyma10g04280
ATGGGGAAGCCCTTCACTCTCTCTTCTTCCCTTTGCTTGCTGCTACTCTTGTCGAGTGCATGCTTTGCTATTAGCTCCAGCAAGCTCAACGAG
TGCCAACTCAACAACCTCAACGCGTTGGAACCCGACCACCCTCGAGTCCGAAGGTGGTTGATTCAAACATGGAACTCTCAACACCCTGAG
CTGAAATGCGCCGGTGTCACTGTTTCCAAACTCACCCTCAACGGCCTCCACTTGCCATCTTACTCACCTTATCCCGATGATCATC
ATCGCCCAAGtaatcatatataaggagtgcttctaacacacatcagaaagagtatcaccagcatttctcagtgtatattaatccattgt
cacacttgttcaaatttcaacatcacattactagatcatttactaaagataatgattaagtaaatagtatctctatagtaaatttt
acatgattattaactacaaattattattatataaaatgtgattgtttgtttgtgatgattgatgtacagGAAAGAGCACTTGGAGTTGCAATTCCAG
tcaactaagatatctgattaaataaaatgtgattgttttgttgtgatgattgatgtacagGAAAGAGCACTTGGAGTTGCAATTCCAG
GATGTCCTGAGACGTTTGAGGAGGACGTACTCGTGATTCCTCCTGGTGTTCCTTACTGACCTATAACACTGGCGATGAACCAGTTGTTGCCATCA
TTCGTCACTTCAATGAAGAGACCTCTAACTTCAATAACCAGCTTGATCAAACCCCTAGGtaattatcaattcatttactattaacaaaaccatg
GTCTTCTTGACACCTCTAACTTCAATAACCAGCTTGATCAAACCCCTAGGtaattatcaattcatttactattaacaaaaccatg
ttctcctcacttgttaattttttcactttcagGTATTTACCTTGCTGGGAACCCAGATATAGAGTACCAGAGACCATGCAACAACAAC
AGCAGAAAGTCATGGTGGACGCAGGGCAACACCAGCAGGAGGAAGAGAAGGTGGCAGCGTGCTCAGTGGCTTCAGCAAACACT
TCTTGGCACAATCCTTCAACACCAAGTGGCAAGAACAACAAGATGGCTGAGAAACTTCAGTCTCCAGACGACATAGCTGAGAAGATGAAGATGAAGACGAGATCAGTGGAAGAG
GTCTCAGCGTTATCAGCCCCAAGTGGCAAGAACAACAAGATGGCTGAGAAGCGTGAACAAGACCAGACAAGACCAGAACCACGGAAAGCGTGAACAAGACCAGACAAGACCAGAACCACGGAAAGCGTGAACAAGACCAGACAAGACCAGAACCACG
CTCCTCGCCGACCAAGCCATGGAAAGCGTGAACAAGACCAGACAAGACCAGAACCACGTGAAAGAGAACCGTGAAAGAGGATGCCGAGAACAAGAACCGTCGAGACGCCCGAATGGAGATCAACCTGTCGTCCTAGTCGACCAAGCAAGGAA
AGCCGTGAACAAGACCAGACAAGACCAGAACCACGTGAAAGAGGATGCCGAGAACAAGAACCGTCGAGACGCCCGAATGGAGATCAACCTGTCGTCCTAGTCGACCAAGCAAGGAA
CCAGAAGACCTAGACAAGAAGAACCACGTGAAAGAGAACCGTGAAAGAGGATGCCGAGAACAAGAACCGGGTTGAGGAAAATATCTGCACCTTGAAGCTTCACGAGA
ACATTGCTGCTGCCCTTCGCGCTGACTTCTGTCCTCTACAAGtatgtaattcacctcattcatattcttgataatcaacatgaaactaatacgtac
TCCAACTCAGTGCCCAATATGTTGTCCTCTACAAGtatgtaattcacctcattcatattcttgataatcaacatgaaactaatacgtac
atacttacacatctaccagtaattttttccgtggatatataatatttagaagacatataaaatgtcagtaagtatgtttgtaggtgattcttta
gggaaaatctttatgtcataaatcatttgatatgggtaattctttagtagttgaactgtaatgtattataattgtcattgatttt
aatgtcattaaaatatcatttgatatgggtaattctttagtagttgaactgtaatgtattataattgtcattgatttt
tgagttactttaacatgtcaatgaagactttattgataataattagttagttactttgttggttctactcttaataaaaataaaaa
tattggtgtaatatatataataatgatgatgatatcgtaacacatgttattatatccatgcagAATGGAATTTACTCTCCACATT
GGAATCTGAATGCAAACAGTTGCTAGTCTATGTGACTCGAGGACAAGAACTTCGTGGTGGCGAGCAAGCCGGAACAAGGATTCGAATACATAGTATTCAAGA
AGCTTAGGAGGGACAATTGCTCACTAGTCTACTTGAAGGATGTGTTTAGGGCAATTCCCTGAGTCTCAACCAAGGCTCCAACAAGGCTCAACAAGGCCCGTGTTAAAGTCGCATAA
AAGTGTCTGAGCTTAAGTAATGAAGGAAATTGGGGTCTCAACCCTGAGTCTCAACAAGGCTCCAACAAGGCCCGTGTTAAAGTCGCATAA (SEQ ID NO:1)

FIG. 3A

>Gy4 exon 1 sequence
ATGGGGAAGCCCTTCACTCTCTCCTTCTTCCCTTGCTGCTACTCTTGTCGAGTGCATGCTTTGCTATTAGCTCCAGCAAGCTCAACGAGTGCCAACTCAACAACC
TCAACGCGTTGGAACCCGACCACCGCGTTGAGTGCATGTTGATTCAAACATGGAACTCAACACCCTGAGCTGAAATGCGCCGGTGTCACTGTTTCCAAACT
CACCCTCAACGCCAATGGCCTCCACTTGCCATCTACTGCCACCTACTCACCTACTCCCGATGATCATCGCCCAAG (SEQ ID NO:2)

>Frame -1
WGSPSLSLFLPFACYSCRVHALLLAPASSTSANSTTSTRWNPTTALSPKVV*FKHGTLNTLS*NAPVSLFPNSPSTAMASTCHLTHLIPG*SSSPK (SEQ ID
NOS:3-6)

>Frame -2
GEALHSLSFFPLLATLVECMLCY*LQQAQRVPTQQPQRVGTRPPR*VRRWFDSNMELSTP*AEMRRCHCFQTHPQPQWPPLAILLTLSPDDHHRP (SEQ ID
NOS:7-10)

>Frame -3
GKPFTLSLSSICLLLLSSACFAISSSKLNECQLNNLNALEPDHRVESEGGLIQTWNSQHPELKCAGVTVSKLTLNRNGLHLPSYSPYPRMIIAQ (SEQ ID
NO:11)

>Gy4 exon 2 sequence
GGAAAGGAGCACTTGGAGTTGCAATTCCAGGATGCCTGAGACGTTGAGGAGCCACAAGAACCAAGTCGCAGAAGAGCTCAAGTCGCAGAAGCAGCTACAGA
CAGTCACCAGAGATTCGTCACTCAGTCGTCACTGCCTGTGATTCCTCCTGGTGTTCCTTACTGGACCTATAACACTGGCGATGAACCAGTTGTTGCCATCAGT
CTTCTTGACACCTCAACTTCAATAACCAGCTGATCAAACCCCTAGG (SEQ ID NO:12)

>Frame -1
KEHLELQFQDVLRRLRSHKNNQTEEAQGRRSSSYRTVTRRFVTSMKETYS*FLLVFLTGPITLAMNQLLPSVFLTPLTSITSLIKPL
(SEQ ID NOS:13-14)

>Frame -2
ERSTWSCNSRMS*DV*GATRTIKQKRLKVAEAAATGQSPEDSSLQ*RRRTRDSSWCSLLDL*HWR*TSCCHQSS*HL*LQ*PA*SNP*
(includes SEQ ID NOS:15-18)

>Frame -3
KGALGVAIPGCPETFEEPQEQSNRRGSRSQKQLQDSHQKIRHFNEGDVLVIPPGVPYWTYNTGDEPVVAISLLDTSNFNNQLDQTPR
(SEQ ID NO:19)

FIG. 3B

>Gy4 exon 3 sequence
GTATTTACCTGCTGGAACCCAGATATAGAGTACCCAGAGACACCATGCAACACAACACAGCAGAAAAGTCATGTGACGCAGGGCAACACCAGCAGAGGAAGAGG
AAGAAGGTGCCAGCGCGTGCTCAGTGGCTTCAGCCGTTATCAGCCCAAGTGGCAGGACGAGGAAGCCGCGAATGAACAACCTCGTCCTAGTGACGAAGGACGAGATGAGAAGATGAGAAGAAGATGATGAAGAAGATGATGAAGAAGTCCCTCCACCCTCT
CGTGACAGTGCGAAGGAGGTCTCAGCGTTATCAGCCCAAGTGGCAGGACGAGGACGAGAGCCGCGAATGAACAACCTCGTCCTAGTGACGAAGACCTGACCAGACCAGAACCGTGACCCTGAACAGACCAGGACG
CGCCGACCAAGCCATGGAAGATGAAGATCAACCTCGCAGAGATGAAGATCGCGAATGAACAACCTCGTCCTAGTGACGAAGACCTGACCAGACCAGAACCGTGACCCTGAACAGACCAGGACG
AGGACGAAGATGAAGATGAAGATATCTGCACCTTGAAGCTTCACGAGAACATTGCTCGCCCTTCACGCGCTGACTTCTACAACCCTAAAGCTGTGTCGCATTAGTACCCTCAACAGCCTC
AAACGGGGTTGAGGAAAATATCTCCGCCAATTCCAACTCAGTGCCCAATATGTTGTCCTCTACAAG (SEQ ID NO:20)
ACCCTCCCAGCCCTCCGCCAATTCCAACTCAGTGCCCAATATGTTGTCCTCTACAAG (SEQ ID NO:20)

>Frame -1
YFTLLGTQI*STQRPCNNNNSRKVMVDASRGNTSRRKRKKVAACSVASANTSWHNPSTPTRT*LRNFSLQTTKGSRS*QWKEVSALSAPSGKNNKMKMKTKMMKMNKFPLTLL
ADQAMESVNKTRTRTKMKINLVLVDQAKESVNKTRTRTRTKMKMKINLARAANGDRKRHNPEDLDKKNHVKEDARQETGLRKISAP*SFTRTLLALHALTSTTLKLVALVPSTAS
PSQPSANSNSVPNMLSST (SEQ ID NOS:21-25)

>Frame -2
ILPCWEPRIYRVPRDHATTTAEKSWTQAGATPAGGRGRRWQRAQWLQQTLLGTILQHQRGHS*ETSVSRRRKEADRDSGRRSQRYQPQVARTTR*R*R*RRR*R*TNSLSPSS
PTKPWKA*TRRGRGRR*R*TSS*STKPRKA*TRPGPGRGRR*R*RSTSQEPRMEIEKDTTQKT*TRRTT*KRMRDKKRG*GKYLHLEASREHCSPFTR*LLQP*SWSH*YPQQPH
PPSPPPIPTQCPICCPLQ (includes SEQ ID NOS:26-38)

>Frame -3
FYLAGNPDIEYPETMQQQQQKSHGGRKQGQHQEEEEGGSVLSGFSKHFLAQSFNTNEDIAEKLQSPDDERKQIVTVEGGLSVISPKWQEQQDEDEDEDEDEDEQIPSHPPR
RPSHGKREQDEDEDEDKPRPSRPSQGKREQDQDEDEDEDQPRKSREWRSKKTQPRRPRQEEPRERGCETRNGVEENICTLKLHENIARPSRADFYNPKAGRISTLNSLT
LPALRQFQLSAQYVVLYK (SEQ ID NO:39)

>Gy4 exon 4 sequence
AATGGAATTACTCTCCACATTGGAATCTGAATCGAAACAGTGTGATCTATGTGACTCGAGGACAAGGAGAAAGGTTAGAGTTGTGAACTGCCAAGGAATGCAGTCGAGCAGTGTTCGACGGTG
AGCTTAGGAGGGGACAATTGCTGCTGGTAGGCACTGCTGGTGGTGCCGGAGCAGCCGGAGACAACAAGGATTCGAATACATAGTATTCAAGACACATAGTATTCAAGACACCACACGCAGTCACTAG
CTACTTGAAGGATGGTGTTAGGGCAATTCCCCAGAAGTTCTTGCCAATTCTTACAACCTTCGACAGAGTCAAGTGTCGAGCTTAAGTATGAAGGAAATTGGGGTCCTTGGTC
AACCCTGAGTCTCAACAAGCTCACCCCGTGTAAAGTCGCATAA (SEQ ID NO:40)

>Frame -1
MEFTLHIGT*MQTV*SM*LEDKERLEL*TAKGMQCSTVSLGGDNCWWYHRTSWWRSKPENKDSNT*YSRHTTQSLAT*RMCLGQFPQRFLPILTTFDRVKCLSLSMKEIGVLWS
TLSLNKAHPVLKSH (includes SEQ ID NOS:41-46)

>Frame -2
WNLLSTLESECKQCDLCDSRTRKG*SCELPRECSVRR*A*EGTIAGGTTELRGGASRRTRIRIHSIQDTPQRSH*LLEGCV*GNSLRGSCPFLQPSTESSV*A*V*RKLGSFGQ
P*VSTRLTPC*SRI (includes SEQ ID NOS:47-53)

>Frame -3
GIYSPHWNLNANSVIYVTRGQGKVRVNCQGNAVFDGELRRGQLLVVPQNFVVAEQAGEQGFEYIVFKTHHNAVTSYLKDVFRAIPSEVLAHSYNLRQSQVSELKYEGNWGPLVN
PESQQGSPRVKVA* (SEQ ID NO:54)

FIG. 4

>Gy4 wild type
MGKPFTLSLSSLCLLLLSSACFAISSSKLN
ECQLNNLNALEPDHRVESEGGLIQTWNSQH
PELKCAGVTVSKLTLNRNGLHSPSYSPYPR
MIIAQGKGALGVAIPGCPETFEEPQEQSN
RRGSRSQKQQLQDSHQKIRHFNEGDVLVIP
PSVPYWTYNTGDEPVVAISLLDTSNFNNQL
DQTPRVFYLAGNPDIEYPETMQQQQQKSH
GGRKQGQHQQEEEEGGSVLSGFSKHFLAQ
SFNTNEDIAEKLESPDDERKQIVTVEGGLS
VISPKWQEQQDEDEDEDEDDEDEQIPSHPP
RRPSHGKREQDEDEDEDEDKPRPSRPSQGK
RNKTGQDEDEDEDEDQPRKSREWRSKKTQP
RRPRQEEPRERGCETRNGVEENICTLKLHE
NIARPSRADFYNPKAGRISTLNSLTLPALR
QFQLSAQYVVLYKNGIYSPHWNLNANSVIY
VTRGQGKVRVVNCQGNAVFDGELRRGQLLV
VPQNFVVAEQAGEQGFEYIVFKTHHNAVTS
YLKDVFRAIPSEVLAHSYNLRQSQVSELKY
EGNWGPLVNPESQQGSPRVKVA*
(SEQ ID NO:55)

Methionine and cysteine content: 1.5%
Lysine content: 5.0%

>Gy4; -1 frameshift within
exon 3; early stop codon at
the end of exon 3
MGKPFTLSLSSLCLLLLSSACFAISSSKLN
ECQLNNLNALEPDHRVESEGGLIQTWNSQH
PELKCAGVTVSKLTLNRNGLHSPSYSPYPR
MIIAQGKGALGVAIPGCPETFEEPQEQSN
RRGSRSQKQQLQDSHQKIRHFNEGDVLVIP
PSVPYWTYNTGDEPVVAISLLDTSNFNNQL
DQTPRVFYLAGNPDIEYPETMQQQQQKSH
GGRKQGQHQQEEEEGGSVLSGFSKHFLAQ
SFNTNEDIAEKLESPDDERKQIQWKEVSAL
SAPSGKNNKMKMKMKTKMKMKNKFPLTLLA
DQAMESVNKTRTRTKMKINLVLVDQAKESV
NKTRTRTRTKMKINLARAANGDRKRHNP
EDLDKKNHVKEDARQETGLRKISAP*
(SEQ ID NO:56)

Methionine and cysteine content: 4.1%
Lysine content: 9.1%

FIG. 6

>Gy4 wild type
MGKPFTLSLSSLCLLLLSSACFAISSSKLNE
CQLNNLNALEPDHRVESEGGLIQTWNSQHPE
LKCAGVTVSKLTLNRNGLHSPSYSPYPRMII
IAQGKGALGVAIPGCPETFEEPQEQSNRRGS
RSQKQQLQDSHQKIRHFNEGDVLVIPPSVPY
WTYNTGDEPVVAISLLDTSNFNNQLDQTPRV
FYLAGNPDIEYPETMQQQQQKSHGGRKQGQ
HQQEEEEGGSVLSGFSKHFLAQSFNTNEDI
AEKLESPDDERKQIVTVEGGLSVISPKWQEQ
QDEDEDEDEDEDEQIPSHPPRRPSHGKREQ
DEDEDEDEDKPRPSRPSQGKRNKTGQDEDED
EDEDQPRKSREWRSKKTQPRRPRQEEPRERG
CETRNGVEENICTLKLHENIARPSRADFYNP
KAGRISTLNSLTLPALRQFQLSAQYVVLYKN
GIYSPHWNLNANSVIYVTRGQGKVRVVNCQG
NAVFDGELRRGQLLVVPQNFVVAEQAGEQGF
EYIVFKTHHNAVTSYLKDVFRAIPSEVLAHS
YNLRQSQVSELKYEGNWGPLVNPESQQGSPR
VKVA* (SEQ ID NO: 55)

Methionine and cysteine content: 1.5%
Lysine content: 5%

>Gy4; -1 frameshift within exon 3; frameshift at the end of exon 3 to restore original frame
MGKPFTLSLSSLCLLLLSSACFAISSSKLNE
CQLNNLNALEPDHRVESEGGLIQTWNSQHPE
LKCAGVTVSKLTLNRNGLHSPSYSPYPRMII
IAQGKGALGVAIPGCPETFEEPQEQSNRRGS
RSQKQQLQDSHQKIRHFNEGDVLVIPPSVPY
WTYNTGDEPVVAISLLDTSNFNNQLDQTPRV
FYLAGNPDIEYPETMQQQQQKSHGGRKQGQ
HQQEEEEGGSVLSGFSKHFLAQSFNTNEDI
AEKLESPDDERKQIQWKEVSALSAPSGKNNK
MKMKMKTKMMKMNKFPLTLLADQAMESVNKT
RTRTKMKINLVLVDQAKESVNKTRTRTRTKM
KMKINLARKSREWRSKKTQPRRPRQEEPRER
GCETRNGVEENICTLKLHENIARPSRADFYN
PKAGRISTLNSLTLPALRQFQLSAQYVVLYK
NGIYSPHWNLNANSVIYVTRGQGKVRVVNCQ
GNAVFDGELRRGQLLVVPQNFVVAEQAGEQG
FEYIVFKTHHNAVTSYLKDVFRAIPSEVLAH
SYNLRQSQVSELKYEGNWGPLVNPESQQGSP
RVKVA* (SEQ ID NO: 57)

Methionine and cysteine content: 3.3%
Lysine content: 7.2%

FIG. 8

>Triticum aestivum clone 1-8 alpha-gliadin (gli-2) gene, complete cds; GeneBank JN831386.1
ATGAAGACCTTTCTCATCCTTGCCCTCCGTGCTATTGTAGCAACCACCGCCACAATTGCAGTTAGAGTTCCAGTGCCACAATTGCAGCCACAA
ATCCATCTCAGCAGCAACCACAAAAGCAAGTTCCATTGTAGCAACAACAATTCCAGGGCAGCAACAACCATTTCCACCACAACAGCATA
TCCGCAGTGCAACCATTTCCATCACAACAACCATATATGCAGTGCAACCATTCCGCAGCCGCAACTACCATATCCGAGCCGCAACTACCA
TATCCGCAGCCGCAGCCAACCATTCGACCACAACAACAACAACAACAACAGTCCACCAACCGCCAACTATTCGCAACCACAACCATTCGCAGCAGCAGC
AGCAGCAGCAGCAGCAACAACAACAACAACAACAGATCCTTCAACAAATTTGCAACAACAACTGATTCCATGCAGGGATGTTGTATTGCAACA
ACACAGCAGCATAGCGCATGGAAGCTCACAAGTTTGCAACAAGTACTTACCAGCTGGTGCAACAATTGTGTTGTCAGCAGCTATGGCAGATCCCC
GAGCAGTCGCGGTGCCAAGCCATCCACAATGTTGTTCATCCACACAGTCTCCAACAACAATATCATCAGGCAGGCTCCTTCCAGCCATCTCAGCAAAACCCACAGGC
AACAACCGTTGAGCCAGGTCTGCTTCCAACAGTCTCCAACAACTGCCCCAGTTTGAGGAAATAAGGAACCTAGCGCTAGAGACGCTACCTGCAATGTGCAATGTCTATATC
CCTCCATATTGCACCATTGCTCCAGTTGCATCTTCGGTACTAACTGA (SEQ ID NO:58)

>Frame -1
*RPFSSLPSVLL*QPPPQLQLEFQCHNCSHKIHLSSNHKSKFHWYNNNNFQGSNNHFHHNSHIRSCNHFHHNNHICSCNHFRSRNYHIRSRNYH
IRSRNHFDHNNHIHNRNHSIRNHNNQSRSSSSSSSNNNNNNRSFNKFCNNN*FHAGMLYCNNTA*RMEAHKFCNKVLTSWCNNCVVSSYGRSP
SSRGAKPSTMLFMLLFCINNNNNNNNNNNNR*ARSASNSLNNNIHQARAPSSHLSKTHRPRALSSLNNCPSLRK*GT*R*RRYLQCAMSIS
LHIAPLLQLASSVLT (includes SEQ ID NOS:59-64)

>Frame -2
EDLSHPCPPCYCSNHRHNCS*SSSATIAATKSISAATTKASSIGTTTTISRAATTISTTTAISAAATISITTTIYAAATISAAATTISAAATTI
SAAATISTTTIISTTATTVFATTTTNLAAAAAAATTTTTDPSTNFATTTDSMQGCCIATTQHSAWKLTSFATKYLPAGATIVLSAAMADPR
AVAVPSHPQCCSCYYSASTTTTTTTTTTVEPGLLPTVSTTISIRPGLLPAISAKPTGPGLCPASTTAPV*GNKEPSARDATCNVQCLYP
SILHHCSSWHLRY*L (includes SEQ ID NOS:65-67; HIGH THREONINE CONTENT)

>Frame -3
MKTFLILALRAIVATTATIAVRVPVPQLQPQNPSQQQPQKQVPLVQQQQFPPGQQQFFPPQQPYPQLQPFPQQPLPYPQPQLP
YPQPQPFRPQQSYPQPQPQYSQPQQPISQQQQQQQQQQQQQILQQILQQQLIPCRDVVLQQHSIAHGSSQVLQQSTYQLVQQLCCQQLMQIP
EQSRCQAIHNVVHAIILHQQQQQQQQQQQPLSQVCFQQSQQQYPSGQGSFQPSQQNPQAQGSVQPQQLPQFEEIRNLALETLPAMCNVYI
PPYCTIAPVGIFGTN* (SEQ ID NO:68)

FIG. 9

>Triticum aestivum clone 1-8 alpha-gliadin (gli-2) gene, translated cds; GeneBank JN831386.1
MKTFLILALRAIVATTATIAVRVPVPQL
QPQNPSQQQPQKQVPLVQQQQFPGQQQP
FPPQQPYPQLQPFPSQQPYMQLQPFPQP
QLPYPQPQLPYPQPQPFRPQQSYPQPQP
QYSQPQQPISQQQQQQQQQQQILQ
QILQQQLIPCRDVVLQQHSIAHGSSQVL
QQSTYQLVQQLCCQQLWQIPEQSRCQAI
HNVHAIILHQQQQQQQQQQPLS
QVCFQQSQQQYPSGQGSFQPSQQNPQAQ
GSVQPQQLPQFEEIRNLALETLPAMCNV
YIPPYCTIAPVGIFGTN* (SEQ ID NO:68)

Threonine content: 2.6%
Lysine content: 0.7%

>Triticum aestivum clone 1-8 alpha-gliadin (gli-2) gene, translated cds; -2 frameshift mutation at the begining of the coding sequence
MKTFLILALRAIVATTATIAVRVPVSSS
ATIAATKSISAATTKASSIGTTTTISRA
ATISTTTAISAAATISITTTTIYAAATI
ATTISTTTAISAAATISITTTTIYAAATI
SAAATISAAATTISAAATISTTTIIST
TATTVFATTTTNLAAAAAAATTTTTT
DPSTNFATTTDSMQGCCIATTQHSAWKL
TSFATKYLPAGATIVLSAAMADPRAVAV
PSHPQCCSCYYSASTTTTTTTTTTTTT
TVEPGLLPTVSTTISIRPGLLPAISAKP
TGPGLCPASTTAPV* (SEQ ID NO:69)

Threonine content: 27.8%
Lysine content: 2.3%

FIG. 10A

>Triticum aestivum Glu-1D-1d gene for high molecular weight glutenin subunit 5; GeneBank X12928.5

ATGGCTAAGCGGTTAGTCCTCTTTGTGGCGGTAGTCGTCGCCCTCGTCGTGCTGGCTCTCACCGTCGCTGAAGGTGAGCCTCGAGCAACTACAGTGTGAGCGCGAGCTCCAG
GAGCGCGAGCTCAAGGCGTGCATGCCAGCAGTCATGGACCAACAGTCCGAGACATTAGCCCGGAGTGCCACCCGTCGTGCAGCCCGTCGTGCGGACAATACGAGCAGCAAATCGTG
GTGCCGCCCAAGGCGGATCTTTCTACTATCCAGGCCAAGTCCTGCACTACTAAAAAGGTATTACCAAGTGTAACT
TGTCCGCAGCAGTTCATACTATCCAGGCCAACCAAGTACTACCCAACTTCTCCGACAGGTACTACCCAACTTCTCCGCAACAGCCAGGA
CAATGGCAACAACCGGAACCAGGGCAACCAGGTACTACCCAACTTCTCCGACAGTCAGGACAATTCAACAACCAGCAAGGGCAACAAGGTCAG
CAGCCAGGACAAGGGCAACAAGGTACTACCCAACCAGGACAAGGGCAACAAGGTCAACAACCAGGACAAGGGCAACAAGGTCAGCAGCCAGGACAAGCGCAACAAGGT
CAACAGCCAGGACAAGGGCAACAAGGTCAACAACCAGGACAAGGGCAACAACCAGGACAAGGGCAACAAGGTCAGCAGGTACCCAACTTCTCGCAGCAACCA
TACTACCCAACTTCTCTGCAACAGTCGGGACAGCAATTGCAACAACCAGGACAAGGGCAACAACCAGCTAGGACAAGGGCAACAAGGCAACCAGGACAAGGG
GAACAAGGGCAGCAGCCAGGACAAGGGCAACAACCAGGACAAGGGCAACAAGGTCAGCAGGTACTCAGCAGGACAACAACCAGGACAACAAGGCCAGCAGCCAGGACAAGGG
CAGCAAGGGCAACAAGGCAGCAGCCAGGACAAGGGCAACAAGGTCAGCAGGTACTACCCAACTTCTCCGCAGGGCAAAAAGACAGCAACCAGGACAAGGT
CAACAGCCAGGACAAGGGCAACAAGGTCAGCAGCCAGGACAAGGGCAACAACCAGGACAAGGGCAACAAGGTCAGCAGGTACTACCCAACTTCTCTGACCAAGTGCAACAAGGG
CAACAAGGGCAGCAGCCAGGACAAGGGCAACAACCAGGACAAGGGCAACAACCAGGACAAGGGCAACAAGGTCAGCAGGTACCCGTTGCAGCACCAGGACAACAAGGGCAGCGGCCA
GCACAAGGGCAGCAAGGTCAGCAGGACAAGGGCAACAACCAGGACAAGGGCAACAAGGTCAACAAGGCCAGCAACAAGGGCAGCAACAGGGCCATGGCAGCAGCCATGTACTACCA
ACTTCTCGCAGAGTCTCGCAACAACCAGGACAAGGGCAACAAGGTCAACAAGGGCAGCAACAACCAGGACAAGGTACCCGTTGCAGCACCAGGACAAGGG
TACTACCCAACTTCTCTGCAACAACCAGGACAAGCGTGCAACAACCAGCAATCATTGTACTACCAACAACCAGGACAACAGCCAGCAACAATTGGACAACAAGGTCAGGACAAGG
CAACGGCCAGGACAATGGCTGCAACAACCAGGACAAGGGCAACAAGGGCAACAAGGTACCCGCAACAACTAGGACAACAACCGCAACAACCAGGACAAGG
CTAAAGGTGGCAAAGCGCACAGCTCGCCGGCACAGTGTGCCGGCTGCCGGATGTGCGGCGACGCATTGTCGGCGACGCAGTGA (SEQ ID NO:70)

FIG. 10B

```
>Frame -1
WLSG*SSLWR*SSPSWLSPSLKVRPLSNYSVSASSRSSRSASSRHASRSWTNSSETLAPSATPSSSARSRDNTSSKSWCRPRADLSTPARPRHRSNSNNVYFGEYLHY*KGITQV*L
VRSRFHTIQAKLLRNGQDKVSSQDKDNKGTTQLLRSSQDNGNNRNKGNQGTTQLLRSSQDNCNNQHKGSNQDKGNKVSSQDKGNQGTTQLLRSCSQDNCNNQHKGNKGSNQDKRNKV
NSQDKGNNQDKDNKVNSQDKGNKVSSSDKDNKGTTQLLCNSRDKGNQGTTQLLCSS*DKGNQGTTQLLRSNQDKGSSQDNCNNQHKGSNQDKGNKVSSQDNCNNQHKGKKDSNQDKV
SNRDKGNQGTTQLLRSSQDKGNQGTTQLLRSSQHNRSNQDKGNKVSR*DKGNKLSSQDKGNRDKGSQGTTQLLRSSQDKGNQGTT*LLRSSQDKGSSQDNCNNQHKGSNQHCNKGSGQ
NSQGKGNKVSSQDKGNKVSNRGKGSQGTTQLLRSSQDKGNKVSS*DKGNKVSSQDKGNQDTTQLLRCSQDKGNQDTTQLLRNSQDKGNNQHKGNKGSN*HKGNKGSNQHKCNKGSGQ
HKGNKVSSQDKGNKVSS*DKGNKVSSQDKGNNQHKGNKVSSQDKGNRDKGSHGTTQLLRRSQDKGSNRDKGSNQDNGNNQDKGNQGTT*LLRCS*DKGNKG
TTQLLCNNQDKGSNQDNGNNRDKGNIGTTQLLRSCQDKGNGQDNGCNQDKGNKGTTQLLRNSQDKGNN*DNGCNQDKGSNQDKGNKATTAHTMLAWSTRRPA
*RWQRRSSSRHSCRQCAGWRAATHCRPAS   (SEQ ID NOS:71-84; HIGH LYSINE CONTENT)

>Frame -2
G*AVSPLCGGSRRPRGSHRR*R*GL*ATTV*ARAPGAPGARAQGMPAGHGPTAPRH*PRVPPRRQPGRGTIRAANRGAAQGRIFLPRRDHATAATPTTYILGNTCTTKKVLPKCNL
SAAGFILSRPSFSATARTRSTARTRATT RTTRVLPNFSATARTRTTRVLPNFSAARTRTRATKVLPNFSATRVTGTRATRVLPNFSATVGTRATRVLPNFSAARTRAIRVLPNFSAARTIATTSTRATRTRATRSAARTRTRATRSAARTRAIRVLPNFFAAAARTIATTSTRATRTRATRSAATRS
TARTRATTRTRTTRSTARTRATTRTRATRSAAVRTRAIRVLPNFSATVGTRATRVLPNFSATVGTRATRSAGRTRATSSAARTRAATGTRAAVRTRATRVLPNFSAAVRTRATRVLPNFSVAARTRATRTRATRILPNFSVAARTRATRSAARTRATRSAARTRATRSAGVRTRATARTMATTRTRATRVLPNFSAGVRTRATARTMATTRTRATRVLPNFSVAARTRATRV
ATGTRATRSAARTRATRSATGARAARVLPNFSAAIRTRATARTMATTRTRATMATTRTRATRSAARTRATRSAARTRATRSAARTRATRSAARTRATRTATTSTRAATRTRATRSAATRTRATRSAARTRAATISTRAKRTATRTRS
TARARATRSAARTRATRSATGARAARVLPNFSAAIRTRATARTMATTRTRATAIRTRATSTRATRSAARTRATRSAARTRATRSAARTRATRSAATRTRATRTAIRTRATRTAARTRTRATRAATISTRAAAS
TRATRSAARTRATRTRAATRTMATIGTRATLVLPNFSAAVRTRATARTMAATRTRATRVLPNFSATDRTRAAIRTRATRLLQLIPC*RGAPGGQP
LPNFSATTRTRAATRTMATIGTRATLVLPNFSAAVRTRATARTMAATRTRATRVLPNFSATDRTRAAIRTRATRLLQLIPC*RGAPGGQP
KGGKGAAARGTAAGNVPAGGRRRIVGQPV   (includes SEQ ID NOS:85-89; HIGH THREONINE CONTENT)

>Frame -3
MAKRLVLFVAVVVALVALTVAEGEASEQLQCERELQERELKACQQVMDQQLRDISPECHPVVVSPVAGQYEQQIVVPPKGGSFYPGETTPPQQLQQRIFWGIPALLKRYYPSVT
CPQQVSYYPGQASPQRPGQGQQGPGQGPGQGQQPGQGQGQQPGQGQPRYYPTSPQQSGQLQPAQGQQPGQGQQPEQGQPRYYPTSPQQSGQLQQPAQGQQPGQGQQPGQGQGQGQGQQPGQGQQPGOQG
QQPGQGQPGYYPTSPQQSGQGQPGYYPTSPQQSGQGQGQQPGYYPTSLQQSGQGQPGYYPTSLQQLGQGQGQQPGYYPTSPQQSGQGQQPGQGQYLTSPQQSGQGQQPGQLQQSAQGQQGQQPGOQG
QQPGQGQQPGQGQQPGQGQQPGOGQQPGQGQOQPGQGQPGYYPTSPQQSGQGQQPGYYPTSPLQPGQQPGQQPGYYPTSPLQPGQQPGOQQPGYYPTSPLQPGQQPGOQQPGQGQQPWYYPTSPQESGQGQPGOQQPGOQQPGYYLTSPLQLGQGOQG
AQGQGQOQPGQGQOQPGQGQOLGQGQGQQPGQGQWQSGQGQHWYYPTSPQLSGQGQRPGQMLQPGQGQGYYPTSPQQPGQQPGQLGQMLQPGQGQGYYPTSLQQTGQGQQSGQGQQGYSSYHVSVEHQAAS
YYPTSLQQPGQGQQPGQGQQPGOGQWQSGQGQHWYYPTSPQLSGQGQRPGQWLQPGQGQGYYPTSPQQPGQQPGQLGQWLQPGQGQGYYPTSLQQTGQGQQSGQGQQGYSSYHVSVEHQAAS
LKVAKAQQLAAQLPAMCRLEGGDALSASQ*   (SEQ ID NO:90)
```

FIG. 11

> Triticum aestivum Glu-1D-1d gene for high molecular weight glutenin subunit 5 translated CDS; GeneBank X12928.5

MAKRLVLFVAVVVALVALTVAEGEASEQLQCE
RELQELQERELKACQQVMDQQLRDISPECHPV
VVSPVAGQYEQQIVPPKGGSFYPGETTPPQQ
LQQRIFWGIPALLKRYPPSVTCPQQVSYYPGQ
ASPQRPGQGQQPGQGQQGYYPTSPQQPGQWQQ
PEQGQPRYYPTSPQQSGLQQPAQGQQPGQGQ
QGQQPGQGQQPGYYPTSSQLPGQLQQPAQGQQ
GQQPGQAQGQQPGQGQQGYYPTSLQQSGQGQPG
GQPGQGQQLGQGQQGYYPTSLQQSGQGQPG
YYPTSLQQLGQGQSGYYPTSPQQPGQGQQPGQ
LQQPAQGQQPGQGQQPGYYPTSSQQP
QPGQGQQPGYYPTSPQQSGQGQQVGQGQQAQPGQGQQPGQ
TQSQQPGQGQGQQPGQGQQPGYYPTSPQQSGQGQ
GQPGYYPTSPQQSGQGQPGYYLTSPQQSGQGQ
QPGQLQQSAQGKGQPGQGQPGQGQQGQGQ
QPGQGQQPGQGQQPGYYPTSPQQSGQGQQPGQ
WQQPGQGQQPGYYPTSPLQPGQGQPGYDPTSPQ
QPGQGQQPGQLQQPAQGQQGQLAQGQQGQQP
AQVQQGQRPAQGQQGQGQPAQGQQGQGQPGQGQQLGQGQQ
GQQPGQGQGQGQQGQQPAQGQQGQGQQGQGQPG
GQGQQPGQGQGQPGYYLTSPLQLGQGQQGYY
PTSLQQPGQGQQPGQWQQSGQGQHWYYPTSPQ
LSGQGQRPGQWLQPGQGQQGYYPTSPQQPGQG
QQLGQWLQPGQGQQGYYPTSLQQTGQGQQSGQ
GQQGYYSSYHVSVEHQAASLKVAKAQQLAAQL
PAMCRLEGGDALSASQ* (SEQ ID NO:90)

Threonine content: 3.0%
Lysine content: 0.8%

> Triticum aestivum Glu-1D-1d gene for high molecular weight glutenin subunit 5 translated CDS; -2 frameshift at the start of the coding sequence MAKRLVLFVAVVVALVALTVAEGEASEQLQCE
RELQELQERELKACQQVMDQQLRDIPRVPPRR
RQPGRGTRAANRGAAQGRIFLPRRDHATAAT
PTTYILGNTCTTKKVLPKCNLSAAGFILSRPS
FSATARTRSAARTRTRVLPNFSATARTMATT
GTRATKVLPNFSAAVRTIATTSTRAATRTRAT
RSAARTRATRVLPNFFAAAARTIATTSTRATR
AATRSATRSTARTRATTRTRTRSTARTRAT
TRTRATRSAARTRTTRVLPNFSATVGTRATRV
ILPNFSAAARTRATRVLPNFSAATRTRAAARTI
ATTSTRAATRTRATRSAARTRATRPAARTRAA
TGTRATRVLPNFSAAVRTRATRVLPNFFAAAN
TIAATRTRATRSAGRTRATRSSAARTRAATGTR
AARTRATISTRAKRTATRTRSTARARATRSAAR
TRATRSATGARAARTLPNFSAAIRTRATARTM
ATTRTRATRILPNFSVAARTRATRVRPNFSAT
ARTRAATRTIATTSTRATRAAATSTRATRAATS
TSATRAAASTRATRSAARTRATRSAARTRATR
SAARTRATRAATSTRATRSAARTRATRSAART
RATRSAARTRAATGTRAAMVLPNFSAGVRTRA
TARTMATTRTRATRVLPNFSVAARTRATRVLP
NFSATTRTRAATRTMATIGTRATLVLPNFSAA
VRTRATRMAATRTRATRVLPNFSATARTRA
TTRTMAATRTRATRVLPNFSATDRTRAAIRTR
ATRLLQLIPC* (SEQ ID NO:91)

Threonine content: 21.4%
Lysine content: 0.9%

> Triticum aestivum Glu-1D-1d gene for high molecular weight glutenin subunit 5 translated CDS; -1 frameshift at the 5' end of the coding sequence MAKRLVLFVAVVVALVALTVAEGEASEQLQCE
RELQELQERELKACQQVMDQQLRDISPECHPV
VVSPVAGQYEQQIVPPKGGSFYPGETTPPQQ
LQQRIFWGIPALLKRYPPSVLVRSRFHTIQAK
LLRNGQDKVSSQDKDNKGTTQLLRNSQDNGNN
RNKGNQGTTQLLRSSQDNCNNQHKGSNQDKGN
KVSSQDKGNQGTTQLLRSCSQDNCNNQHKGNK
GSNQDKRNKVNSQDKGNNQDKDNKVNSQDKGN
NQDKGNKVSSSDKDNKGTTQLLCNSRDKGNQG
TTQLLCSS* (SEQ ID NO:92)

Threonine content: 4.7%
Lysine content: 8.7%

METHODS FOR ALTERING AMINO ACID CONTENT IN PLANTS THROUGH FRAMESHIFT MUTATIONS

CROSS-REFERENCE TO RELATED APPLICATIONS

This application is a U.S. National Stage Application under 35 U.S.C. § 371 and claims benefit of priority from International Patent Application No. PCT/IB2017/057190, filed on Nov. 16, 2017, which claims benefit of priority from U.S. Provisional Application Ser. No. 62/485,001, filed on Apr. 13, 2017, and U.S. Provisional Application Ser. No. 62/422,854, filed on Nov. 16, 2016, the disclosures of which are incorporated herein by reference in their entirety.

TECHNICAL FIELD

This document provides materials and methods for generating plants with altered levels of amino acids.

BACKGROUND

Humans, as well as farm animals, are unable to synthesize several amino acids that are required for survival, including histidine, isoleucine, leucine, methionine, phenylalanine, threonine, tryptophan, valine, and lysine. As a result, the diet of humans and farm animals must contain sufficient levels of these essential amino acids. In developed countries, optimal levels of essential amino acids are generally achieved through diets consisting of meat, eggs, milk, cereals, and legumes. However, in developing countries, diets are frequently restricted to major crop plants, which can result in a deficiency of particular amino acids. Suboptimal levels of essential amino acids can lead to protein-energy malnutrition (PEM), which is characterized by increased susceptibility to disease, decreased levels of blood proteins, and impaired mental and physical development in children. It is estimated by the World Health Organization that 30% of the population in developing countries suffer from PEM (Onis et al., *Bull World Health Organ*, 71: 703-712, 1993).

SUMMARY

This document provides materials and methods for generating plants with altered (e.g., increased) levels of particular amino acids. For example, this document relates to the use of genome engineering tools (e.g., sequence-specific nucleases and donor molecules) to generate controlled frameshift mutations that lead to altered amino acid content in plants that are modified using the tools. The methods described herein can be useful to, for example, fortify major crop plants with increased levels of essential amino acids, thus providing the potential to improve human health. Further, plants containing genome modifications introduced by sequence-specific nucleases are not regulated in certain jurisdictions; therefore, this is considered a non-transgenic approach to improving the amino acid content in crop plants.

This disclosure is based at least in part on the discovery that plants with altered amino acid content can be obtained using sequence-specific nucleases to generate controlled frameshift mutations. Specifically, it has been determined that (i) small deletions or insertions can result in frameshift mutations, (ii) sequence-specific nucleases with or without a donor molecule can generate targeted frameshift mutations, and (iii) codons within alternative reading frames can encode valuable amino acids. In some embodiments, the methods provided herein can involve the design and delivery of sequence-specific nucleases targeting coding sequence within a gene of interest. Erroneous repair of the resulting double-strand break by non-homologous end joining (NHEJ) can result in a frameshift mutation, which can subsequently lead to a premature stop codon and a truncated protein. As described herein, frameshift mutations also can be used to modulate the amino acid composition of proteins, and ultimately, the amino acid content in modified plants. Controlled frameshift mutations within genes that are highly expressed (e.g., seed storage protein genes, including gliadin, hordein, secalin, zein, kafirin, avenin, glycinin, and conglycinin), can result in the production of proteins with significantly higher levels of one or more amino acids of interest.

In addition, this document is based at least in part on the development of crop varieties with mutations in seed storage proteins, or other highly expressed genes, where the mutations are created using sequence-specific nucleases. The methods provided herein for modulating amino acid content can be achieved without insertion of a transgene. In addition, the materials and methods provided herein can address challenges associated with commercializing transgenic plants, including strict regulation in certain jurisdictions, and high costs to obtain regulatory approval. The methods described herein can accelerate the production of new crop varieties with modified levels of amino acids, and can be more cost effective than transgenic or traditional breeding approaches.

In one aspect, this document features a method for altering the amino acid content of a polypeptide. The method can include evaluating two or more reading frames within a nucleic acid encoding the polypeptide, identifying a reading frame that encodes an amino acid sequence having a desired amino acid content, and introducing a frameshift mutation into the nucleic acid such that when the nucleic acid sequence is expressed in a cell, the polypeptide having the desired amino acid content is expressed. The frameshift mutation can be of the size $-3(N)-2$, or the size $+3(N)+1$. The method can include contacting the nucleic acid with a rare-cutting endonuclease to introduce the frameshift mutation. The rare-cutting endonuclease can be a transcription activator-like effector endonuclease (TALE nuclease), a meganuclease, a zinc finger nuclease (ZFN), or a clustered regularly interspaced short palindromic repeats (CRISPR)/CRISPR-associated (Cas) nuclease reagent. The polypeptide encoded by the nucleic acid containing the frameshift mutation can have increased sulfur-containing amino acid content as compared to a corresponding wild type polypeptide. The nucleic acid can encode a soybean globulin polypeptide, where the frameshift mutation is within the sequence set forth in SEQ ID NO:94, or a sequence having at least 90% identity to SEQ ID NO:94. The polypeptide encoded by the nucleic acid containing the frameshift mutation can be a soybean globulin polypeptide that contains the amino acid sequence set forth in SEQ ID NO:95. The polypeptide encoded by the nucleic acid containing the frameshift mutation can have increased threonine content as compared to a corresponding wild type polypeptide. The nucleic acid can encode a wheat alpha gliadin polypeptide, where the frameshift mutation is within the sequence set forth in SEQ ID NO:96, or a sequence having at least 90% identity to SEQ ID NO:96. The polypeptide encoded by the nucleic acid containing the frameshift mutation can be a wheat alpha gliadin polypeptide that contains the amino acid sequence set forth in SEQ ID NO:97, or an amino acid sequence having at least 90% sequence identity to SEQ ID NO:97.

The nucleic acid can encode a wheat high molecular weight glutenin polypeptide, where the frameshift mutation is within the sequence set forth in SEQ ID NO:70, or a sequence having at least 90% identity to SEQ ID NO:70. The frameshift mutation can encompass or be 3' to the nucleotide at position 171 of SEQ ID NO:70. The polypeptide encoded by the nucleic acid containing the frameshift mutation can be a wheat high molecular weight glutenin polypeptide that contains the amino acid sequence set forth in SEQ ID NO:98, or an amino acid sequence having at least 90% identity to SEQ ID NO:98. The polypeptide encoded by the nucleic acid containing the frameshift mutation can have increased lysine content as compared to a corresponding wild type polypeptide. The nucleic acid can encode a wheat high molecular weight glutenin polypeptide, where the frameshift mutation is within the sequence set forth in SEQ ID NO:70, or a sequence having at least 90% identity to SEQ ID NO:70. The frameshift mutation can encompass or be 3' to the nucleotide at position 348 of SEQ ID NO:70. The polypeptide encoded by the nucleic acid containing the frameshift mutation can be a wheat high molecular weight glutenin polypeptide that contains the amino acid sequence set forth in SEQ ID NO:99, or an amino acid sequence having at least 90% identity to SEQ ID NO:99. The method can further include introducing a second frameshift mutation into the nucleic acid encoding the polypeptide, where the frameshift mutations in combination result in a deletion or insertion of nucleotides, and where the size of the deletion or insertion is a multiple of 3.

In another aspect, this document features a method for generating a plant, plant part, or plant cell with altered levels of amino acids, where the method includes (a) contacting a plant, plant part, or plant cell with a rare-cutting endonuclease targeted to a sequence within an exon of a gene endogenous to the plant, plant part, or plant cell, such that the rare-cutting endonuclease generates a double strand break at or near the sequence to which it is targeted, and (b) selecting a plant, plant part, or plant cell that contains a frameshift mutation within the exon, wherein the plant, plant part, or plant cell has altered amino acid levels as compared to a control plant, plant part, or plant cell in which the frameshift mutation was not introduced. The method can further include growing a plant part or plant cell selected in step (b) into a plant. In some embodiments, the plant cell that is contacted in step (a) can be a protoplast. The method can include transforming the protoplast with a nucleic acid (e.g., an RNA, or a nucleic acid contained within a vector) encoding the rare-cutting endonuclease. In some embodiments, the plant part that is contacted in step (a) can be an immature embryo or embryogenic callus. The method can include transforming the embryo or embryogenic callus with a nucleic acid encoding the rare-cutting endonuclease. The transforming can include *Agrobacterium*-mediated transformation or biolistics. The rare-cutting endonuclease can be a transcription activator-like effector endonuclease (TALE nuclease), meganuclease, zinc finger nuclease (ZFN), or clustered regularly interspaced short palindromic repeats (CRISPR)/CRISPR-associated (Cas) nuclease reagent. In some embodiments, the method can further include culturing the protoplasts, immature embryos, or embryogenic calli to generate plant lines. The frameshift mutation can be in the coding sequence of the gene, or within the last exon of the gene. The frameshift can be introduced by homologous recombination with a user-supplied donor molecule. The frameshift mutation can be within a gene that encodes a seed storage protein (e.g., gliadin, hordein, secalin, zein, kafirin, avenin, glycinin, or conglycinin). In some cases, the seed storage protein encoded by the gene containing the frameshift mutation can contain the amino acid sequence set forth in SEQ ID NO:95, SEQ ID NO:98, or SEQ ID NO:99, or an amino acid sequence having at least 90% identity to SEQ ID NO:95, SEQ ID NO:98, or SEQ ID NO:99. The frameshift mutation can be within a gene that encodes a protein expressed in leaf tissue (e.g., ribulose-1,5-bisphosphate (RuBP) carboxylase/oxygenase (rubisco), translational elongation factor EF-1 alpha (EF1a), or ubiquitin).

In another aspect, this document features a method for generating a plant, plant part, or plant cell with altered levels of amino acids, where the method includes (a) contacting a plant, plant part, or plant cell with a first rare-cutting endonuclease targeted to a sequence within a gene endogenous to the plant, plant part, or plant cell, such that the first rare-cutting endonuclease generates a double strand break at or near the sequence to which it is targeted, (b) selecting a plant, plant part, or plant cell that contains a first frameshift mutation within the gene, (c) contacting a plant, plant part or plant cell with a second rare-cutting endonuclease targeted to a sequence within the same gene as that to which the first rare-cutting endonuclease was targeted, such that the second rare-cutting endonuclease generates a double strand break at or near the sequence to which it is targeted, and (d) selecting a plant, plant part, or plant cell that contains a second mutation within the endogenous gene. In some embodiments, the plant cell that is contacted in step (a) or step (c) can be a protoplast. The method can include transforming the protoplast with a nucleic acid (e.g., an mRNA or a nucleic acid contained within a vector) encoding the first or second rare-cutting endonuclease. In some embodiments, the plant part that is contacted in step (a) or step (c) can be an immature embryo or embryogenic callus. The method can include transforming the embryo or embryogenic callus with a nucleic acid encoding the first or second rare-cutting endonuclease. The transforming can include *Agrobacterium*-mediated transformation or transformation by biolistics. The first or second rare-cutting endonuclease can be a TALE nuclease, meganuclease, ZFN, or CRISPR/Cas reagent. The method can further include culturing the protoplast, immature embryo, or embryogenic callus to generate a plant line. The first frameshift mutation can be introduced chronologically before the second mutation, and the second mutation can be introduced into a plant, plant part, or plant cell selected in step (b). Alternatively, the second mutation can be introduced chronologically before the first frameshift mutation, and the first frameshift mutation can be introduced into a plant, plant part, or plant cell selected in step (d). The method of claim 17, wherein the first frameshift mutation is within an exon of the gene. The second mutation can be is downstream of the first frameshift mutation. The second mutation can be a frameshift mutation that re-introduces the normal reading frame found in the wild type gene. The second mutation can inactivate splicing of introns downstream from the first frameshift mutation. The first frameshift mutation or the second mutation can be introduced by homologous recombination using a user-generated donor molecule. The first frameshift mutation and the second mutation can be introduced simultaneously by homologous recombination using a user-generated donor molecule, or by simultaneously delivering two or more rare-cutting endonucleases. The frameshift mutation can be within a gene that encodes a seed storage protein (e.g., gliadin, hordein, secalin, zein, kafirin, avenin, glycinin, or conglycinin). In some cases, the seed storage protein encoded by the gene containing the frameshift mutation can contain the amino acid sequence set forth in SEQ ID NO:95, SEQ ID NO:98, or SEQ ID NO:99, or an amino acid sequence having at least 90% identity to SEQ ID NO:95, SEQ ID NO:98, or SEQ ID NO:99. The frameshift mutation can be within a gene that encodes a protein expressed in leaf tissue (e.g., rubisco, EF1a, or ubiquitin).

In another aspect, this document features a plant, plant part, or plant cell with altered levels of amino acids, wherein the plant contains a frameshift mutation in an exon of a selected gene. The altered levels of amino acids can have at least a 0.1% increase or decrease in the content of one or more amino acids. The plant, plant part, or plant cell can contain a second frameshift mutation within the selected gene. The plant, plant part, or plant cell can contain a second mutation within an exon or intron of the selected gene. The second mutation can be a deletion, insertion, substitution, or inversion of nucleotides that are required for intron splicing. The plant, plant part, or plant cell can be a wheat, cassava, alfalfa, oat, corn, rice, sorghum, potato, tomato, soybean, or canola plant, plant part, or plant cell.

In addition, this document features a method for generating plant, plant cell, or plant part having a frameshift mutation in at least one protein-coding sequence that is endogenous to the plant, plant cell, or plant part such that the plant, plant cell, or plant part has increased or decreased levels of one or more amino acids of interest as compared to a control plant, plant cell, or plant part that lacks the frameshift mutation. The frameshift can be introduced by a deletion of nucleotides, or an insertion of nucleotides. The deletion of nucleotides can be a length of $-3(N)-1$, where N is any whole number, including zero. Furthermore, the deletion of nucleotides can be a length of $-3(N)-2$, where N is any whole number, including zero. The insertion of nucleotides can be a length of $+3(N)+1$, where N is any whole number, including 0. Furthermore, the insertion of nucleotides can be a length of $+3(N)+2$, where N is any whole number, including 0. In some embodiments, the mutation can include a combination of an insertion and deletion which results in a final increase in the length of nucleotides with the cumulative length of $+3(N)+1$ or $+3(N)+2$ nucleotides, where N is any whole number, including 0. In some embodiments, the mutation can include a combination of an insertion and deletion which results in a final decrease in the length of nucleotides with the cumulative length of $-3(N)-1$ or $-3(N)-2$ nucleotides, where N is any whole number including 0. The frameshift mutation can occur at a target sequence anywhere between the start codon and stop codon of a protein-coding gene that does not contain introns. The frameshift mutation can be at a target sequence within the last exon of a protein-coding gene. The mutation can be at a target sequence within the second to last exon of a protein-coding gene. The mutation can be at a target sequence within any exon of a protein-coding gene.

In another aspect, this document features a method for generating a plant, plant cell, or plant part having an additional mutation downstream of a frameshift mutation, such that the a plant, plant cell, or plant part has increased expression of the protein-coding sequence containing the frameshift as compared to a control plant, plant cell, or plant part that does not contain the additional mutation, but contains the upstream frameshift mutation. The mutation can include a deletion of one or more nucleotides, an insertion of one or more nucleotides, a substitution of one or more nucleotides, or an inversion of sequence. In some embodiments, the mutation can include a combination of two or more of: deletion of one or more nucleotides, inversion of one or more nucleotides, insertion of one or more nucleotides, and substitution of one or more nucleotides within an allele. The mutation can result in the inactivation of intron splicing of one or more introns downstream of the stop codon introduced by the frameshift. The plant, plant cell, or plant part can have increased levels of gene expression of the protein-coding sequence containing the frameshift mutation, as compared to a plant, plant cell, plant part that does not contain the mutation, but contains the frameshift mutation.

In still another aspect, this document features a plant, plant cell, or plant part having two frameshift mutations such that the plant, plant cell, or plant part has increased levels of the modified protein as compared to a control plant, plant cell, or plant part that does not contain the two frameshift mutations. In another aspect, this document features a plant, plant cell, or plant part having an additional mutation downstream of a frameshift mutation, such that the a plant, plant cell, or plant part has increased expression of the protein-coding sequence containing the frameshift as compared to a control plant, plant cell, or plant part that does not contain the additional mutation, but contains the upstream frameshift mutation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 the genomic sequence encoding the soybean seed storage protein, Gy4 (Glyma10g04280; SEQ ID NO:1). Upper case letters indicate exon sequences, and lower case letters indicate intron sequences. There are four exons and three introns within the Gy4 gene.

FIGS. 3A and 3B illustrate a process for finding an alternative reading frame with high methionine and lysine codons. The figures show the *Glycine max* Gy4 exon 1 (SEQ ID NO:2; FIG. 3A), exon 2 (SEQ ID NO:12; FIG. 3A), exon 3 (SEQ ID NO:20; FIG. 3B), and exon 4 (SEQ ID NO:40; FIG. 3B) sequences, followed by the three translated frames for each exon. Underlined letters within the −1 frame of exon 3 indicate the region with the highest level of methionine and lysine. Underlined letters within the exon 3 sequence (SEQ ID NO:20) indicate the binding site of a TALE nuclease designed to introduce the desired −3(N)−1 or +3(N)+2 frameshift mutation.

FIG. 4 is an example of the amino acid sequence of Gy4 before a frameshift mutation (>Gy4 wild type; left panel; SEQ ID NO:55) and after a frameshift mutation (>Gy4; right panel; −1 frameshift within exon 3; early stop codon at the end of exon 3; SEQ ID NO:56). The methionine and cysteine content increases from 1.5% to 4.1%, and the lysine content increases from 5% to 9.1%. Alternating normal font and italics indicate the different exons that encode the amino acids. The first 23 letters (bold) indicate the signal sequence. Methionine and cysteine amino acids are bold and underlined.

FIG. 6 shows the amino acid sequence of Gy4 (>Gy4 wild type; left panel; SEQ ID NO:55) and the sequence of Gy4 after the introduction of two frameshift mutations as illustrated in FIG. 5 (>Gy4; right panel; −1 frameshift within exon 3; frameshift at the end of exon 3 to restore original frame; SEQ ID NO:57). The methionine and cysteine content increases from 1.5% to 3.3%, and the lysine content increases from 5% to 7.2%.

FIG. 8 illustrates a process for finding an alternative reading frame with high threonine codons. A representative *Triticum aestivum* alpha gliadin coding sequence (GENBANK® JN831386.1; SEQ ID NO:58) is followed by the three translated reading frames. Underlined letters within the −2 frame indicate the region with the highest level of threonine amino acids. Underlined letters in the alpha gliadin coding sequence indicate the binding site of a TALE nuclease designed to introduce the desired −3(N)−2 or +3(N)+1 frameshift mutation.

FIG. 9 is an example of the amino acid sequence of a WT alpha gliadin protein (>*Triticum aestivum* clone 1-8 alpha gliadin (gli-2) gene, translated cds; left panel; GENBANK® JN831386.1; SEQ ID NO:68) and an alpha gliadin protein where a −2 frameshift occurs in the coding sequence near the start codon (>*Triticum aestivum* clone 1-8 alpha gliadin (gli-2) gene, translated cds; right panel; −2 frameshift mutation at the beginning of the coding sequence; SEQ ID NO:69). The resulting protein has increased threonine and lysine content.

FIGS. 10A and 10B illustrate a process for finding an alternative reading frame with high threonine and lysine codons. A representative *Triticum aestivum* glutenin coding sequence (FIG. 10A, *Triticum aestivum* Glu-1D-1d gene for high molecular weight glutenin subunit 5; GENBANK® X12928.5; SEQ ID NO:70), followed by the three translated reading frames (FIG. 10B). Underlined letters within the −1 and −2 frames indicate the regions with the highest level of lysine and threonine amino acids, respectively.

FIG. 11 is an example of the amino acid sequence of a WT glutenin protein (>*Triticum aestivum* Glu-1D-1d gene for high molecular weight glutenin subunit 5 translated CDS; GENBANK® X12928.5; SEQ ID NO:90) and a glutenin protein with a −2 frameshift in the coding sequence near the start codon (>*Triticum aestivum* Glu-1D-1d gene for high molecular weight glutenin subunit 5 translated CDS; −2 frameshift at the start of the coding sequence; SEQ ID ON:91). The resulting protein has increased threonine lysine content, relative to the wild type protein. Also shown is the amino acid sequence of a glutenin protein with a −1 frameshift (>*Triticum aestivum* Glu-1D-1d gene for high molecular weight glutenin subunit 5 translated CDS; −1 frameshift at the 5' end of the coding sequence; SEQ ID NO:92). The resulting protein has increased levels of threonine and lysine compared to the wild type protein.

DETAILED DESCRIPTION

Figure 1:
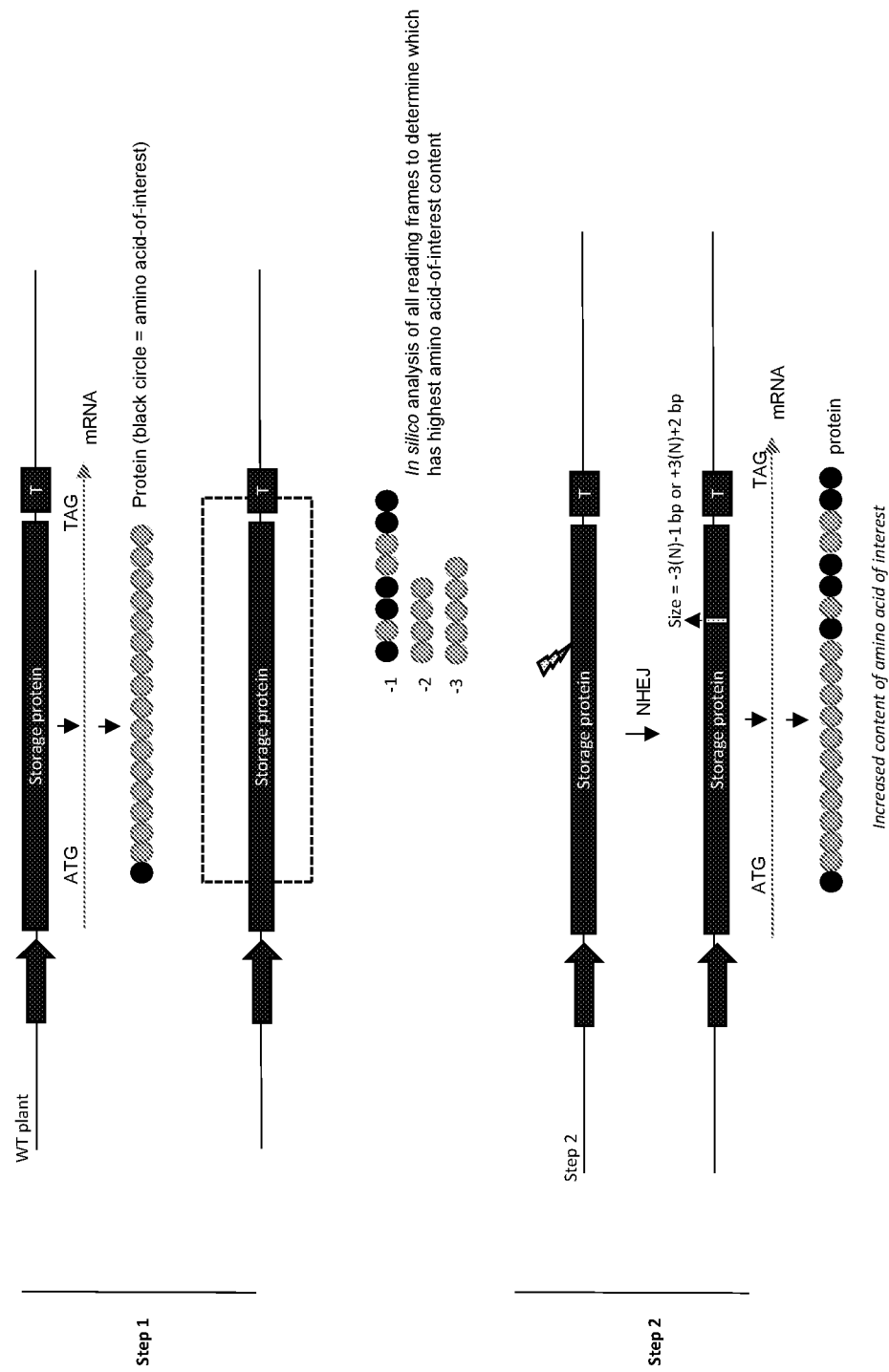
FIG. 1 is a diagram illustrating an approach for altering the amino acid content of a protein of interest. Step 1 involves the in silico analysis of all reading frames of a gene of interest to determine which reading frame has the highest level of the desired amino acid of interest. After finding the location of a desired reading frame, Step 2 involves the design and delivery of a sequence-specific nuclease for creating a controlled frameshift mutation. In the example shown in Step 1, the reading frame with the highest level of the amino acid of interest is −1. Therefore, the size of nuclease-mediated deletion can be −3(N)−1, where N is any whole number, including 0 Notably, the mutation can also be an insertion with the size of +3(N)+2, where N is any whole number including 0.

Cereal and legume crops have limited levels of essential amino acids. For example, legumes, including soybean, have limited levels of methionine (Met), while cereal crops, including barley, corn, sorghum, and wheat, have limited levels of lysine (Lys) and threonine (Thr) (see, e.g., Galili et al., *Biol Chem*, 386: 817-831, 2005; *Swine Nutrition* (Lewis and Southern, Eds.), pp. 131-150, CRC Press, Boca Raton, Fla., 2014). Efforts to improve the Lys and/or Met amino acid content in cereal and legume crops typically have utilized one of two approaches—classical breeding and genetic engineering, both of which have met with limited success. Challenges of classical breeding include (1) the need to specifically increase Lys and/or Met content in seeds but not vegetative tissues, due to deleterious effects on plant growth (Bright et al., *Biochem Genet*, 20: 229-243, 1982; Ghislain et al., *Plant J*, 8:733-743, 1995), and (2) the need to incorporate Lys and/or Met within the major seed storage proteins (Ufaz and Galili, *Plant Physiol*, 100: 1157-1163, 2008). Genetic engineering can alleviate such challenges. For example, genetic engineering can use seed-specific promotors to express genes with high levels of Lys or Met, or to express RNA or protein that leads to increased levels of Lys or Met. A strong understanding of amino acid metabolic pathways is required for such genetic engineering, however. Further, whereas many genetic engineering approaches have resulted in increased levels of Met or Lys, they also have been associated with abnormal and undesired plant phenotypes (Zeh et al., *Plant Physiol*, 127: 792-802, 2001). Examples of genetic engineering approaches to improve Lys or Met content have included seed-specific expression of a feedback-insensitive dihydropicolinate synthase enzyme of Lys synthesis (Zhu et al., *Plant Cell*, 15: 845-853, 2003), suppression of the Lys catabolism genes lysine ketoglutarate reductase/saccharopine dehydrogenase (Reyes et al., *Plant Mol Biol*, 69: 81-89, 2009), RNAi-mediated knockdown of low Lys containing zein genes (Huang et al., *J Agric Food Chem*, 52: 1958-1964, 2004), overexpression of the Met biosynthesis pathway gene cystathionine gamma-synthase (Kim et al., *Plant Physiol*, 128: 95-107, 2002), RNAi-mediated knockdown of threonine synthase (Zeh et al., *Plant Physiol*, 127: 792-802, 2001), and knockdown of the Met catabolic enzyme SAM synthase (Goto et al., *Genes Genet Syst*, 77: 89-95, 2002).

The methods provided herein include the use of tools for precise genome engineering (e.g., sequence-specific nucleases and donor molecules), and provide a novel approach for modulating amino acid content in crop plants and proteins. As used herein, the terms "amino acid levels" and "amino acid content" refer to the percentage of a specific amino acid among total amino acids. When referring to a plant, plant part, or plant cell, "content" or "level" refers to the number of specific amino acids divided by the total number of amino acids within the plant, plant part, or plant cell. For example, a soybean seed with 1% methionine refers to a seed that contains 1 methionine for every 99 non-methionine amino acids, over the total population of amino acids. "Content" or "level" also can refer to the percentage of a specific amino acid within a protein. For example, a protein with 1% methionine refers to a protein that contains 1 methionine for every 99 non-methionine amino acids, over the total number of amino acids of the protein.

The terms "altered" and "modulated," as used herein with regard to amino acid levels or amino acid content, refer to a change in the relative amount of one or more particular amino acids within a protein, plant, plant part, or plant cell, where the change is an increase or decrease of at least 0.1% (e.g., at least 0.25%, 0.5%, 1%, 5%, 10%, 0.1 to 0.5%, 0.5 to 1%, 1 to 3%, 3 to 5%, 5 to 10%, or more than 10%), relative to the level or content of the particular amino acid(s) in a corresponding protein, plant, plant part, or plant cell that has not been modified according to the methods described herein. For example, a modified soybean seed with 2% methionine levels has an altered level of amino acids compared to an unmodified soybean seed containing 1% methionine. The modified soybean seed has an increased methionine content of 1% compared to an unmodified soybean seed.

The methods provided herein can include, for example, contacting a plant, plant part, or plant cell with a rare-cutting endonuclease targeted to a sequence within an exon of a gene endogenous to the plant, plant part, or plant cell (e.g., a gene encoding a seed storage protein, or a protein expressed in a particular tissue, such as leaves), such that the rare-cutting endonuclease generates a double strand break at or near the sequence to which it is targeted, and then selecting a plant, plant part, or plant cell that contains a frameshift mutation within the exon. The frameshift of interest can be predetermined according to the methods described herein, which can include, for example, determining which reading frame of the exon contains the desired (e.g., greatest) level of one or more particular amino acids (e.g., essential amino acids, including histidine, isoleucine, leucine, lysine, methionine, phenylalanine, threonine, tryptophan, and valine). Methods for determining whether a plant, plant part, or plant cell contains a frameshift mutation in a particular gene include those well known in the art.

In some embodiments, the methods provided herein further can include contacting a plant, plant part or plant cell with a second rare-cutting endonuclease targeted to a sequence within the same gene as that to which the first rare-cutting endonuclease was targeted, such that the second rare-cutting endonuclease generates a double strand break at or near the sequence to which it is targeted, and then selecting a plant, plant part, or plant cell that contains a second mutation within the endogenous gene. The first and second mutations can be generated in either order, such that a plant, plant part, or plant identified as having the first frameshift mutation can be subsequently be contacted with the second rare-cutting endonuclease, or a plant, plant part, or plant cell identified as containing the second mutation can subsequently be contacted with the first rare-cutting endonuclease. In some cases, the methods provided herein can include simultaneously delivering two or more rare-cutting endonucleases, such that the first and second mutations are generated at essentially the same time. The second mutation can be upstream or downstream from the first frameshift mutation. In some cases, the second mutation can be a frameshift that re-introduces the normal reading frame that is found in the wild type gene, or the second mutation can inactivate splicing of introns downstream from the first frameshift mutation.

The plant cells that are contacted with a rare-cutting endonuclease can be, for example, protoplasts. Plant parts that can be contacted with a rare-cutting endonuclease include, without limitation, immature embryos, cotyledons, leaves, floral organs, roots, stems, or embryonic calli. The contacting can include, for example, transformation with a nucleic acid (e.g., a DNA or RNA, including DNA or RNA within a vector) encoding the rare-cutting endonuclease. In some embodiments, for example, a plant, plant part, or plant cell can be transformed with an mRNA encoding the rare-cutting endonuclease. Any suitable method of transformation can be used, including, without limitation, *Agrobacterium*-mediated transformation, polyethylene glycol (PEG) mediated transformation, electroporation, calcium phosphate mediated transformation, virus-mediated transformation, microinjection, laser mediated transformation, liposome mediated transformation, or techniques utilizing cell-penetrating peptides, silicon carbide fibers, or biolistics. The methods provided herein also may include culturing transformed protoplasts, immature embryos, or embryogenic calli to generate plant lines.

In some cases, a frameshift mutation and/or a second mutation can be introduced by homologous recombination with an exogenous donor molecule (e.g., a donor molecule provided by the entity carrying out the method). Further, the first frameshift mutation and the second mutation can be introduced simultaneously by homologous recombination using a single donor molecule that includes both mutations.

In some embodiments, when a plant part or plant cell has been identified as containing a desired frameshift mutation and/or a desired second mutation, the methods provided herein can further include growing the plant part or plant cell into a plant.

It is to be noted that while the examples described herein focus on increasing Lys and/or Met levels in soybean or Lys and/or Thr levels in wheat, it is to be noted that this approach can be extended to modulating the content of other amino acids in additional crop species. For example, the methods provided herein can be used to modulate the levels of one or more essential amino acids (e.g., histidine, isoleucine, leucine, lysine, methionine, phenylalanine, threonine, tryptophan, and valine) in a crop species such as, without limitation, cassava, alfalfa, oat, corn, rice, sorghum, potato, tomato, or canola, as well as soybean or wheat.

Soybean (*Glycine max* L. Merr.) is an important source of protein for livestock production and is of growing importance as a protein source for human consumption. Although soybean has the highest protein content among seed crops, the protein quality is poor due to deficiencies in the content of the sulfur-containing amino acids, methionine and cysteine. Increasing the amount of methionine and cysteine in the amino acid profile of soybean meal would enhance its value for producers and consumers.

Soybean 7S globulin (β-conglycinin) and 11S globulin (glycinin) are the two major protein components of the seed. These two major storage proteins in soybean seeds usually are identified by their sedimentation rates in sucrose gradients (Hill and Breidenbach, *Plant Physiol,* 53:747-751, 1974). The 11S protein (glycinin, legumin) consists of at least four acidic subunits and four basic subunits (Staswick et al. *J Biol Chem,* 256:8752-8755, 1981). These subunits are produced by the cleavage of precursor polypeptides that have been identified through in vitro translation and pulse-labeling experiments (Barton et al. *J Biol Chem,* 257:6089-6095, 1982). The 7S storage protein (conglycinin, vicilin) is a glycoprotein composed of α, α', and (β-subunits (Beachy et al, *J Mol Appl Genet,* 1:19-27, 1981). Together, the 7S and 11S storage proteins constitute about 70% of the total seed protein at maturity, and 30% to 40% of the mature seed weight. Other major proteins in soybean seeds include urease, lectin, and trypsin inhibitors.

Wheat (*Triticum aestivum*) is one of the most-produced cereals worldwide, with an estimated annual production of 713 million tons (Food and Agricultural Organization of the United Nations (FAOSTAT), 2010 Crop Production Data, online at faostat.fao.org/site/567/DesktopDefault.aspx?PageID=567#ancor). Wheat grain is used to make flour for breads, cakes, pastas and biscuits, and to make beer and biofuels. Gluten, the major protein component in wheat grains, is primarily composed of gliadins (alcohol-water soluble) and glutenins (insoluble). The gliadins can be divided into three subclasses of proteins: α-, γ-, and ω-gliadins. The genes encoding gliadin proteins are present in tightly-linked clusters within the Gli-1 loci (γ- and ω-gliadins), Gli-2 loci (α-gliadins), and Gli-3 loci (ω-gliadins). The Gli-1 loci are present on the short arm of the homologous group 1 chromosomes (Gli-A1, Gli-B1, and Gli-D1), whereas the Gli-2 loci are found on the short arm of chromosome 6 (Gli-A2, Gli-B2, and Gli-D2). The copy number of gliadin genes within hexaploid wheat genomes is estimated to be 25 to 150 copies for α-gliadins, 15 to 18 copies for ω-gliadins, and 17 to 39 copies for γ-gliadins (Gil-Humanes et al., *Proc Natl Acad Sci USA,* 107:17023-17028, 2012).

As used herein, the terms "plant" and "plant part" refer to cells, tissues, organs, grains, and severed parts (e.g., roots, leaves, and flowers) that retain the distinguishing characteristics of the parent plant. "Seed" refers to any plant structure that is formed by continued differentiation of the ovule of the plant, following its normal maturation point, irrespective of whether it is formed in the presence or absence of fertilization and irrespective of whether or not the grain structure is fertile or infertile.

In addition to soybean and wheat, crop plants that can be modified according to the methods provided herein include, without limitation, The term "gene" as used herein refers to a sequence of DNA that encodes a protein. A "gene" also refers to alleles of genes that are present at the same chromosomal position on the homologous chromosome. The term "genes" refers to more than one gene present within the same genome. A "wild type gene" is a naturally occurring gene (e.g., as found within naturally occurring plants) that encodes a protein, while a "mutant gene" or "modified gene" is a gene that has incurred one or more sequence changes, where the sequence changes result in the loss or modification of amino acids within the translated protein, as compared to the wild type gene. Such a "mutant gene" or "modified gene" can include one or more mutations in a gene's nucleic acid sequence.

A representative example of a naturally occurring soybean globulin nucleotide sequence is shown in FIG. 2 herein (from the glycinin Gy4 gene; SEQ ID NO:1), and a representative example of a naturally occurring soybean globulin amino acid sequence is shown in FIG. 4 herein (encoded by Gy4; SEQ ID NO:55). The soybean plants, cells, plant parts, seeds, and progeny thereof that are provided herein can have one or more mutations in one or more endogenous globulin gene(s) (e.g., the Gy4 gene), such that amino acid content of the globulin protein is altered compared to a WT globulin protein. Thus, in some cases, the soybean plants, plant parts, plant cells, seeds, and progeny can exhibit altered overall levels of amino acids.

A representative example of a naturally occurring wheat alpha gliadin nucleotide sequence is shown in FIG. 8 herein (SEQ ID NO:58), and a representative example of a naturally occurring wheat alpha gliadin amino acid sequence is shown in FIG. 9 herein (SEQ ID NO:68). The wheat plants, cells, plant parts, seeds, and progeny thereof that are provided herein can have one or more mutations in one or more endogenous alpha gliadin gene(s), such that the amino acid content of the alpha gliadin protein is altered compared to a WT alpha gliadin protein. Thus, in some cases, the wheat plants, plant parts, plant cells, seeds, and progeny can exhibit altered overall levels of amino acids.

A representative example of a naturally occurring wheat glutenin nucleotide sequence is shown in FIG. 10A herein (SEQ ID NO:70), and a representative example of a naturally occurring wheat glutenin amino acid sequence is shown in FIG. 11 herein (SEQ ID NO:90). The wheat plants, cells, plant parts, seeds, and progeny thereof that are provided herein can have one or more mutations in one or more endogenous glutenin gene(s), such that amino acid content of the glutenin protein is altered compared to a WT alpha gliadin protein. Further, in some cases, the wheat plants, plant parts, plant cells, seeds, and progeny can exhibit altered overall levels of amino acids.

The term "rare-cutting endonuclease" as used herein refers to a natural or engineered protein having endonuclease activity directed to a nucleic acid sequence with a recognition sequence (target sequence) that typically is about 12 to 40 bp in length (e.g., 14-40, 15-36, or 16-32 bp in length). Several rare-cutting endonucleases cause cleavage inside their recognition site, leaving 4 nt staggered cuts with 3'OH or 5'OH overhangs. These rare-cutting endonucleases may be meganucleases, such as wild type or variant proteins of homing endonucleases, more particularly those belonging to the dodecapeptide family (LAGLIDADG (SEQ ID NO:93); see, WO 2004/067736). In some embodiments, a rare-cutting endonuclease can be a fusion protein containing a DNA binding domain and a catalytic domain with cleavage activity. TALE nucleases and zinc-finger-nucleases (ZFNs) are examples of fusions of DNA binding domains with the catalytic domain of the endonuclease FokI. For a review of rare-cutting endonucleases, see Baker, *Nature Methods* 9:23-26, 2012.

Transcription activator-like (TAL) effectors are found in plant pathogenic bacteria in the genus *Xanthomonas*. These proteins play important roles in disease, or trigger defense, by binding host DNA and activating effector-specific host genes (see, e.g., Gu et al., *Nature,* 435:1122-1125, 2005; Yang et al., *Proc Natl Acad Sci USA,* 103:10503-10508, 2006; Kay et al. *Science,* 318:648-651, 2007; Sugio et al., *Proc Natl Acad Sci USA,* 104:10720-10725, 2007; and Römer et al. *Science,* 318:645-648, 2007). Specificity depends on an effector-variable number of imperfect, typically 34 amino acid repeats (Schornack et al., *J Plant Physiol,* 163:256-272, 2006; and WO 2011/072246). Polymorphisms are present primarily at repeat positions 12 and 13, which are referred to herein as the repeat variable-diresidue (RVD).

Another genome engineering tool uses RNA to direct DNA cleavage—the clustered regularly interspaced short palindromic repeats (CRISPR)/CRISPR-associated (Cas) system (see, e.g., Belahj et al., *Plant Methods,* 9:39, 2013). This system consist of a Cas9 endonuclease and a guide RNA (either a complex between a CRISPR RNA [crRNA] and trans-activating crRNA [tracrRNA], or a synthetic fusion between the 3' end of the crRNA and 5'end of the tracrRNA [sgRNA]). The guide RNA directs Cas9 binding and DNA cleavage to homologous sequences that are adjacent to a proto-spacer adjacent motif (PAM; e.g., NGG for Cas9 from *Streptococcus pyogenes*). Once at the target DNA sequence, Cas9 generates a DNA double-strand break at a position three nucleotides from the 3' end of the crRNA targeting sequence. As there are several PAM motifs present in the nucleotide sequence of the globulin genes, the CRISPR/Cas system may be employed to introduce mutations within the globulin alleles within soybean plant cells in which the Cas9 endonuclease and the guide RNA are transfected and expressed. This approach can be used as an alternative to TALE nucleases in some instances, to obtain plants as described herein.

"Mutagenesis" as used herein refers to processes in which mutations are introduced into a selected DNA sequence. Mutations induced by endonucleases generally are obtained by a double strand break, which results in insertion/deletion mutations ("indels") that can be detected by deep-sequencing analysis. Such mutations typically are deletions of several base pairs, and have the effect of introducing frameshift mutations. In the methods described herein, for example, mutagenesis occurs via double stranded DNA breaks made by TALE nucleases targeted to selected DNA sequences in a plant cell. Such mutagenesis results in "TALE nuclease-induced mutations" (e.g., TALE nuclease-induced knockouts). Following mutagenesis, plants can be regenerated from the treated cells using known techniques (e.g., planting seeds in accordance with conventional growing procedures, followed by self-pollination).

In some embodiments, the proteins, plants, plant cells, plant parts, seeds, and progeny provided herein can be generated using a TALE nuclease system to make targeted mutations in one or more selected genes [e.g., one or more genes encoding seed storage proteins such as globulins, glycinin, or gliadin, or one or more genes expressed in leaf tissue, such as ribulose-1,5-bisphosphate carboxylase/oxygenase (rubisco), translational elongation factor EF-1 alpha (EF1a), or ubiquitin]. Thus, this document provides materials and methods for using rare-cutting endonucleases (e.g., TALE nucleases) to generate proteins, plants, and related products (e.g., seeds and plant parts) that can be used as protein sources with reduced levels of low sulfur-containing globulin proteins, due to mutations in globulin genes. Other sequence-specific nucleases also may be used to generate the desired plant material, including engineered homing endonucleases, ZFNs and RNA-guided endonucleases.

In some cases, a mutation can be at a target sequence as set forth in a globulin coding sequence as set forth herein (e.g., a glycinin sequence as set forth SEQ ID NO:1, a gliadin sequence as set forth in SEQ ID NO:58, or a glutenin sequence as set forth in SEQ ID NO:70), or at a target sequence that is at least 90 percent (e.g., at least 90 percent, at least 91 percent, at least 92 percent, at least 93 percent, at least 94 percent, at least 95 percent, at least 96 percent, at least 97 percent, at least 98 percent, at least 99 percent, 90 to 95 percent, 95 to 98 percent, or 98 to 99 percent) identical to the sequence set forth in a sequence as set forth herein (e.g., SEQ ID NO:1, SEQ ID NO:58, or SEQ ID NO:70), or at a target sequence that, when translated, is at least 90 percent (e.g., at least 90 percent, at least 91 percent, at least 92 percent, at least 93 percent, at least 94 percent, at least 95 percent, at least 96 percent, at least 97 percent, at least 98 percent, at least 99 percent, 90 to 95 percent, 95 to 98 percent, or 98 to 99 percent) identical to an amino acid sequence as set forth herein (e.g., SEQ ID NO:55, SEQ ID NO:68, or SEQ ID NO:90).

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q −1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 2500 matches when aligned with the sequence set forth in SEQ ID NO:1 is 96.2 percent identical to the sequence set forth in SEQ ID NO:1 (i.e., 2500÷2600×100=96.2). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

Methods for selecting endogenous target sequences and generating TALE nucleases targeted to such sequences can be performed as described elsewhere. See, for example, PCT Publication No. WO 2011/072246, which is incorporated herein by reference in its entirety. In some embodiments, software that specifically identifies TALE nuclease recognition sites, such as TALE-NT 2.0 (Doyle et al., *Nucl Acids Res*, 40:W117-122, 2012) can be used.

This document therefore provides materials and methods for generating proteins, plants, plant parts, and plant cells with altered amino acid content as compared to a corresponding wild type protein, plant, plant part, or plant cell. In some embodiments, for example, a method as provided herein can include contacting a plant, plant part, or plant cell with a rare-cutting endonuclease (e.g., a TALE nuclease) targeted to a sequence within an exon of a gene endogenous to the plant, plant part, or plant cell, such that the rare-cutting endonuclease generates a double strand break at or near the sequence to which it is targeted; and then selecting a plant, plant part, or plant cell that contains a frameshift mutation within the exon, where the plant, plant part, or plant cell has an altered amino acid content as compared to a control plant, plant part, or plant cell in which the frameshift mutation was not introduced. In some cases, the method also can include evaluating alternate reading frames for the gene or the exon, to determine which reading frame would produce a protein having the desired amino acid content.

In some embodiments, the materials and methods provided herein can be used to generate a Gy4 protein having increased sulfur-containing amino acid content, by introducing a mutation into a Gy4 genomic sequence. The mutation can be a frameshift mutation of the size −3(N)−1 or +3(N)+2; such a frameshift within exon 3 of a Gy4 gene (SEQ ID NO:20), or within a sequence having at least 90% sequence identity to SEQ ID NO:20, can be particularly useful. In some cases, a frameshift mutation of the size −3(N)−1 or +3(N)+2 can be introduced (e.g., using one or more TALE nucleases) within a segment of a Gy4 gene that contains the sequence TCGTGACAGTGGAAGGAGGTCTCAGCGT-TATCAGCCCCA AGTGGCAAGAA (SEQ ID NO:94), or within a sequence having at least 90% identity to the sequence set forth in SEQ ID NO:94. In some cases, the frameshift mutation can result in production of a protein that contains the amino acid sequence set forth in SEQ ID NO:95, or an amino acid sequence having at least 90% identity to SEQ ID NO:95 (MKMKMKTKMM KMNKFPLTLLADQAMESVNKTRTRTKM-KINLVLVDQAKESVNKTRTRTRTKMK MKINLARKS-REWRSKKTQPRRPRQEEPRERGCETRNGVEENIC).

In some embodiments, the materials and methods provided herein can be used to generate an alpha gliadin protein having increased threonine content, by introducing a mutation into an alpha gliadin genomic sequence. The mutation can be a frameshift mutation of the size −3(N)−2 or +3(N)+1. In some cases, a frameshift mutation of the size −3(N)−2 or +3(N)+1 can be introduced (e.g., using one or more TALE nucleases) within a segment of the alpha gliadin gene that includes the sequence ATGAAGACCTTTCTCATCCTTGC CCTCCGTGCTATTGTAGCAACCACCGCCACAATT (SEQ ID NO:96), or within a sequence having at least 90% identity to SEQ ID NO:96. In some cases, the frameshift mutation can result in production of a protein that contains the amino acid sequence set forth in SEQ ID NO:97, or an amino acid sequence having at least 90% identity to SEQ ID NO:97 (TGPG LCPASTTAPV).

In some embodiments, the materials and methods provided herein can be used to generate a high molecular weight glutenin protein with increased threonine content, by introducing a mutation into a high molecular weight glutenin genomic sequence. The mutation can be a frameshift mutation of the size −3(N)−2 or +3(N)+1. In some cases, a frameshift mutation of the size −3(N)−2 or +3(N)+1 can be introduced (e.g., using one or more TALE nucleases) into a high molecular weight glutenin nucleotide sequence containing the sequence set forth in SEQ ID NO:70, or into a sequence having at least 90% identity to SEQ ID NO:70. The frameshift can occur at any suitable position within the high molecular weight glutenin sequence; in some cases, the frameshift mutation can encompass or follow the nucleotide at position 171 of SEQ ID NO:70. In some cases, the frameshift mutation can result in production of a high molecular weight glutenin protein containing the amino acid sequence set forth in SEQ ID NO:98, or an amino acid sequence with at least 90% identity to the sequence set forth in SEQ ID NO:98 (TDRTRAAIRTRATRLLQLIPC).

Further, the materials and methods provided herein can be used to generate a high molecular weight glutenin protein having increased lysine content, by introducing a mutation into a high molecular weight glutenin genomic sequence. The mutation can be a frameshift mutation of the size −3(N)−1 or +3(N)+2. In some cases, a frameshift mutation of the size −3(N)−2 or +3(N)+1 can be introduced (e.g., using one or more TALE nucleases) within a high molecular weight glutenin sequence as set forth in SEQ ID NO:70, or within a sequence having at least 90% identity to SEQ ID NO:70. The frameshift can be at any suitable position within the high molecular weight glutenin nucleotide sequence, and in some cases, the frameshift mutation can encompass or follow the nucleotide at position 348 of SEQ ID NO:70. In some cases, the frameshift mutation can result in production of a high molecular weight glutenin protein containing the amino acid sequence set forth in SEQ ID NO:99, or an amino acid sequence having at least 90% identity to SEQ ID NO:99 (LLCNSRDKGNQGTTQLLCSS).

The invention will be further described in the following examples, which do not limit the scope of the invention described in the claims.

EXAMPLES

Example 1

Searching for Alternative Reading Frames Within the Soybean Glycinin Gy4 Gene that Code for High Levels of Methionine and Lysine Amino Acids To increase methionine and lysine content in soybean, the storage protein Gy4 (Glyma10g04280) was targeted for modification. The amino acid sequence of the wild type Gy4 protein contains 1.5% methionine and cysteine residues (combined) and 5% lysine residues. The genomic sequence of the wild type Gy4 gene includes four exons and three introns (SEQ ID NO:1; FIG. 2). The approach illustrated in FIG. 1 was followed to generate a modified Gy4 protein with higher levels of lysine and methionine. The first step involved searching for alternative reading frames within the Gy4 coding sequence that contain high levels of methionine and lysine codons. To this end, the four exon sequences were translated in all three reading frames (FIGS. 3A and 3B). As expected, numerous stop codons were found in the −1 and −2 frames. However, there were regions between two stop codons with high levels of methionine and lysine codons. In particular, there was a stretch of codons in the −1 frame of exon 3 that encode 10 methionine and 22 lysine residues, whereas the same nucleotides within the normal reading frame encode 0 methionine and 8 lysine residues (FIG. 3B). If a frameshift mutation occurs within the wild type Gy4 gene at the start of the alternative reading frame containing high levels of methionine and lysine, then the resulting Gy4 protein will contain about 4.1% methionine and cysteine amino acids (combined level), and 9.1% lysine (FIG. 4). A list of changes to all essential amino acids is provided in TABLE 1.

TABLE 1

Percent of essential amino acids in Gy4 after introducing a −1 frameshift within exon 3
*Glycine max* Gy4 (FIG. 4)

| Essential Amino Acid | % amino acid in WT protein | −1 Frameshift (% of amino acid) | Change from WT (%) |
|---|---|---|---|
| His | 2.78 | 2.76 | −0.02 |
| Ile | 3.90 | 4.14 | 0.25 |
| Leu | 6.86 | 7.73 | 0.87 |
| Met | 0.37 | 3.31 | 2.94 |
| Phe | 2.60 | 2.21 | −0.39 |
| Thr | 3.71 | 5.52 | 1.81 |
| Trp | 1.11 | 0.83 | −0.28 |
| Val | 6.49 | 4.70 | −1.80 |
| Lys | 5.01 | 9.12 | 4.11 |

Thus, to generate a Gy4 protein with increased sulfur-containing amino acid content, mutations are introduced into the Gy4 genomic sequence such that one or more frameshift mutations of the size −3(N)−1 or +3(N)+2 occur, particularly within exon 3 (SEQ ID NO:20) or within a sequence having at least 90% identity to SEQ ID NO:20. In some cases, a TALE nuclease is used to introduce a frameshift mutation of the size −3(N)−1 or +3(N)+2 within Gy4 exon 3, where the mutation is within the sequence set forth in SEQ ID NO:94, or within a sequence having at least 90% identity to SEQ ID NO:94 (TCGTGACAGTGGAA GGAGGTCTCAGCGT-TATCAGCCCCAAGTGGCAAGAA). The frameshift mutation within Gy4 exon 3 may result in production of a Gy4 protein containing the amino acid sequence set forth in SEQ ID NO:95, or an amino acid sequence having at least 90% identity to SEQ ID NO:95 (MKMKMKTKMMKMNKFPLTLLADQAMESVNKTR-TRTKMKINLV LVDQAKESVNKTRTRTRTKMKMKIN-LARKSREWRSKKTQPRRPRQEEPRERGCE TRNGVEENIC).

Example 2

In Silico Design of Sequence-Specific Nucleases for Introducing a −1 Frameshift in Exon 3 of Gy4

Having identified a reading frame within Gy4 that codes for a high level of methionine and lysine amino acids, the next step is to design sequence-specific nucleases to introduce the appropriate −1 frameshift mutation. Ideally, the frameshift should occur upstream of the first codon of interest in the alternative reading frame. However, there are two restrictions to where the frameshift can occur. First, the frameshift must occur downstream of the stop codon within the frame of interest that precedes the codons of interest. Notably, the frameshift can occur within the stop codon, as long as the stop codon is disrupted during the process. The second restriction is that the downstream stop codon in the alternative frame of interest should ideally occur after the last intron. If a stop codon is created that is before intron sequences, then the mRNA transcript may be subject to nonsense-mediated decay. However, to circumvent nonsense-mediated decay, additional methods are described herein, including disruption of intron splicing through mutations, and restoration of the original reading frame.

To introduce the appropriate frameshift within Gy4, TALE nuclease pairs are designed to recognize sequence within exon 3 upstream of the codons of interest in the −1 frame (FIGS. 2 and 3). The desired deletion size should have a total length of −3(N)−1, where N is a whole number, including zero. The desired insertion size should have a total length of +3(N)+2 where N is a whole number, including zero. Notably, the deletion size does not typically exceed ~40 bp, as methionine codons may start to be deleted.

Example 3

Activity of Gy4 TALE Nuclease Pairs at Their Endogenous Target Sites in Soybean

To assess the activity of Gy4 TALE nuclease pairs at their endogenous target sequences, TALE nucleases are transformed into soybean protoplasts, and target sites are surveyed two days post transformation for mutations introduced by NHEJ. Methods for DNA transformation into soybean protoplasts are performed as described elsewhere (Dhir et al., *Plant Cell Rep*, 10: 39-43, 1991). Briefly, 15 days after pollination, immature soybean seedpods are sterilized by washing them successively on 100% ethanol, 50% bleach, and then sterile distilled water. Seedpod and seed coat are removed to isolate immature seeds. Protoplasts are then isolated from immature cotyledons by enzyme digestion for 16 hours using protocols described elsewhere (Dhir et al., supra).

TALE nuclease-encoding plasmids are next introduced into soybean protoplasts by PEG-mediated transformation (Yoo et al., *Nat Protoc*, 2:1565-1572, 2007). Forty-eight hours after treatment, the transformed protoplasts are harvested, and genomic DNA is prepared by a CTAB-based method (Murray and Thompson, *Nucl Acids Res*, 8: 4321-4325, 1980). Using the genomic DNA prepared from the protoplasts as a template, an approximately 600-bp fragment encompassing the TALE nuclease recognition site is amplified by PCR. The PCR product is then subjected to 454 pyro-sequencing. Sequencing reads with insertion/deletion (indel) mutations in the spacer region are considered as having been derived from imprecise repair of a cleaved TALE nuclease recognition site by NHEJ. Mutagenesis frequency is calculated as the number of sequencing reads with NHEJ mutations out of the total sequencing reads. The values are then normalized by the transformation efficiency. TALE nucleases showing activity are then used to create lines of soybean with mutations in Gy4 as described below.

Example 4

Regeneration of Soybean Plants Containing Frameshift Mutations Within Gy4

Soybean lines with mutations in one or both Gy4 alleles are generated. In particular, plant parts from soybean (e.g., immature embryos or embryogenic callus) are bombarded with plasmids encoding TALE nuclease pairs, or transformed via *Agrobacterium* with T-DNA encoding TALE nuclease pairs. Following bombardment, plant parts are placed on selection and regeneration media. Materials and methods for regeneration are used as previously described (Paz et al., *Plant Cell Res*, 25: 206-213, 2006). The plasmid and T-DNA contain a selectable marker (e.g., bialaphos) for conferring herbicide tolerance and to facilitate selection of transgenic plants. Transformation efficiencies are monitored using a control plasmid or T-DNA plasmid containing pNos:YFP and pNos:Bar. To visualize cells or plants that have stably integrated this control DNA into their genome, a fluorescent stereomicroscope is used that enables visualization of YFP being expressed in control cells that were transformed with pNos:YFP and are resistant to bialaphos.

After delivery of the Gy4-targeted TALE nuclease pair, soybean plants containing NHEJ mutations are regenerated. Plants containing a deletion of −3(N)−1 nucleotides or an insertion of +3(N)+2 nucleotides, where N is a whole number, including zero, are advanced to further phenotypic and genome engineering experiments.

Example 5

Improving Protein Stability and Folding By Restoring the Coding Sequence to the Original Reading Frame In some cases, it may be desirable to increase the folding, stability or expression of the modified protein. For example, the frameshift introduced into Gy4 may lead to nonsense-mediated decay of the mRNA transcript, thereby reducing Gy4 gene expression. Further, the modified amino acids within the Gy4 protein may reduce the folding potential at the C-terminus (folding potential can be calculated using publically available resources, such as that available at bip.weizmann.ac.il/fldbin/findex, and Prilusky et al., *Bioinformatics*, 21: 3435-3438, 2005).

Figure 5:
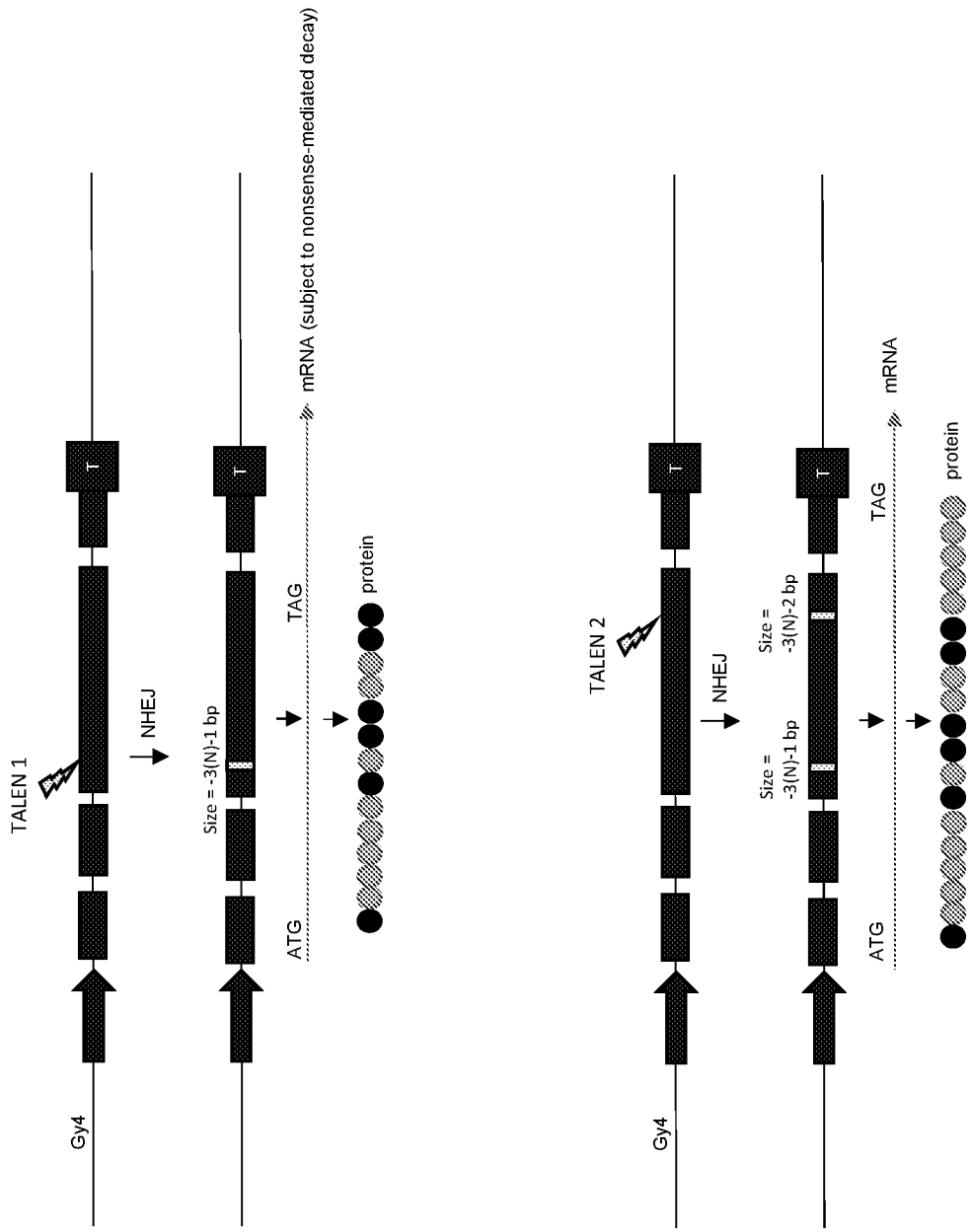
FIG. 5 is an illustration of an approach to increase protein expression and stability. After the first frameshift is introduced using transcription activator-like effector endonuclease (TALE nuclease) 1, the mRNA transcript may be subjected to nonsense-mediated decay (top). To prevent nonsense-mediated decay, and to increase protein stability, a second TALE nuclease 2 can be designed to re-introduce the wild type reading frame after the codons of interest (bottom).

One approach to increase the folding, stability and expression of Gy4 is to re-introduce the correct reading frame. This is accomplished by designing a second pair of TALE nucleases that target DNA sequence downstream of the codons of interest, but upstream of the newly-introduced stop codon (FIG. 5). The desired deletion size has a total length of −3(N)−2 where N is a whole number, including zero. The desired insertion size has a total length of +3(N)+1 where N is a whole number, including zero. In the exemplary process, the resulting Gy4 protein, harboring two frameshift mutations, contains about 3.3% methionine and cysteine, and 7.2% lysine (FIG. 6). A list of changes to all essential amino acids is provided in TABLE 2.

TABLE 2

Percent of essential amino acids in Gy4 after introducing a −1 frameshift and a second frameshift to restore the wild type reading frame.
*Glycine max* Gy4 (FIG. 6)

| Essential Amino Acid | % amino acid in WT protein | −1 Frameshift + restoration of WT coding sequence (% of amino acid) | Change from WT (%) |
|---|---|---|---|
| His | 2.78 | 2.41 | −0.38 |
| Ile | 3.90 | 3.89 | −0.01 |
| Leu | 6.86 | 7.96 | 1.10 |
| Met | 0.37 | 2.22 | 1.85 |
| Phe | 2.60 | 2.78 | 0.18 |
| Thr | 3.71 | 5.00 | 1.29 |
| Trp | 1.11 | 1.11 | 0.00 |
| Val | 6.49 | 6.85 | 0.36 |
| Lys | 5.01 | 7.22 | 2.21 |

Example 6

Figure 7:
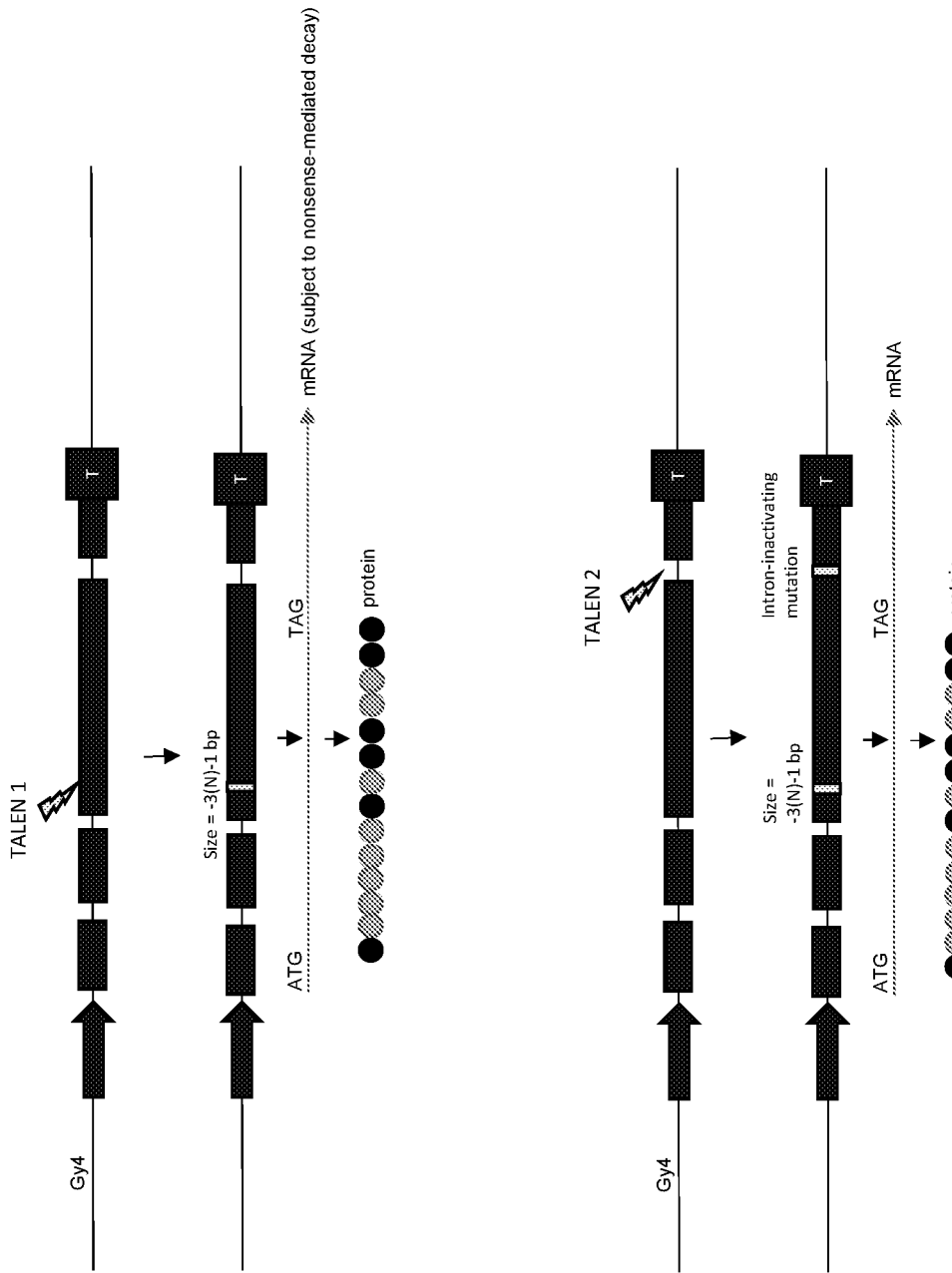
FIG. 7 is an illustration of an approach to circumvent nonsense-mediated decay in genes with premature stop codons. After the first frameshift is introduced using TALE nuclease 1 (top), the mRNA transcript may be subjected to nonsense-mediated decay. To prevent nonsense-mediated decay, a second TALE nuclease (TALE nuclease 2) is designed to mutate essential nucleotides involved in splicing (bottom).

Circumventing Nonsense-Mediated Decay of mRNA From Genes With a Stop Codon Before the Last Intron In some cases, it may be desirable to circumvent decreased protein expression due to nonsense-mediated decay. For example, the frameshift introduced into Gy4 in Example 1 results in a premature stop codon within exon 3. Nonsense-mediate decay is avoided by designing a second TALE nuclease pair to mutagenize splicing sequences within intron 3, thereby preventing processing of the last intron (FIG. 7). Examples of targets for mutation include, but are not limited to, i) the 5' splice donor site, ii) the 3' splice acceptor site, and iii) the branch site adenosine nucleotide. The resulting Gy4 gene, harboring two mutations (one frameshift mutation and one intron-inactivating mutation) produces a Gy4 protein that contains approximately 3.9% methionine and cysteine amino acids, and 8.8% lysine content. Further, the expression level of the modified Gy4 protein should be higher than a control that does not contain the intron-inactivating mutation (FIG. 4).

Example 7

Assessing the Phenotype of Modified Soybean Plants

Soybean plants containing frameshift mutations within the Gy4 gene are assessed for protein composition by two-dimensional protein analysis. Total soluble protein is isolated from mature seeds as described elsewhere (Schmidt and Herman, *Plant Biotech J*, 6:832-842, 2008). The soluble protein extract (150 mg) from both a modified and non-modified soybean plant is separated in the first dimension on 11-cm immobilized pH gradient gel strips (pH 3-10 nonlinear; Bio-Rad) and then in the second dimension by SDS-PAGE gels (8%-16% linear gradient). The resulting gels are subsequently stained with 0.1% (w/v) Coomassie Brilliant Blue R250 in 40% (v/v) methanol, 10% (v/v) acetic acid overnight, and then destained for approximately 3 h in 40% methanol, 10% acetic acid. The spots on the gels generated from modified plants are compared with the spots generated from wild type or control plants. Similar intensities in spots that represent the Gy4 protein between the modified and wild type or control plants suggest that the total level of methionine and lysine has improved in the modified plants.

In addition to two-dimensional protein analysis, the overall levels of methionine and cysteine in the mutant seed are determined by quantitation of hydrolyzed amino acids and free amino acids using a Waters Acquity ultraperformance liquid chromatography system (Schmidt, et al., *Plant Physiol*, 156: 330-345, 2011).

Example 8

Increasing Lysine and Threonine Content in Wheat By Targeting the Alpha Gliadins Wheat is deficient in the essential amino acids lysine and threonine. To increase the content of these amino acids in wheat grains, the coding sequence of an alpha gliadin gene was targeted. A representative alpha gliadin coding sequence from *Triticum aestivum* is shown in FIG. 8. The wild type protein contains 2.6% threonine and 0.7% lysine (FIG. 9). To determine if a frameshift can increase the content of threonine and lysine, the alpha gliadin coding sequence was translated in all three frames (FIG. 8). Surprisingly, frame −2 contained a very high number of threonine codons and a higher number of lysine codons, as compared to the wild type sequence. By introducing a frameshift mutation about 60 bp downstream of the start codon with a deletion or insertion size of −3(N)−2 or +3(N)+1, respectively, the threonine content increases from 2.6% to about 27.8%, and the lysine content increases from 0.7% to 2.3%. There are no introns within alpha gliadin genes; therefore, it is not necessary to introduce a second mutation downstream of the frameshift mutation. A list of changes to all essential amino acids is provided in TABLE 3.

TABLE 3

Percent of essential amino acids in a representative alpha gliadin protein after introducing a −2 frameshift near the beginning of the coding sequence
*Triticum aestivum* alpha gliadin (FIG. 9)

| Essential Amino Acid | % amino acid in WT protein | −2 Frameshift (% of amino acid) | Change from WT (%) |
|---|---|---|---|
| His | 1.68 | 0.75 | −0.93 |
| Ile | 5.39 | 8.65 | 3.26 |
| Leu | 7.74 | 4.51 | −3.23 |
| Met | 1.01 | 1.13 | 0.12 |
| Phe | 3.37 | 1.50 | −1.86 |
| Thr | 2.69 | 27.82 | 25.13 |
| Trp | 0.34 | 0.38 | 0.04 |
| Val | 5.39 | 4.14 | −1.25 |
| Lys | 0.67 | 2.26 | 1.58 |

Thus, to generate an alpha gliadin protein with increased threonine content, mutations are introduced into an alpha gliadin genomic sequence such that one or more frameshift mutations of the size −3(N)−2 or +3(N)+1 occur, particularly within an alpha gliadin gene containing the sequence set forth in SEQ ID NO:96 (ATGAAGACCTTTCT-CATCCTTG CCCTCCGTGCTATTGTAGCAAC-CACCGCCACAATT) or within a sequence having at least 90% identity to SEQ ID NO:96. In some cases, a TALE nuclease is used to introduce a frameshift mutation of the size −3(N)−2 or +3(N)+1 within the alpha gliadin sequence, where the mutation is within the sequence set forth in SEQ ID NO:96, or within a sequence having at least 90% identity to SEQ ID NO:96. The frameshift mutation may result in production of an alpha gliadin protein containing the amino acid sequence set forth in SEQ ID NO:97, or an amino acid sequence having at least 90% identity to SEQ ID NO:97 (TGPGLCPASTTAPV).

Example 9

Increasing Lysine and Threonine Content in Wheat By Targeting Glutenins

Increased lysine and threonine content also can be achieved by targeting the wheat glutenins. A representative high molecular weight glutenin subunit (Glu-1D-1d) gene from *Triticum aestivum* is shown in FIG. 10A. The wild type protein contains 2.9% threonine and 0.8% lysine (FIG. 11). To determine if a frameshift mutation can increase the content of threonine amino acids, the glutenin coding sequence was translated in all three reading frames (FIG. 10B), revealing that frame −2 contained a very high number of threonine codons. By introducing a frameshift mutation about 171 bp downstream of the start codon with a deletion or insertion size of −3(N)−2 or +3(N)+1, respectively, the amino acid content of threonine increases from 3.0% to about 21.4%. A list of changes to all essential amino acids is provided in TABLE 4.

TABLE 4

Percent of essential amino acids in a glutenin protein after introducing a −2 frameshift near the beginning of the coding sequence
*Triticum aestivum* glutenin (FIG. 11)

| Essential Amino Acid | % amino acid in WT protein | −2 Frameshift (% of amino acid) | Change from WT (%) |
|---|---|---|---|
| His | 0.47 | 0.12 | −0.35 |
| Ile | 0.47 | 2.22 | 1.75 |
| Leu | 4.72 | 4.44 | −0.27 |
| Met | 0.35 | 1.11 | 0.76 |
| Phe | 0.35 | 3.09 | 2.73 |
| Thr | 2.95 | 21.36 | 18.41 |
| Trp | 1.06 | 0.00 | −1.06 |
| Val | 2.48 | 4.57 | 2.09 |
| Lys | 0.83 | 0.86 | 0.04 |

Thus, to generate a high molecular weight glutenin protein with increased threonine content, mutations are introduced into a high molecular weight glutenin genomic sequence such that one or more frameshift mutations of the size −3(N)−2 or +3(N)+1 occur, particularly within SEQ ID NO:70 or within a sequence having at least 90% identity to SEQ ID NO:70. In some cases, a TALE nuclease is used to introduce a frameshift mutation of the size −3(N)−2 or +3(N)+1 within the a high molecular weight glutenin sequence, where the mutation is within the sequence set forth in SEQ ID NO:70, or within a sequence having at least 90% identity to SEQ ID NO:70, where the frameshift mutation encompasses or follows the nucleotide at position 171 of SEQ ID NO:70. The frameshift mutation may result in production of a high molecular weight glutenin protein containing the amino acid sequence set forth in SEQ ID NO:98, or an amino acid sequence having at least 90% identity to SEQ ID NO:98 (TDRTRAAIR-TRATRLLQLIPC).

The glutenin translation in all three reading frames (FIG. 10B) also showed that frame −1 contained a high number of lysine amino acids. By introducing a frameshift mutation about 348 bp downstream of the start codon with a deletion or insertion size of −3(N)−1 or +3(N)+2, respectively, the amino acid content of lysine increases from 0.8% to about 8.7%. A list of changes to all essential amino acids is provided in TABLE 5. Surprisingly, all essential amino acids, with the exception of tryptophan, increase in content within the protein produced from this −1 frameshift.

TABLE 5

Percent of essential amino acids in a glutenin protein after introducing a −1 frameshift near the beginning of the glutenin coding sequence
*Triticum aestivum* glutenin (FIG. 11)

| Essential Amino Acid | % amino acid in WT protein | −2 Frameshift (% of amino acid) | Change from WT (%) |
|---|---|---|---|
| His | 0.47 | 1.35 | 0.88 |
| Ile | 0.47 | 1.69 | 1.22 |
| Leu | 4.72 | 8.45 | 3.73 |
| Met | 0.35 | 0.68 | 0.32 |
| Phe | 0.35 | 1.35 | 1.00 |
| Thr | 2.95 | 4.73 | 1.78 |
| Trp | 1.06 | 0.34 | −0.72 |
| Val | 2.48 | 7.09 | 4.62 |
| Lys | 0.83 | 8.78 | 7.96 |

Thus, to generate a high molecular weight glutenin protein with increased lysine content, mutations are introduced into a high molecular weight glutenin genomic sequence such that one or more frameshift mutations of the size −3(N)−1 or +3(N)+2 occur, particularly within SEQ ID NO:70 or within a sequence having at least 90% identity to SEQ ID NO:70. In some cases, a TALE nuclease is used to introduce a frameshift mutation of the size −3(N)−1 or +3(N)+2 within the a high molecular weight glutenin sequence, where the mutation is within the sequence set forth in SEQ ID NO:70, or within a sequence having at least 90% identity to SEQ ID NO:70, where the frameshift mutation encompasses or follows the nucleotide at position 348 of SEQ ID NO:70. The frameshift mutation may result in production of a high molecular weight glutenin protein containing the amino acid sequence set forth in SEQ ID NO:99, or an amino acid sequence having at least 90% identity to SEQ ID NO:99 (LLCN-SRDKGNQGTTQLLCSS).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method, comprising:

evaluating a reading frame within a nucleic acid of a plant encoding a polypeptide, wherein the polypeptide includes a first amino acid content including an amount of a first amino acid of interest and an amount of a second amino acid of interest, evaluating a plurality of alternative reading frames within the polypeptide, wherein each alternative reading frame of the plurality of alternative reading frames is generated by a different respective frameshift mutation within the polypeptide, and each alternative reading frame of the plurality of alternative reading frames encodes a different respective amino acid content, selecting an alternative reading frame among the plurality of alternative reading frames that, when expressed, results in an increased content of the first amino acid of interest and the second amino acid of interest, as compared to the first amino acid content, and contacting the nucleic acid of the plant, a plant part of the plant, or a plant cell of the plant with a rare-cutting endonuclease to introduce the frameshift mutation associated with the selected alternative reading frame into the nucleic acid such that when the nucleic acid is expressed, a modified polypeptide having the increased content of the first amino acid of interest and the second amino acid of interest is expressed.

2. The method of claim 1, wherein the frameshift mutation associated with the selected alternative reading frame is of the size −3(N)−2, wherein the method further includes designing the rare-cutting endonuclease to target a sequence within the nucleic acid and to generate a double strand break to introduce the frameshift mutation associated with the selected alternative reading frame.

3. The method of claim 1, further including evaluating two or more reading frames within the nucleic acid and selecting two or more alternative reading frames among the plurality of alternative reading frames, wherein the frameshift mutation associated with the two or more selected alternative reading frames is of the size +3(N)+1, wherein the polypeptide is a protein of the plant and the nucleic acid is associated with a gene encoding the protein, and wherein contacting the nucleic acid with the rare-cutting endonuclease includes generating a double strand break at a target sequence within an exon of the gene encoding the protein and introducing the frameshift mutation associated with the two or more selected alternative reading frames.

4. The method of claim 1, wherein the rare-cutting endonuclease is a transcription activator-like effector endonuclease (TALE nuclease), a meganuclease, a zinc finger nuclease (ZFN), or a clustered regularly interspaced short palindromic repeats (CRISPR)/CRISPR-associated (Cas) nuclease reagent, the method further including, in response to contacting the nucleic acid with the rare-cutting endonuclease, producing the modified polypeptide having the increased content of the first amino acid of interest and the second amino acid of interest.

5. The method of claim 1, wherein the modified polypeptide encoded by the frameshift mutation associated with the selected alternative reading frame has increased sulfur-containing amino acid content as compared to the first amino acid content.

6. The method of claim 1, wherein the modified polypeptide encoded by the frameshift mutation associated with the selected alternative reading frame has increased threonine content as compared to the first amino acid content.

7. The method of claim 1, wherein the modified polypeptide encoded by the frameshift mutation associated with the selected alternative reading frame has increased lysine content as compared to the first amino acid content.

8. The method of claim 1, wherein the frameshift mutation associated with the selected alternative reading frame is a first frameshift mutation, the method further comprising introducing a second frameshift mutation into the nucleic acid encoding the modified polypeptide, wherein the first frameshift mutation and the second frameshift mutation result in a deletion or insertion of nucleotides, and wherein the size of the deletion or insertion is a multiple of 3.

9. A method, comprising:
selecting an alternative reading frame among a plurality of alternative reading frames of a gene endogenous to a plant, wherein each alternative reading frame of the plurality of alternative reading frames is generated by a different respective frameshift mutation, wherein the selected alternative reading frame encodes an amino acid sequence having increased content of a first amino acid of interest and a second amino acid of interest, as compared to a content of the first amino acid of interest and the second amino acid of interest in a corresponding wild type gene, and wherein the gene encodes a protein associated with the first amino acid of interest and the second amino acid of interest,
designing a rare-cutting endonuclease to target a sequence of the gene and to generate a double strand break at or near the sequence to introduce the frameshift mutation associated with the selected alternative reading frame, and
contacting the plant, a plant part of the plant, or a plant cell of the plant with the rare-cutting endonuclease to introduce the frameshift mutation associated with the selected alternative reading frame into a nucleic acid sequence of the plant, plant part, or plant cell such that when the nucleic acid sequence is expressed, the protein having the increased content of the first amino acid of interest and the second amino acid of interest is expressed.

10. The method of claim 9, wherein contacting the plant, plant part of the plant, or plant cell of the plant with the rare-cutting endonuclease includes generating the double strand break at the sequence that is within an exon of the gene encoding the protein and introducing the frameshift mutation without insertion of a transgene.

11. The method of claim 9, further including comparing a content of the first amino acid of interest and the second amino acid of interest that results from expression of each of the plurality of alternative reading frames and, based on the comparison, selecting the alternative reading frame that, when expressed, results in the highest content of the first amino acid of interest and the second amino acid of interest.

12. The method of claim 11, further including selecting the alternative reading frame in silico.

13. The method of claim 9, wherein the frameshift mutation is within a coding sequence of the gene, the method further including selecting the gene.

14. The method of claim 9, wherein the frameshift mutation is within the gene that encodes the protein comprising a seed storage protein or a protein expressed in leaf tissue.

15. The method of claim 9, further including, in response to contacting the nucleic acid sequence with the rare-cutting endonuclease, producing the protein having the increased content of the one or more amino acids of interest.

* * * * *

SEQUENCE LISTING

<160> NUMBER OF SEQ ID NOS: 99

<210> SEQ ID NO 1
<211> LENGTH: 2600
<212> TYPE: DNA
<213> ORGANISM: Glycine max

<400> SEQUENCE: 1

```
atggggaagc ccttcactct ctctctttct tcccttttgct tgctactctt gtcgagtgca      60
tgctttgcta ttagctccag caagctcaac gagtgccaac tcaacaacct caacgcgttg     120
gaacccgacc accgcgttga gtccgaaggt ggtttgattc aaacatggaa ctctcaacac     180
cctgagctga aatgcgccgg tgtcactgtt tccaaactca ccctcaaccg caatggcctc     240
cacttgccat cttactcacc ttatccccgg atgatcatca tcgcccaagg taatcatata     300
taaggagtgc ttcaacaca catatcagaa agagtatcac cagcatttct cagtgtatat     360
taatccattt gtcaccactt gttcaaattt caacatcaca ttaccataga tcatttacta     420
aagataataa tgatttaagt aaatagtatc tctatagtaa attttacatg attatttaac     480
tacaaattat tattattata tatagaatga ctttgttgac atatcaatca ccttaaaagt     540
tttattaagt tatatatatc aactaagata tctgattaaa taaaaatgtg attgtttttgt    600 ttggtgatga ttgatgtaca gggaaaggag cacttggagt tgcaattcca ggatgtcctg     660
agacgtttga ggagccacaa gaacaatcaa acagaagagg ctcaaggtcg cagaagcagc     720
agctacagga cagtcaccag aagattcgtc acttcaatga aggagacgta ctcgtgattc     780
ctcctggtgt tccttactgg acctataaca ctggcgatga accagttgtt gccatcagtc     840
ttcttgacac ctctaacttc aataaccagc ttgatcaaac ccctagggta attatcaatt     900
caatttcatt tactattaac aaaaaccatg ttctcctcac ttgttaattt tttcactttc     960
aggtatttta ccttgctggg aacccagata tagagtaccc agagaccatg caacaacaac    1020
aacagcagaa aagtcatggt ggacgcaagc aggggcaaca ccagcaggag gaagaggaag    1080
aaggtggcag cgtgctcagt ggcttcagca aacacttctt ggcacaatcc ttcaacacca    1140
acgaggacat agctgagaaa cttcagtctc cagacgacga aaggaagcag atcgtgacag    1200
tggaaggagg tctcagcgtt atcagcccca agtggcaaga caacaagat gaagatgaag    1260 atgaagacga agatgatgaa gatgaacaaa ttccctctca ccctcctcgc cgaccaagcc    1320
atggaaagcg tgaacaagac gaggacgagg acgaagatga agataaacct cgtcctagtc    1380
gaccaagcca aggaaagcgt gaacaagacc aggaccagga cgaggacgaa gatgaagatg    1440
aagatcaacc tcgcaagagc cgcgaatgga gatcgaaaaa gacacaaccc agaagaccta    1500
```

```
gacaagaaga accacgtgaa agaggatgcg agacaagaaa cggggttgag gaaaatatct   1560
gcaccttgaa gcttcacgag aacattgctc gcccttcacg cgctgacttc tacaacccta   1620
aagctggtcg cattagtacc ctcaacagcc tcaccctccc agccctccgc caattccaac   1680
tcagtgccca atatgttgtc ctctacaagg tatgtaattc acctcattca tattactaag   1740
taatcaacat gaaactaata tacgtacata cttacacatc taccagtaat ttttccgtgg   1800
atattcaatt gtcaattagt ctatcttgag aaaattaaga aataaaaaga aagcacaaaa   1860
gggaaaaatc tttatgtcat aaatcatatg atataataat ttagaagaca tataaaaatg   1920
tcagtaagta tgttgtaggg ttggattcct ttaaatgtca ttaaaatatc atttgatatg   1980
ggtaattctt tagtgattct ctaggggtag ttgaactgta atgtattata attgtgcatt   2040
gatttttatg agttactttta acatgtcaat gaagacttat ttgataataa ttatagttac   2100
ttgttggttc tactactttt aataaaaaaa taataaaaat attggtgtaa atatataata   2160
tataataata atgatgatga tacgtaacac atgttattat atccatgcag aatggaattt   2220
actctccaca ttggaatctg aatgcaaaca gtgtgatcta tgtgactcga ggacaaggaa   2280
aggttagagt tgtgaactgc caagggaatg cagtgttcga cggtgagctt aggaggggac   2340
aattgctggt ggtaccacag aacttcgtgg tggcggagca agccgagaa caaggattcg   2400 aatacatagt attcaagaca caccacaacg cagtcactag ctacttgaag gatgtgttta   2460
gggcaattcc ctcagaggtt cttgcccatt cttacaacct tcgacagagt caagtgtctg   2520
agcttaagta tgaaggaaat tggggtcctt tggtcaaccc tgagtctcaa caaggctcac   2580
cccgtgttaa agtcgcataa                                              2600

<210> SEQ ID NO 2
<211> LENGTH: 289
<212> TYPE: DNA
<213> ORGANISM: Glycine max

<400> SEQUENCE: 2
atggggaagc ccttcactct ctctctttct tcccttttgct tgctactctt gtcgagtgca     60
tgctttgcta ttagctccag caagctcaac gagtgccaac tcaacaacct caacgcgttg    120
gaacccgacc accgcgttga gtccgaaggt ggtttgattc aaacatggaa ctctcaacac    180
cctgagctga aatgcgccgg tgtcactgtt tccaaactca ccctcaaccg caatggcctc    240
cacttgccat cttactcacc ttatccccgg atgatcatca tcgcccaag               289

<210> SEQ ID NO 3
<211> LENGTH: 51
<212> TYPE: PRT
<213> ORGANISM: Artificial
<220> FEATURE:
<223> OTHER INFORMATION: synthetic polypeptide

<400> SEQUENCE: 3

Trp Gly Ser Pro Ser Leu Ser Leu Phe Leu Pro Phe Ala Cys Tyr Ser
1               5                   10                  15

Cys Arg Val His Ala Leu Leu Leu Ala Pro Ala Ser Ser Thr Ser Ala
            20                  25                  30

Asn Ser Thr Thr Ser Thr Arg Trp Asn Pro Thr Thr Ala Leu Ser Pro
        35                  40                  45

Lys Val Val
    50
```

```
<210> SEQ ID NO 4
<211> LENGTH: 10
<212> TYPE: PRT
<213> ORGANISM: Artificial
<220> FEATURE:
<223> OTHER INFORMATION: synthetic polypeptide

<400> SEQUENCE: 4

Phe Lys His Gly Thr Leu Asn Thr Leu Ser
1               5                   10

<210> SEQ ID NO 5
<211> LENGTH: 27
<212> TYPE: PRT
<213> ORGANISM: Artificial
<220> FEATURE:
<223> OTHER INFORMATION: synthetic polypeptide

<400> SEQUENCE: 5

Asn Ala Pro Val Ser Leu Phe Pro Asn Ser Pro Ser Thr Ala Met Ala
1               5                   10                  15

Ser Thr Cys His Leu Thr His Leu Ile Pro Gly
            20                  25

<210> SEQ ID NO 6
<211> LENGTH: 5
<212> TYPE: PRT
<213> ORGANISM: Artificial
<220> FEATURE:
<223> OTHER INFORMATION: synthetic polypeptide

<400> SEQUENCE: 6

Ser Ser Ser Pro Lys
1               5

<210> SEQ ID NO 7
<211> LENGTH: 23
<212> TYPE: PRT
<213> ORGANISM: Artificial
<220> FEATURE:
<223> OTHER INFORMATION: synthetic polypeptide

<400> SEQUENCE: 7

Gly Glu Ala Leu His Ser Leu Ser Phe Phe Pro Leu Leu Ala Thr Leu
1               5                   10                  15

Val Glu Cys Met Leu Cys Tyr
            20

<210> SEQ ID NO 8
<211> LENGTH: 21
<212> TYPE: PRT
<213> ORGANISM: Artificial
<220> FEATURE:
<223> OTHER INFORMATION: synthetic polypeptide

<400> SEQUENCE: 8

Leu Gln Gln Ala Gln Arg Val Pro Thr Gln Gln Pro Gln Arg Val Gly
1               5                   10                  15

Thr Arg Pro Pro Arg
            20

<210> SEQ ID NO 9
<211> LENGTH: 14
<212> TYPE: PRT
<213> ORGANISM: Artificial
<220> FEATURE:
```

<223> OTHER INFORMATION: synthetic polypeptide

<400> SEQUENCE: 9

Val Arg Arg Trp Phe Asp Ser Asn Met Glu Leu Ser Thr Pro
1               5                   10

<210> SEQ ID NO 10
<211> LENGTH: 34
<212> TYPE: PRT
<213> ORGANISM: Artificial
<220> FEATURE:
<223> OTHER INFORMATION: synthetic polypeptide

<400> SEQUENCE: 10

Ala Glu Met Arg Arg Cys His Cys Phe Gln Thr His Pro Gln Pro Gln
1               5                   10                  15

Trp Pro Pro Leu Ala Ile Leu Leu Thr Leu Ser Pro Asp Asp His His
            20                  25                  30

Arg Pro

<210> SEQ ID NO 11
<211> LENGTH: 95
<212> TYPE: PRT
<213> ORGANISM: Glycine max

<400> SEQUENCE: 11

Gly Lys Pro Phe Thr Leu Ser Leu Ser Ser Leu Cys Leu Leu Leu
1               5                   10                  15

Ser Ser Ala Cys Phe Ala Ile Ser Ser Ser Lys Leu Asn Glu Cys Gln
            20                  25                  30

Leu Asn Asn Leu Asn Ala Leu Glu Pro Asp His Arg Val Glu Ser Glu
        35                  40                  45

Gly Gly Leu Ile Gln Thr Trp Asn Ser Gln His Pro Glu Leu Lys Cys
    50                  55                  60

Ala Gly Val Thr Val Ser Lys Leu Thr Leu Asn Arg Asn Gly Leu His
65                  70                  75                  80

Leu Pro Ser Tyr Ser Pro Tyr Pro Arg Met Ile Ile Ile Ala Gln
                85                  90                  95

<210> SEQ ID NO 12
<211> LENGTH: 266
<212> TYPE: DNA
<213> ORGANISM: Glycine max

<400> SEQUENCE: 12
ggaaaggagc acttggagtt gcaattccag gatgtcctga gacgtttgag gagccacaag      60
aacaatcaaa cagaagaggc tcaaggtcgc agaagcagca gctacaggac agtcaccaga     120
agattcgtca cttcaatgaa ggagacgtac tcgtgattcc tcctggtgtt ccttactgga     180
cctataacac tggcgatgaa ccagttgttg ccatcagtct tcttgacacc tctaacttca     240
ataaccagct tgatcaaacc cctagg                                          266

<210> SEQ ID NO 13
<211> LENGTH: 50
<212> TYPE: PRT
<213> ORGANISM: Artificial
<220> FEATURE:
<223> OTHER INFORMATION: synthetic polypeptide

<400> SEQUENCE: 13

```
Lys Glu His Leu Glu Leu Gln Phe Gln Asp Val Leu Arg Arg Leu Arg
1               5                   10                  15

Ser His Lys Asn Asn Gln Thr Glu Ala Gly Arg Ser Ser
            20                  25                  30

Ser Tyr Arg Thr Val Thr Arg Arg Phe Val Thr Ser Met Lys Glu Thr
        35                  40                  45

Tyr Ser
    50

<210> SEQ ID NO 14
<211> LENGTH: 36
<212> TYPE: PRT
<213> ORGANISM: Artificial
<220> FEATURE:
<223> OTHER INFORMATION: synthetic polypeptide

<400> SEQUENCE: 14

Phe Leu Leu Val Phe Leu Thr Gly Pro Ile Thr Leu Ala Met Asn Gln
1               5                   10                  15

Leu Leu Pro Ser Val Phe Leu Thr Pro Leu Thr Ser Ile Thr Ser Leu
            20                  25                  30

Ile Lys Pro Leu
        35

<210> SEQ ID NO 15
<211> LENGTH: 12
<212> TYPE: PRT
<213> ORGANISM: Artificial
<220> FEATURE:
<223> OTHER INFORMATION: synthetic polypeptide

<400> SEQUENCE: 15

Glu Arg Ser Thr Trp Ser Cys Asn Ser Arg Met Ser
1               5                   10

<210> SEQ ID NO 16
<211> LENGTH: 29
<212> TYPE: PRT
<213> ORGANISM: Artificial
<220> FEATURE:
<223> OTHER INFORMATION: synthetic polypeptide

<400> SEQUENCE: 16

Gly Ala Thr Arg Thr Ile Lys Gln Lys Arg Leu Lys Val Ala Glu Ala
1               5                   10                  15

Ala Ala Thr Gly Gln Ser Pro Glu Asp Ser Ser Leu Gln
            20                  25

<210> SEQ ID NO 17
<211> LENGTH: 15
<212> TYPE: PRT
<213> ORGANISM: Artificial
<220> FEATURE:
<223> OTHER INFORMATION: synthetic polypeptide

<400> SEQUENCE: 17

Arg Arg Arg Thr Arg Asp Ser Ser Trp Cys Ser Leu Leu Asp Leu
1               5                   10                  15

<210> SEQ ID NO 18
<211> LENGTH: 8
<212> TYPE: PRT
<213> ORGANISM: Artificial
<220> FEATURE:
```

<223> OTHER INFORMATION: synthetic polypeptide

<400> SEQUENCE: 18

Thr Ser Cys Cys His Gln Ser Ser
1               5

<210> SEQ ID NO 19
<211> LENGTH: 88
<212> TYPE: PRT
<213> ORGANISM: Glycine max

<400> SEQUENCE: 19

Lys Gly Ala Leu Gly Val Ala Ile Pro Gly Cys Pro Glu Thr Phe Glu
1               5                   10                  15

Glu Pro Gln Glu Gln Ser Asn Arg Arg Gly Ser Arg Ser Gln Lys Gln
            20                  25                  30

Gln Leu Gln Asp Ser His Gln Lys Ile Arg His Phe Asn Glu Gly Asp
        35                  40                  45

Val Leu Val Ile Pro Pro Gly Val Pro Tyr Trp Thr Tyr Asn Thr Gly
    50                  55                  60

Asp Glu Pro Val Val Ala Ile Ser Leu Leu Asp Thr Ser Asn Phe Asn
65                  70                  75                  80

Asn Gln Leu Asp Gln Thr Pro Arg
                85

<210> SEQ ID NO 20
<211> LENGTH: 747
<212> TYPE: DNA
<213> ORGANISM: Glycine max

<400> SEQUENCE: 20
gtattttacc ttgctgggaa cccagatata gagtacccag agaccatgca acaacaacaa      60
cagcagaaaa gtcatggtgg acgcaagcag gggcaacacc agcaggagga agaggaagaa     120
ggtggcagcg tgctcagtgg cttcagcaaa cacttcttgg cacaatcctt caacaccaac     180
gaggacatag ctgagaaact tcagtctcca gacgacgaaa ggaagcagat cgtgacagtg     240
gaaggaggtc tcagcgttat cagccccaag tggcaagaac aacaagatga agatgaagat     300
gaagacgaag atgatgaaga tgaacaaatt ccctctcacc ctcctcgccg accaagccat     360
ggaaagcgtg aacaagacga ggacgaggac gaagatgaag ataaacctcg tcctagtcga     420
ccaagccaag gaaagcgtga acaagaccag gaccaggacg aggacgaaga tgaagatgaa     480
gatcaacctc gcaagagccg cgaatggaga tcgaaaaaga cacaacccag aagacctaga     540
caagaagaac cacgtgaaag aggatgcgag acaagaaacg gggttgagga aaatatctgc     600
accttgaagc ttcacgagaa cattgctcgc ccttcacgcg ctgacttcta caaccctaaa     660
gctggtcgca ttagtaccct caacagcctc accctcccag ccctccgcca attccaactc     720
agtgcccaat atgttgtcct ctacaag                                        747

<210> SEQ ID NO 21
<211> LENGTH: 9
<212> TYPE: PRT
<213> ORGANISM: Artificial
<220> FEATURE:
<223> OTHER INFORMATION: synthetic polypeptide

<400> SEQUENCE: 21

Tyr Phe Thr Leu Leu Gly Thr Gln Ile
1               5

<210> SEQ ID NO 22
<211> LENGTH: 52
<212> TYPE: PRT
<213> ORGANISM: Artificial
<220> FEATURE:
<223> OTHER INFORMATION: synthetic polypeptide

<400> SEQUENCE: 22

Ser Thr Gln Arg Pro Cys Asn Asn Asn Ser Arg Lys Val Met Val
1               5                   10                  15

Asp Ala Ser Arg Gly Asn Thr Ser Arg Arg Lys Arg Lys Lys Val Ala
            20                  25                  30

Ala Cys Ser Val Ala Ser Ala Asn Thr Ser Trp His Asn Pro Ser Thr
        35                  40                  45

Pro Thr Arg Thr
    50

<210> SEQ ID NO 23
<211> LENGTH: 14
<212> TYPE: PRT
<213> ORGANISM: Artificial
<220> FEATURE:
<223> OTHER INFORMATION: synthetic polypeptide

<400> SEQUENCE: 23

Leu Arg Asn Phe Ser Leu Gln Thr Thr Lys Gly Ser Arg Ser
1               5                   10

<210> SEQ ID NO 24
<211> LENGTH: 123
<212> TYPE: PRT
<213> ORGANISM: Artificial
<220> FEATURE:
<223> OTHER INFORMATION: synthetic polypeptide

<400> SEQUENCE: 24

Gln Trp Lys Glu Val Ser Ala Leu Ser Ala Pro Ser Gly Lys Asn Asn
1               5                   10                  15

Lys Met Lys Met Lys Met Lys Thr Lys Met Met Lys Met Asn Lys Phe
            20                  25                  30

Pro Leu Thr Leu Leu Ala Asp Gln Ala Met Glu Ser Val Asn Lys Thr
        35                  40                  45

Arg Thr Arg Thr Lys Met Lys Ile Asn Leu Val Leu Val Asp Gln Ala
    50                  55                  60

Lys Glu Ser Val Asn Lys Thr Arg Thr Arg Thr Arg Thr Lys Met Lys
65                  70                  75                  80

Met Lys Ile Asn Leu Ala Arg Ala Ala Asn Gly Asp Arg Lys Arg His
                85                  90                  95

Asn Pro Glu Asp Leu Asp Lys Lys Asn His Val Lys Glu Asp Ala Arg
            100                 105                 110

Gln Glu Thr Gly Leu Arg Lys Ile Ser Ala Pro
        115                 120

<210> SEQ ID NO 25
<211> LENGTH: 46
<212> TYPE: PRT
<213> ORGANISM: Artificial
<220> FEATURE:
<223> OTHER INFORMATION: synthetic polypeptide

<400> SEQUENCE: 25

```
Ser Phe Thr Arg Thr Leu Leu Ala Leu His Ala Leu Thr Ser Thr Thr
1               5                   10                  15

Leu Lys Leu Val Ala Leu Val Pro Ser Thr Ala Ser Pro Ser Gln Pro
            20                  25                  30

Ser Ala Asn Ser Asn Ser Val Pro Asn Met Leu Ser Ser Thr
        35                  40                  45

<210> SEQ ID NO 26
<211> LENGTH: 63
<212> TYPE: PRT
<213> ORGANISM: Artificial
<220> FEATURE:
<223> OTHER INFORMATION: synthetic polypeptide

<400> SEQUENCE: 26

Ile Leu Pro Cys Trp Glu Pro Arg Tyr Arg Val Pro Arg Asp His Ala
1               5                   10                  15

Thr Thr Thr Thr Ala Glu Lys Ser Trp Trp Thr Gln Ala Gly Ala Thr
            20                  25                  30

Pro Ala Gly Gly Arg Gly Arg Arg Trp Gln Arg Ala Gln Trp Leu Gln
        35                  40                  45

Gln Thr Leu Leu Gly Thr Ile Leu Gln His Gln Arg Gly His Ser
    50                  55                  60

<210> SEQ ID NO 27
<211> LENGTH: 31
<212> TYPE: PRT
<213> ORGANISM: Artificial
<220> FEATURE:
<223> OTHER INFORMATION: synthetic polypeptide

<400> SEQUENCE: 27

Glu Thr Ser Val Ser Arg Arg Arg Lys Glu Ala Asp Arg Asp Ser Gly
1               5                   10                  15

Arg Arg Ser Gln Arg Tyr Gln Pro Gln Val Ala Arg Thr Thr Arg
            20                  25                  30

<210> SEQ ID NO 28
<211> LENGTH: 15
<212> TYPE: PRT
<213> ORGANISM: Artificial
<220> FEATURE:
<223> OTHER INFORMATION: synthetic polypeptide

<400> SEQUENCE: 28

Thr Asn Ser Leu Ser Pro Ser Ser Pro Thr Lys Pro Trp Lys Ala
1               5                   10                  15

<210> SEQ ID NO 29
<211> LENGTH: 8
<212> TYPE: PRT
<213> ORGANISM: Artificial
<220> FEATURE:
<223> OTHER INFORMATION: synthetic polypeptide

<400> SEQUENCE: 29

Thr Arg Arg Gly Arg Gly Arg Arg
1               5

<210> SEQ ID NO 30
<211> LENGTH: 7
<212> TYPE: PRT
<213> ORGANISM: Artificial
```

```
<220> FEATURE:
<223> OTHER INFORMATION: synthetic polypeptide

<400> SEQUENCE: 30

Ser Thr Lys Pro Arg Lys Ala
1               5

<210> SEQ ID NO 31
<211> LENGTH: 10
<212> TYPE: PRT
<213> ORGANISM: Artificial
<220> FEATURE:
<223> OTHER INFORMATION: synthetic polypeptide

<400> SEQUENCE: 31

Thr Arg Pro Gly Pro Gly Arg Gly Arg Arg
1               5                   10

<210> SEQ ID NO 32
<211> LENGTH: 19
<212> TYPE: PRT
<213> ORGANISM: Artificial
<220> FEATURE:
<223> OTHER INFORMATION: synthetic polypeptide

<400> SEQUENCE: 32

Arg Ser Thr Ser Gln Glu Pro Arg Met Glu Ile Glu Lys Asp Thr Thr
1               5                   10                  15

Gln Lys Thr

<210> SEQ ID NO 33
<211> LENGTH: 5
<212> TYPE: PRT
<213> ORGANISM: Artificial
<220> FEATURE:
<223> OTHER INFORMATION: synthetic polypeptide

<400> SEQUENCE: 33

Thr Arg Arg Thr Thr
1               5

<210> SEQ ID NO 34
<211> LENGTH: 9
<212> TYPE: PRT
<213> ORGANISM: Artificial
<220> FEATURE:
<223> OTHER INFORMATION: synthetic polypeptide

<400> SEQUENCE: 34

Lys Arg Met Arg Asp Lys Lys Arg Gly
1               5

<210> SEQ ID NO 35
<211> LENGTH: 18
<212> TYPE: PRT
<213> ORGANISM: Artificial
<220> FEATURE:
<223> OTHER INFORMATION: synthetic polypeptide

<400> SEQUENCE: 35

Gly Lys Tyr Leu His Leu Glu Ala Ser Arg Glu His Cys Ser Pro Phe
1               5                   10                  15

Thr Arg

<210> SEQ ID NO 36
```

```
<211> LENGTH: 4
<212> TYPE: PRT
<213> ORGANISM: Artificial
<220> FEATURE:
<223> OTHER INFORMATION: synthetic polypeptide

<400> SEQUENCE: 36

Leu Leu Gln Pro
1

<210> SEQ ID NO 37
<211> LENGTH: 4
<212> TYPE: PRT
<213> ORGANISM: Artificial
<220> FEATURE:
<223> OTHER INFORMATION: synthetic polypeptide

<400> SEQUENCE: 37

Ser Trp Ser His
1

<210> SEQ ID NO 38
<211> LENGTH: 24
<212> TYPE: PRT
<213> ORGANISM: Artificial
<220> FEATURE:
<223> OTHER INFORMATION: synthetic polypeptide

<400> SEQUENCE: 38

Tyr Pro Gln Gln Pro His Pro Pro Ser Pro Pro Ile Pro Thr Gln
1               5                   10                  15

Cys Pro Ile Cys Cys Pro Leu Gln
            20

<210> SEQ ID NO 39
<211> LENGTH: 248
<212> TYPE: PRT
<213> ORGANISM: Glycine max

<400> SEQUENCE: 39

Phe Tyr Leu Ala Gly Asn Pro Asp Ile Glu Tyr Pro Glu Thr Met Gln
1               5                   10                  15

Gln Gln Gln Gln Gln Lys Ser His Gly Gly Arg Lys Gln Gly Gln His
                20                  25                  30

Gln Gln Glu Glu Glu Glu Glu Gly Gly Ser Val Leu Ser Gly Phe Ser
            35                  40                  45

Lys His Phe Leu Ala Gln Ser Phe Asn Thr Asn Glu Asp Ile Ala Glu
        50                  55                  60

Lys Leu Gln Ser Pro Asp Asp Glu Arg Lys Gln Ile Val Thr Val Glu
65                  70                  75                  80

Gly Gly Leu Ser Val Ile Ser Pro Lys Trp Gln Glu Gln Asp Glu
                85                  90                  95

Asp Glu Asp Glu Asp Glu Asp Glu Asp Gln Ile Pro Ser His
            100                 105                 110

Pro Pro Arg Arg Pro Ser His Gly Lys Arg Glu Gln Asp Glu Asp Glu
        115                 120                 125

Asp Glu Asp Glu Asp Lys Pro Arg Pro Ser Arg Pro Ser Gln Gly Lys
    130                 135                 140

Arg Glu Gln Asp Gln Asp Gln Asp Glu Asp Glu Asp Glu Asp Glu Asp
145                 150                 155                 160

Gln Pro Arg Lys Ser Arg Glu Trp Arg Ser Lys Lys Thr Gln Pro Arg
```

165                 170                 175

Arg Pro Arg Gln Glu Glu Pro Arg Glu Arg Gly Cys Glu Thr Arg Asn
            180                 185                 190

Gly Val Glu Glu Asn Ile Cys Thr Leu Lys Leu His Glu Asn Ile Ala
        195                 200                 205

Arg Pro Ser Arg Ala Asp Phe Tyr Asn Pro Lys Ala Gly Arg Ile Ser
    210                 215                 220

Thr Leu Asn Ser Leu Thr Leu Pro Ala Leu Arg Gln Phe Gln Leu Ser
225                 230                 235                 240

Ala Gln Tyr Val Val Leu Tyr Lys
                245

<210> SEQ ID NO 40
<211> LENGTH: 390
<212> TYPE: DNA
<213> ORGANISM: Glycine max

<400> SEQUENCE: 40
aatggaattt actctccaca ttggaatctg aatgcaaaca gtgtgatcta tgtgactcga      60
ggacaaggaa aggttagagt tgtgaactgc aagggaatg cagtgttcga cggtgagctt     120
aggaggggac aattgctggt ggtaccacag aacttcgtgg tggcggagca agccggagaa    180
caaggattcg aatacatagt attcaagaca caccacaacg cagtcactag ctacttgaag    240
gatgtgttta gggcaattcc ctcagaggtt cttgcccatt cttacaacct tcgacagagt    300
caagtgtctg agcttaagta tgaaggaaat tggggtcctt tggtcaaccc tgagtctcaa    360
caaggctcac cccgtgttaa agtcgcataa                                     390

<210> SEQ ID NO 41
<211> LENGTH: 9
<212> TYPE: PRT
<213> ORGANISM: Artificial
<220> FEATURE:
<223> OTHER INFORMATION: synthetic polypeptide

<400> SEQUENCE: 41

Met Glu Phe Thr Leu His Ile Gly Ile
1               5

<210> SEQ ID NO 42
<211> LENGTH: 4
<212> TYPE: PRT
<213> ORGANISM: Artificial
<220> FEATURE:
<223> OTHER INFORMATION: synthetic polypeptide

<400> SEQUENCE: 42

Met Gln Thr Val
1

<210> SEQ ID NO 43
<211> LENGTH: 9
<212> TYPE: PRT
<213> ORGANISM: Artificial
<220> FEATURE:
<223> OTHER INFORMATION: synthetic polypeptide

<400> SEQUENCE: 43

Leu Glu Asp Lys Glu Arg Leu Glu Leu
1               5

```
<210> SEQ ID NO 44
<211> LENGTH: 37
<212> TYPE: PRT
<213> ORGANISM: Artificial
<220> FEATURE:
<223> OTHER INFORMATION: synthetic polypeptide

<400> SEQUENCE: 44

Thr Ala Lys Gly Met Gln Cys Ser Thr Val Ser Leu Gly Gly Asp Asn
1               5                   10                  15

Cys Trp Trp Tyr His Arg Thr Ser Trp Trp Arg Ser Lys Pro Glu Asn
            20                  25                  30

Lys Asp Ser Asn Thr
        35

<210> SEQ ID NO 45
<211> LENGTH: 12
<212> TYPE: PRT
<213> ORGANISM: Artificial
<220> FEATURE:
<223> OTHER INFORMATION: synthetic polypeptide

<400> SEQUENCE: 45

Tyr Ser Arg His Thr Thr Thr Gln Ser Leu Ala Thr
1               5                   10

<210> SEQ ID NO 46
<211> LENGTH: 50
<212> TYPE: PRT
<213> ORGANISM: Artificial
<220> FEATURE:
<223> OTHER INFORMATION: synthetic polypeptide

<400> SEQUENCE: 46

Arg Met Cys Leu Gly Gln Phe Pro Gln Arg Phe Leu Pro Ile Leu Thr
1               5                   10                  15

Thr Phe Asp Arg Val Lys Cys Leu Ser Leu Ser Met Lys Glu Ile Gly
            20                  25                  30

Val Leu Trp Ser Thr Leu Ser Leu Asn Lys Ala His Pro Val Leu Lys
        35                  40                  45

Ser His
    50

<210> SEQ ID NO 47
<211> LENGTH: 24
<212> TYPE: PRT
<213> ORGANISM: Artificial
<220> FEATURE:
<223> OTHER INFORMATION: synthetic polypeptide

<400> SEQUENCE: 47

Trp Asn Leu Leu Ser Thr Leu Glu Ser Glu Cys Lys Gln Cys Asp Leu
1               5                   10                  15

Cys Asp Ser Arg Thr Arg Lys Gly
            20

<210> SEQ ID NO 48
<211> LENGTH: 12
<212> TYPE: PRT
<213> ORGANISM: Artificial
<220> FEATURE:
<223> OTHER INFORMATION: synthetic polypeptide

<400> SEQUENCE: 48
```

Ser Cys Glu Leu Pro Arg Glu Cys Ser Val Arg Arg
1               5                   10

<210> SEQ ID NO 49
<211> LENGTH: 35
<212> TYPE: PRT
<213> ORGANISM: Artificial
<220> FEATURE:
<223> OTHER INFORMATION: synthetic polypeptide

<400> SEQUENCE: 49

Glu Gly Thr Ile Ala Gly Gly Thr Thr Glu Leu Arg Gly Gly Gly Ala
1               5                   10                  15

Ser Arg Arg Thr Arg Ile Arg Ile His Ser Ile Gln Asp Thr Pro Gln
            20                  25                  30

Arg Ser His
        35

<210> SEQ ID NO 50
<211> LENGTH: 6
<212> TYPE: PRT
<213> ORGANISM: Artificial
<220> FEATURE:
<223> OTHER INFORMATION: synthetic polypeptide

<400> SEQUENCE: 50

Leu Leu Glu Gly Cys Val
1               5

<210> SEQ ID NO 51
<211> LENGTH: 19
<212> TYPE: PRT
<213> ORGANISM: Artificial
<220> FEATURE:
<223> OTHER INFORMATION: synthetic polypeptide

<400> SEQUENCE: 51

Gly Asn Ser Leu Arg Gly Ser Cys Pro Phe Leu Gln Pro Ser Thr Glu
1               5                   10                  15

Ser Ser Val

<210> SEQ ID NO 52
<211> LENGTH: 9
<212> TYPE: PRT
<213> ORGANISM: Artificial
<220> FEATURE:
<223> OTHER INFORMATION: synthetic polypeptide

<400> SEQUENCE: 52

Arg Lys Leu Gly Ser Phe Gly Gln Pro
1               5

<210> SEQ ID NO 53
<211> LENGTH: 8
<212> TYPE: PRT
<213> ORGANISM: Artificial
<220> FEATURE:
<223> OTHER INFORMATION: synthetic polypeptide

<400> SEQUENCE: 53

Val Ser Thr Arg Leu Thr Pro Cys
1               5

<210> SEQ ID NO 54
<211> LENGTH: 128

<212> TYPE: PRT
<213> ORGANISM: Glycine max

<400> SEQUENCE: 54

Gly Ile Tyr Ser Pro His Trp Asn Leu Asn Ala Asn Ser Val Ile Tyr
1               5                   10                  15

Val Thr Arg Gly Gln Gly Lys Val Arg Val Val Asn Cys Gln Gly Asn
            20                  25                  30

Ala Val Phe Asp Gly Glu Leu Arg Arg Gly Gln Leu Leu Val Val Pro
        35                  40                  45

Gln Asn Phe Val Val Ala Glu Gln Ala Gly Glu Gln Gly Phe Glu Tyr
    50                  55                  60

Ile Val Phe Lys Thr His His Asn Ala Val Thr Ser Tyr Leu Lys Asp
65                  70                  75                  80

Val Phe Arg Ala Ile Pro Ser Glu Val Leu Ala His Ser Tyr Asn Leu
                85                  90                  95

Arg Gln Ser Gln Val Ser Glu Leu Lys Tyr Glu Gly Asn Trp Gly Pro
            100                 105                 110

Leu Val Asn Pro Glu Ser Gln Gln Gly Ser Pro Arg Val Lys Val Ala
        115                 120                 125

<210> SEQ ID NO 55
<211> LENGTH: 562
<212> TYPE: PRT
<213> ORGANISM: Glycine max

<400> SEQUENCE: 55

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Ser Lys Leu Asn Glu Cys
            20                  25                  30

Gln Leu Asn Asn Leu Asn Ala Leu Glu Pro Asp His Arg Val Glu Ser
        35                  40                  45

Glu Gly Gly Leu Ile Gln Thr Trp Asn Ser Gln His Pro Glu Leu Lys
    50                  55                  60

Cys Ala Gly Val Thr Val Ser Lys Leu Thr Leu Asn Arg Asn Gly Leu
65                  70                  75                  80

His Ser Pro Ser Tyr Ser Pro Tyr Pro Arg Met Ile Ile Ile Ala Gln
                85                  90                  95

Gly Lys Gly Ala Leu Gly Val Ala Ile Pro Gly Cys Pro Glu Thr Phe
            100                 105                 110

Glu Glu Pro Gln Glu Gln Ser Asn Arg Arg Gly Ser Arg Ser Gln Lys
        115                 120                 125

Gln Gln Leu Gln Asp Ser His Gln Lys Ile Arg His Phe Asn Glu Gly
    130                 135                 140

Asp Val Leu Val Ile Pro Pro Ser Val Pro Tyr Trp Thr Tyr Asn Thr
145                 150                 155                 160

Gly Asp Glu Pro Val Val Ala Ile Ser Leu Leu Asp Thr Ser Asn Phe
                165                 170                 175

Asn Asn Gln Leu Asp Gln Thr Pro Arg Val Phe Tyr Leu Ala Gly Asn
            180                 185                 190

Pro Asp Ile Glu Tyr Pro Glu Thr Met Gln Gln Gln Gln Gln Gln Lys
        195                 200                 205

Ser His Gly Gly Arg Lys Gln Gly Gln His Gln Glu Glu Glu Glu
    210                 215                 220

```
Glu Gly Gly Ser Val Leu Ser Gly Phe Ser Lys His Phe Leu Ala Gln
225                 230                 235                 240

Ser Phe Asn Thr Asn Glu Asp Ile Ala Glu Lys Leu Glu Ser Pro Asp
            245                 250                 255

Asp Glu Arg Lys Gln Ile Val Thr Val Glu Gly Gly Leu Ser Val Ile
        260                 265                 270

Ser Pro Lys Trp Gln Glu Gln Asp Glu Asp Glu Asp Glu Asp Glu
    275                 280                 285

Asp Glu Asp Glu Gln Ile Pro Ser His Pro Arg Arg Pro Ser
290                 295                 300

His Gly Lys Arg Glu Gln Asp Glu Asp Glu Asp Glu Asp Glu Asp Lys
305                 310                 315                 320

Pro Arg Pro Ser Arg Pro Ser Gln Gly Lys Arg Asn Lys Thr Gly Gln
            325                 330                 335

Asp Glu Asp Glu Asp Glu Asp Glu Asp Gln Pro Arg Lys Ser Arg Glu
        340                 345                 350

Trp Arg Ser Lys Lys Thr Gln Pro Arg Pro Arg Gln Glu Glu Pro
    355                 360                 365

Arg Glu Arg Gly Cys Glu Thr Arg Asn Gly Val Glu Glu Asn Ile Cys
370                 375                 380

Thr Leu Lys Leu His Glu Asn Ile Ala Arg Pro Ser Arg Ala Asp Phe
385                 390                 395                 400

Tyr Asn Pro Lys Ala Gly Arg Ile Ser Thr Leu Asn Ser Leu Thr Leu
            405                 410                 415

Pro Ala Leu Arg Gln Phe Gln Leu Ser Ala Gln Tyr Val Val Leu Tyr
        420                 425                 430

Lys Asn Gly Ile Tyr Ser Pro His Trp Asn Leu Asn Ala Asn Ser Val
    435                 440                 445

Ile Tyr Val Thr Arg Gly Gln Gly Lys Val Arg Val Val Asn Cys Gln
450                 455                 460

Gly Asn Ala Val Phe Asp Gly Glu Leu Arg Arg Gly Gln Leu Leu Val
465                 470                 475                 480

Val Pro Gln Asn Phe Val Val Ala Glu Gln Ala Gly Glu Gln Gly Phe
            485                 490                 495

Glu Tyr Ile Val Phe Lys Thr His His Asn Ala Val Thr Ser Tyr Leu
        500                 505                 510

Lys Asp Val Phe Arg Ala Ile Pro Ser Glu Val Leu Ala His Ser Tyr
    515                 520                 525

Asn Leu Arg Gln Ser Gln Val Ser Glu Leu Lys Tyr Glu Gly Asn Trp
530                 535                 540

Gly Pro Leu Val Asn Pro Glu Ser Gln Gln Gly Ser Pro Arg Val Lys
545                 550                 555                 560

Val Ala

<210> SEQ ID NO 56
<211> LENGTH: 385
<212> TYPE: PRT
<213> ORGANISM: Artificial
<220> FEATURE:
<223> OTHER INFORMATION: synthetic polypeptide

<400> SEQUENCE: 56

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Ser Lys Leu Asn Glu Cys
```

```
            20                  25                  30
Gln Leu Asn Asn Leu Asn Ala Leu Glu Pro Asp His Arg Val Glu Ser
         35                  40                  45
Glu Gly Gly Leu Ile Gln Thr Trp Asn Ser Gln His Pro Glu Leu Lys
 50                  55                  60
Cys Ala Gly Val Thr Val Ser Lys Leu Thr Leu Asn Arg Asn Gly Leu
 65                  70                  75                  80
His Ser Pro Ser Tyr Ser Pro Tyr Pro Arg Met Ile Ile Ala Gln
                 85                  90                  95
Gly Lys Gly Ala Leu Gly Val Ala Ile Pro Gly Cys Pro Glu Thr Phe
                100                 105                 110
Glu Glu Pro Gln Glu Gln Ser Asn Arg Arg Gly Ser Arg Ser Gln Lys
                115                 120                 125
Gln Gln Leu Gln Asp Ser His Gln Lys Ile Arg His Phe Asn Glu Gly
            130                 135                 140
Asp Val Leu Val Ile Pro Pro Ser Val Pro Tyr Trp Thr Tyr Asn Thr
145                 150                 155                 160
Gly Asp Glu Pro Val Val Ala Ile Ser Leu Leu Asp Thr Ser Asn Phe
                165                 170                 175
Asn Asn Gln Leu Asp Gln Thr Pro Arg Val Phe Tyr Leu Ala Gly Asn
            180                 185                 190
Pro Asp Ile Glu Tyr Pro Glu Thr Met Gln Gln Gln Gln Gln Gln Lys
            195                 200                 205
Ser His Gly Gly Arg Lys Gln Gly Gln His Gln Gln Glu Glu Glu Glu
        210                 215                 220
Glu Gly Gly Ser Val Leu Ser Gly Phe Ser Lys His Phe Leu Ala Gln
225                 230                 235                 240
Ser Phe Asn Thr Asn Glu Asp Ile Ala Glu Lys Leu Glu Ser Pro Asp
                245                 250                 255
Asp Glu Arg Lys Gln Ile Gln Trp Lys Glu Val Ser Ala Leu Ser Ala
            260                 265                 270
Pro Ser Gly Lys Asn Asn Lys Met Lys Met Lys Met Lys Thr Lys Met
            275                 280                 285
Met Lys Met Asn Lys Phe Pro Leu Thr Leu Leu Ala Asp Gln Ala Met
        290                 295                 300
Glu Ser Val Asn Lys Thr Arg Thr Arg Thr Lys Met Lys Ile Asn Leu
305                 310                 315                 320
Val Leu Val Asp Gln Ala Lys Glu Ser Val Asn Lys Thr Arg Thr Arg
                325                 330                 335
Thr Arg Thr Lys Met Lys Met Lys Ile Asn Leu Ala Arg Ala Ala Asn
            340                 345                 350
Gly Asp Arg Lys Arg His Asn Pro Glu Asp Leu Asp Lys Lys Asn His
            355                 360                 365
Val Lys Glu Asp Ala Arg Gln Glu Thr Gly Leu Arg Lys Ile Ser Ala
        370                 375                 380
Pro
385

<210> SEQ ID NO 57
<211> LENGTH: 563
<212> TYPE: PRT
<213> ORGANISM: Artificial
<220> FEATURE:
<223> OTHER INFORMATION: synthetic polypeptide
```

<400> SEQUENCE: 57

Met Gly Lys Pro Phe Thr Leu Ser Leu Ser Ser Leu Cys Leu Leu Leu
1               5                   10                  15

Leu Ser Ser Ala Cys Phe Ala Ile Ser Ser Lys Leu Asn Glu Cys
            20                  25                  30

Gln Leu Asn Asn Leu Asn Ala Leu Glu Pro Asp His Arg Val Glu Ser
        35                  40                  45

Glu Gly Gly Leu Ile Gln Thr Trp Asn Ser Gln His Pro Glu Leu Lys
    50                  55                  60

Cys Ala Gly Val Thr Val Ser Lys Leu Thr Leu Asn Arg Asn Gly Leu
65                  70                  75                  80

His Ser Pro Ser Tyr Ser Pro Tyr Pro Arg Met Ile Ile Ile Ala Gln
                85                  90                  95

Gly Lys Gly Ala Leu Gly Val Ala Ile Pro Gly Cys Pro Glu Thr Phe
            100                 105                 110

Glu Glu Pro Gln Glu Gln Ser Asn Arg Arg Gly Ser Arg Ser Gln Lys
        115                 120                 125

Gln Gln Leu Gln Asp Ser His Gln Lys Ile Arg His Phe Asn Glu Gly
    130                 135                 140

Asp Val Leu Val Ile Pro Ser Val Pro Tyr Trp Thr Tyr Asn Thr
145                 150                 155                 160

Gly Asp Glu Pro Val Val Ala Ile Ser Leu Leu Asp Thr Ser Asn Phe
                165                 170                 175

Asn Asn Gln Leu Asp Gln Thr Pro Arg Val Phe Tyr Leu Ala Gly Asn
            180                 185                 190

Pro Asp Ile Glu Tyr Pro Glu Thr Met Gln Gln Gln Gln Gln Gln Lys
        195                 200                 205

Ser His Gly Gly Arg Lys Gln Gly Gln His Gln Glu Glu Glu Glu
    210                 215                 220

Glu Gly Gly Ser Val Leu Ser Gly Phe Ser Lys His Phe Leu Ala Gln
225                 230                 235                 240

Ser Phe Asn Thr Asn Glu Asp Ile Ala Glu Lys Leu Glu Ser Pro Asp
                245                 250                 255

Asp Glu Arg Lys Gln Ile Gln Trp Lys Glu Val Ser Ala Leu Ser Ala
            260                 265                 270

Pro Ser Gly Lys Asn Asn Lys Met Lys Met Lys Met Lys Thr Lys Met
        275                 280                 285

Met Lys Met Asn Lys Phe Pro Leu Thr Leu Leu Ala Asp Gln Ala Met
    290                 295                 300

Glu Ser Val Asn Lys Thr Arg Thr Arg Thr Lys Met Lys Ile Asn Leu
305                 310                 315                 320

Val Leu Val Asp Gln Ala Lys Glu Ser Val Asn Lys Thr Arg Thr Arg
                325                 330                 335

Thr Arg Thr Lys Met Lys Met Lys Ile Asn Leu Ala Arg Lys Ser Arg
            340                 345                 350

Glu Trp Arg Ser Lys Lys Thr Gln Pro Arg Arg Pro Arg Gln Glu Glu
        355                 360                 365

Pro Arg Glu Arg Gly Cys Glu Thr Arg Asn Gly Val Glu Glu Asn Ile
    370                 375                 380

Cys Thr Leu Lys Leu His Glu Asn Ile Ala Arg Pro Ser Arg Ala Asp
385                 390                 395                 400

Phe Tyr Asn Pro Lys Ala Gly Arg Ile Ser Thr Leu Asn Ser Leu Thr
                405                 410                 415

Leu Pro Ala Leu Arg Gln Phe Gln Leu Ser Ala Gln Tyr Val Val Leu
                420                 425                 430

Tyr Lys Asn Gly Ile Tyr Ser Pro His Trp Asn Leu Asn Ala Asn Ser
            435                 440                 445

Val Ile Tyr Val Thr Arg Gly Gln Gly Lys Val Arg Val Val Asn Cys
450                 455                 460

Gln Gly Asn Ala Val Phe Asp Gly Glu Leu Arg Gly Gln Leu Leu
465                 470                 475                 480

Val Val Pro Gln Asn Phe Val Ala Glu Gln Ala Gly Glu Gln Gly
                485                 490                 495

Phe Glu Tyr Ile Val Phe Lys Thr His His Asn Ala Val Thr Ser Tyr
            500                 505                 510

Leu Lys Asp Val Phe Arg Ala Ile Pro Ser Glu Val Leu Ala His Ser
            515                 520                 525

Tyr Asn Leu Arg Gln Ser Gln Val Ser Glu Leu Lys Tyr Glu Gly Asn
            530                 535                 540

Trp Gly Pro Leu Val Asn Pro Glu Ser Gln Gln Gly Ser Pro Arg Val
545                 550                 555                 560

Lys Val Ala

<210> SEQ ID NO 58
<211> LENGTH: 894
<212> TYPE: DNA
<213> ORGANISM: Triticum aestivum

<400> SEQUENCE: 58
atgaagacct ttctcatcct tgccctccgt gctattgtag caaccaccgc cacaattgca      60
gttagagttc cagtgccaca attgcagcca caaaatccat ctcagcagca accacaaaag     120
caagttccat tggtacaaca acaacaattt ccagggcagc aacaaccatt tccaccacaa     180
cagccatatc cgcagctgca accatttcca tcacaacaac catatatgca gctgcaacca     240
tttccgcagc cgcaactacc atatccgcag ccgcaactac catatccgca gccgcaacca     300
tttcgaccac aacaatcata tccacaaccg caaccacagt attcgcaacc acaacaacca     360
atctcgcagc agcagcagca gcagcagcag caacaacaac aacaacaaca gatccttcaa     420
caaattttgc aacaacaact gattccatgc agggatgttg tattgcaaca acacagcata     480
gcgcatggaa gctcacaagt tttgcaacaa gtacttacc agctggtgca acaattgtgt      540
tgtcagcagc tatggcagat ccccgagcag tcgcggtgcc aagccatcca caatgttgtt     600
catgctatta ttctgcatca acaacaacaa caacaacaac aacaacaaca acaacaacaa     660
caaccgttga gccaggtctg cttccaacag tctcaacaac aatatccatc aggccagggc     720
tccttccagc catctcagca aaacccacag gcccagggct ctgtccagcc tcaacaactg     780
ccccagtttg aggaaataag gaacctagcg ctagagacgc tacctgcaat gtgcaatgtc     840
tatatccctc catattgcac cattgctcca gttggcatct cggtactaa ctga           894

<210> SEQ ID NO 59
<211> LENGTH: 11
<212> TYPE: PRT
<213> ORGANISM: Artificial
<220> FEATURE:
<223> OTHER INFORMATION: synthetic polypeptide

<400> SEQUENCE: 59

Arg Pro Phe Ser Ser Leu Pro Ser Val Leu Leu

<210> SEQ ID NO 60
<211> LENGTH: 133
<212> TYPE: PRT
<213> ORGANISM: Artificial
<220> FEATURE:
<223> OTHER INFORMATION: synthetic polypeptide

<400> SEQUENCE: 60

Gln Pro Pro Pro Gln Leu Gln Leu Glu Phe Gln Cys His Asn Cys Ser
1               5                   10                  15

His Lys Ile His Leu Ser Ser Asn His Lys Ser Lys Phe His Trp Tyr
            20                  25                  30

Asn Asn Asn Asn Phe Gln Gly Ser Asn Asn His Phe His His Asn Ser
        35                  40                  45

His Ile Arg Ser Cys Asn His Phe His His Asn Asn His Ile Cys Ser
    50                  55                  60

Cys Asn His Phe Arg Ser Arg Asn Tyr His Ile Arg Ser Arg Asn Tyr
65                  70                  75                  80

His Ile Arg Ser Arg Asn His Phe Asp His Asn Asn His Ile His Asn
                85                  90                  95

Arg Asn His Ser Ile Arg Asn His Asn Asn Gln Ser Arg Ser Ser Ser
            100                 105                 110

Ser Ser Ser Ser Ser Asn Asn Asn Asn Asn Arg Ser Phe Asn Lys
        115                 120                 125

Phe Cys Asn Asn Asn
    130

<210> SEQ ID NO 61
<211> LENGTH: 12
<212> TYPE: PRT
<213> ORGANISM: Artificial
<220> FEATURE:
<223> OTHER INFORMATION: synthetic polypeptide

<400> SEQUENCE: 61

Phe His Ala Gly Met Leu Tyr Cys Asn Asn Thr Ala
1               5                   10

<210> SEQ ID NO 62
<211> LENGTH: 62
<212> TYPE: PRT
<213> ORGANISM: Artificial
<220> FEATURE:
<223> OTHER INFORMATION: synthetic polypeptide

<400> SEQUENCE: 62

Arg Met Glu Ala His Lys Phe Cys Asn Lys Val Leu Thr Ser Trp Cys
1               5                   10                  15

Asn Asn Cys Val Val Ser Ser Tyr Gly Arg Ser Pro Ser Ser Arg Gly
            20                  25                  30

Ala Lys Pro Ser Thr Met Leu Phe Met Leu Leu Phe Cys Ile Asn Asn
        35                  40                  45

Asn Asn Asn Asn Asn Asn Asn Asn Asn Asn Asn Asn Arg
    50                  55                  60

<210> SEQ ID NO 63
<211> LENGTH: 42
<212> TYPE: PRT
<213> ORGANISM: Artificial

-continued

```
<220> FEATURE:
<223> OTHER INFORMATION: synthetic polypeptide

<400> SEQUENCE: 63

Ala Arg Ser Ala Ser Asn Ser Leu Asn Asn Asn Ile His Gln Ala Arg
1               5                   10                  15

Ala Pro Ser Ser His Leu Ser Lys Thr His Arg Pro Arg Ala Leu Ser
                20                  25                  30

Ser Leu Asn Asn Cys Pro Ser Leu Arg Lys
            35                  40

<210> SEQ ID NO 64
<211> LENGTH: 26
<212> TYPE: PRT
<213> ORGANISM: Artificial
<220> FEATURE:
<223> OTHER INFORMATION: synthetic polypeptide

<400> SEQUENCE: 64

Arg Arg Tyr Leu Gln Cys Ala Met Ser Ile Ser Leu His Ile Ala Pro
1               5                   10                  15

Leu Leu Gln Leu Ala Ser Ser Val Leu Thr
                20                  25

<210> SEQ ID NO 65
<211> LENGTH: 20
<212> TYPE: PRT
<213> ORGANISM: Artificial
<220> FEATURE:
<223> OTHER INFORMATION: synthetic polypeptide

<400> SEQUENCE: 65

Glu Asp Leu Ser His Pro Cys Pro Pro Cys Tyr Cys Ser Asn His Arg
1               5                   10                  15

His Asn Cys Ser
            20

<210> SEQ ID NO 66
<211> LENGTH: 241
<212> TYPE: PRT
<213> ORGANISM: Artificial
<220> FEATURE:
<223> OTHER INFORMATION: synthetic polypeptide

<400> SEQUENCE: 66

Ser Ser Ser Ala Thr Ile Ala Ala Thr Lys Ser Ile Ser Ala Ala Thr
1               5                   10                  15

Thr Lys Ala Ser Ser Ile Gly Thr Thr Thr Thr Ile Ser Arg Ala Ala
                20                  25                  30

Thr Thr Ile Ser Thr Thr Thr Ala Ile Ser Ala Ala Thr Ile Ser
            35                  40                  45

Ile Thr Thr Thr Ile Tyr Ala Ala Ala Thr Ile Ser Ala Ala Ala Thr
        50                  55                  60

Thr Ile Ser Ala Ala Ala Thr Thr Ile Ser Ala Ala Ala Thr Ile Ser
65                  70                  75                  80

Thr Thr Thr Ile Ile Ser Thr Thr Ala Thr Thr Val Phe Ala Thr Thr
                85                  90                  95

Thr Thr Asn Leu Ala Ala Ala Ala Ala Ala Ala Thr Thr Thr
            100                 105                 110

Thr Thr Thr Asp Pro Ser Thr Asn Phe Ala Thr Thr Asp Ser Met
        115                 120                 125
```

-continued

Gln Gly Cys Cys Ile Ala Thr Thr Gln His Ser Ala Trp Lys Leu Thr
        130                 135                 140

Ser Phe Ala Thr Lys Tyr Leu Pro Ala Gly Ala Thr Ile Val Leu Ser
145                 150                 155                 160

Ala Ala Met Ala Asp Pro Arg Ala Val Ala Val Pro Ser His Pro Gln
                165                 170                 175

Cys Cys Ser Cys Tyr Tyr Ser Ala Ser Thr Thr Thr Thr Thr Thr Thr
            180                 185                 190

Thr Thr Thr Thr Thr Thr Thr Thr Val Glu Pro Gly Leu Leu Pro Thr
            195                 200                 205

Val Ser Thr Thr Ile Ser Ile Arg Pro Gly Leu Leu Pro Ala Ile Ser
    210                 215                 220

Ala Lys Pro Thr Gly Pro Gly Leu Cys Pro Ala Ser Thr Thr Ala Pro
225                 230                 235                 240

Val

<210> SEQ ID NO 67
<211> LENGTH: 32
<212> TYPE: PRT
<213> ORGANISM: Artificial
<220> FEATURE:
<223> OTHER INFORMATION: synthetic polypeptide

<400> SEQUENCE: 67

Gly Asn Lys Glu Pro Ser Ala Arg Asp Ala Thr Cys Asn Val Gln Cys
1               5                   10                  15

Leu Tyr Pro Ser Ile Leu His His Cys Ser Ser Trp His Leu Arg Tyr
            20                  25                  30

<210> SEQ ID NO 68
<211> LENGTH: 297
<212> TYPE: PRT
<213> ORGANISM: Triticum aestivum

<400> SEQUENCE: 68

Met Lys Thr Phe Leu Ile Leu Ala Leu Arg Ala Ile Val Ala Thr Thr
1               5                   10                  15

Ala Thr Ile Ala Val Arg Val Pro Val Pro Gln Leu Gln Pro Gln Asn
            20                  25                  30

Pro Ser Gln Gln Gln Pro Gln Lys Gln Val Pro Leu Val Gln Gln Gln
        35                  40                  45

Gln Phe Pro Gly Gln Gln Gln Pro Phe Pro Pro Gln Gln Pro Tyr Pro
    50                  55                  60

Gln Leu Gln Pro Phe Pro Ser Gln Gln Pro Tyr Met Gln Leu Gln Pro
65                  70                  75                  80

Phe Pro Gln Pro Gln Leu Pro Tyr Pro Gln Pro Gln Leu Pro Tyr Pro
                85                  90                  95

Gln Pro Gln Pro Phe Arg Pro Gln Gln Ser Tyr Pro Gln Pro Gln Pro
            100                 105                 110

Gln Tyr Ser Gln Pro Gln Gln Pro Ile Ser Gln Gln Gln Gln Gln Gln
        115                 120                 125

Gln Gln Gln Gln Gln Gln Gln Gln Ile Leu Gln Gln Ile Leu Gln
    130                 135                 140

Gln Gln Leu Ile Pro Cys Arg Asp Val Val Leu Gln Gln His Ser Ile
145                 150                 155                 160

Ala His Gly Ser Ser Gln Val Leu Gln Gln Ser Thr Tyr Gln Leu Val

```
                         165                 170                 175
Gln Gln Leu Cys Cys Gln Gln Leu Trp Gln Ile Pro Glu Gln Ser Arg
                180                 185                 190

Cys Gln Ala Ile His Asn Val Val His Ala Ile Ile Leu His Gln Gln
            195                 200                 205

Gln Gln Gln Gln Gln Gln Gln Gln Gln Gln Gln Pro Leu Ser
        210                 215                 220

Gln Val Cys Phe Gln Gln Ser Gln Gln Gln Tyr Pro Ser Gly Gln Gly
225                 230                 235                 240

Ser Phe Gln Pro Ser Gln Gln Asn Pro Gln Ala Gln Gly Ser Val Gln
                245                 250                 255

Pro Gln Gln Leu Pro Gln Phe Glu Glu Ile Arg Asn Leu Ala Leu Glu
            260                 265                 270

Thr Leu Pro Ala Met Cys Asn Val Tyr Ile Pro Pro Tyr Cys Thr Ile
        275                 280                 285

Ala Pro Val Gly Ile Phe Gly Thr Asn
    290                 295

<210> SEQ ID NO 69
<211> LENGTH: 266
<212> TYPE: PRT
<213> ORGANISM: Artificial
<220> FEATURE:
<223> OTHER INFORMATION: synthetic polypeptide

<400> SEQUENCE: 69

Met Lys Thr Phe Leu Ile Leu Ala Leu Arg Ala Ile Val Ala Thr Thr
1               5                   10                  15

Ala Thr Ile Ala Val Arg Val Pro Val Ser Ser Ser Ala Thr Ile Ala
                20                  25                  30

Ala Thr Lys Ser Ile Ser Ala Ala Thr Thr Lys Ala Ser Ser Ile Gly
            35                  40                  45

Thr Thr Thr Thr Ile Ser Arg Ala Ala Thr Thr Ile Ser Thr Thr Thr
        50                  55                  60

Ala Ile Ser Ala Ala Ala Thr Ile Ser Ile Thr Thr Ile Tyr Ala
65                  70                  75                  80

Ala Ala Thr Ile Ser Ala Ala Ala Thr Ile Ser Ala Ala Ala Thr
                85                  90                  95

Thr Ile Ser Ala Ala Ala Thr Ile Ser Thr Thr Ile Ile Ser Thr
            100                 105                 110

Thr Ala Thr Thr Val Phe Ala Thr Thr Thr Asn Leu Ala Ala Ala
        115                 120                 125

Ala Ala Ala Ala Ala Thr Thr Thr Thr Thr Asp Pro Ser Thr
    130                 135                 140

Asn Phe Ala Thr Thr Thr Asp Ser Met Gln Gly Cys Cys Ile Ala Thr
145                 150                 155                 160

Thr Gln His Ser Ala Trp Lys Leu Thr Ser Phe Ala Thr Lys Tyr Leu
                165                 170                 175

Pro Ala Gly Ala Thr Ile Val Leu Ser Ala Ala Met Ala Asp Pro Arg
            180                 185                 190

Ala Val Ala Val Pro Ser His Pro Gln Cys Cys Ser Cys Tyr Tyr Ser
        195                 200                 205

Ala Ser Thr Thr Thr Thr Thr Thr Thr Thr Thr Thr Thr Thr
    210                 215                 220

Thr Val Glu Pro Gly Leu Leu Pro Thr Val Ser Thr Thr Ile Ser Ile
```

```
                225                 230                 235                 240
Arg Pro Gly Leu Leu Pro Ala Ile Ser Ala Lys Pro Thr Gly Pro Gly
                    245                 250                 255
Leu Cys Pro Ala Ser Thr Thr Ala Pro Val
                260                 265

<210> SEQ ID NO 70
<211> LENGTH: 2547
<212> TYPE: DNA
<213> ORGANISM: Triticum aestivum

<400> SEQUENCE: 70
atggctaagc ggttagtcct ctttgtggcg gtagtcgtcg ccctcgtggc tctcaccgtc      60
gctgaaggtg aggcctctga gcaactacag tgtgagcgcg agctccagga gctccaggag     120
cgcgagctca aggcatgcca gcaggtcatg gaccaacagc tccgagacat tagccccgag     180
tgccaccccg tcgtcgtcag cccggtcgcg ggacaatacg agcagcaaat cgtggtgccg     240
cccaagggcg gatctttcta ccccggcgag accacgccac cgcagcaact ccaacaacgt     300
atattttggg gaatacctgc actactaaaa aggtattacc caagtgtaac ttgtccgcag     360
caggtttcat actatccagg ccaagcttct ccgcaacggc caggacaagg tcagcagcca     420
ggacaaggac aacaagggta ctacccaact tctccgcaac agccaggaca atggcaacaa     480
ccggaacaag gcaaccaag gtactaccca acttctccgc agcagtcagg acaattgcaa     540
caaccagcac aagggcagca accaggacaa gggcaacaag gtcagcagcc aggacaaggg     600
caaccagggt actacccaac ttcttcgcag ctgcagccag acaattgca caaccagca     660
caagggcaac aaggcagca accaggacaa gcgcaacaag gtcaacagcc aggacaaggg     720
caacaaccag acaaggaca caaggtcaa cagccaggac aagggcaaca accaggacaa     780
gggcaacaag gtcagcagct cggacaagga caacaagggt actacccaac ttctctgcaa     840
cagtcgggac aagggcaacc agggtactac ccaacttctc tgcagcagct aggacaaggg     900
caatcagggt actacccaac ttctccgcag caaccaggac aagggcagca gccaggacaa     960
ttgcaacaac cagcacaagg gcagcaacca ggacaaggg aacaaggtca gcagccagga    1020
caagggcaac aaggccagca gccaggacaa gggcagcaac cggacaagg gcaaccaggg    1080
tactacccaa cttctccgca gcagtcagga agggcaac cagggtacta cccaacttct    1140
tcgcagcagc aacacaatc gcagcaacca ggacaagggc aacaaggtca gcaggtagga    1200
caagggcaac aagctcagca gccaggacaa gggcagcaac cggacaagg gcagccaggg    1260
tactacccaa cttctccgca gcagtcagga agggcaac cagggtacta cctaacttct    1320
ccgcagcagt caggacaagg gcagcagcca ggacaattgc aacaatcagc acaagggcaa    1380
aaaggacagc aaccaggaca aggtcaacag ccagggcaag gcaacaagg tcagcagcca    1440
ggacaagggc aacaaggtca gcaccgggg caagggcagc cagggtacta cccaacttct    1500
ccgcagcaat caggacaagg gcaacagcca ggacaatggc aacaaccagg acaagggcaa    1560
ccaggatact acccaacttc tccgttgcag ccaggacaag gcaaccagg gtacgaccca    1620
acttctccgc aacagccagg acaagggcag caaccggaca aattgcaaca accagcacaa    1680
gggcaacaag gcagcaact agcacaaggg caacaagggc agcaaccagc acaagtgcaa    1740
caagggcagc ggccagcaca agggcaacaa ggtcagcagc caggacaagg caacaaggt    1800
cagcagctag acaagggca acaaggtcag cagccaggac aagggcaaca agggcagcaa    1860
ccagcacaag gcaacaagg tcagcagcca ggacaagggc aacaaggtca gcagccagga    1920
```

```
caagggcaac aaggtcagca gccaggacaa gggcagcaac cgggacaagg gcagccatgg   1980
tactacccaa cttctccgca ggagtcagga caagggcaac agccaggaca atggcaacaa   2040
ccaggacaag ggcaaccagg gtactaccta acttctccgt tgcagctagg acaagggcaa   2100
caagggtact acccaacttc tctgcaacaa ccaggacaag ggcagcaacc aggacaatgg   2160
caacaatcgg acaagggca acattggtac tacccaactt ctccgcagct gtcaggacaa   2220
gggcaacggc caggacaatg gctgcaacca ggacaagggc aacaagggta ctacccaact   2280
tctccgcaac agccaggaca agggcaacaa ctaggacaat ggctgcaacc aggacaaggg   2340
caacaagggt actacccaac ttctctgcaa cagacaggac aagggcagca atcaggacaa   2400
gggcaacaag gctactacag ctcataccat gttagcgtgg agcaccaggc ggccagccta   2460
aaggtggcaa aggcgcagca gctcgcggca cagctgccgg caatgtgccg gctggagggc   2520
ggcgacgcat tgtcggccag ccagtga                                      2547

<210> SEQ ID NO 71
<211> LENGTH: 4
<212> TYPE: PRT
<213> ORGANISM: Artificial
<220> FEATURE:
<223> OTHER INFORMATION: synthetic polypeptide

<400> SEQUENCE: 71

Trp Leu Ser Gly
1

<210> SEQ ID NO 72
<211> LENGTH: 5
<212> TYPE: PRT
<213> ORGANISM: Artificial
<220> FEATURE:
<223> OTHER INFORMATION: synthetic polypeptide

<400> SEQUENCE: 72

Ser Ser Leu Trp Arg
1               5

<210> SEQ ID NO 73
<211> LENGTH: 97
<212> TYPE: PRT
<213> ORGANISM: Artificial
<220> FEATURE:
<223> OTHER INFORMATION: synthetic polypeptide

<400> SEQUENCE: 73

Ser Ser Pro Ser Trp Leu Ser Pro Ser Leu Lys Val Arg Pro Leu Ser
1               5                   10                  15

Asn Tyr Ser Val Ser Ala Ser Ser Arg Ser Ser Arg Ser Ala Ser Ser
            20                  25                  30

Arg His Ala Ser Arg Ser Trp Thr Asn Ser Ser Glu Thr Leu Ala Pro
        35                  40                  45

Ser Ala Thr Pro Ser Ser Ser Ala Arg Ser Arg Asp Asn Thr Ser Ser
    50                  55                  60

Lys Ser Trp Cys Arg Pro Arg Ala Asp Leu Ser Thr Pro Ala Arg Pro
65                  70                  75                  80

Arg His Arg Ser Asn Ser Asn Asn Val Tyr Phe Gly Glu Tyr Leu His
                85                  90                  95

Tyr
```

<210> SEQ ID NO 74
<211> LENGTH: 6
<212> TYPE: PRT
<213> ORGANISM: Artificial
<220> FEATURE:
<223> OTHER INFORMATION: synthetic polypeptide

<400> SEQUENCE: 74

Lys Gly Ile Thr Gln Val
1               5

<210> SEQ ID NO 75
<211> LENGTH: 180
<212> TYPE: PRT
<213> ORGANISM: Artificial
<220> FEATURE:
<223> OTHER INFORMATION: synthetic polypeptide

<400> SEQUENCE: 75

Leu Val Arg Ser Arg Phe His Thr Ile Gln Ala Lys Leu Leu Arg Asn
1               5                   10                  15

Gly Gln Asp Lys Val Ser Ser Gln Asp Lys Asp Asn Lys Gly Thr Thr
            20                  25                  30

Gln Leu Leu Arg Asn Ser Gln Asp Asn Gly Asn Asn Arg Asn Lys Gly
        35                  40                  45

Asn Gln Gly Thr Thr Gln Leu Leu Arg Ser Ser Gln Asp Asn Cys Asn
    50                  55                  60

Asn Gln His Lys Gly Ser Asn Gln Asp Lys Gly Asn Lys Val Ser Ser
65                  70                  75                  80

Gln Asp Lys Gly Asn Gln Gly Thr Thr Gln Leu Leu Arg Ser Cys Ser
                85                  90                  95

Gln Asp Asn Cys Asn Asn Gln His Lys Gly Asn Lys Gly Ser Asn Gln
            100                 105                 110

Asp Lys Arg Asn Lys Val Asn Ser Gln Asp Lys Gly Asn Asn Gln Asp
        115                 120                 125

Lys Asp Asn Lys Val Asn Ser Gln Asp Lys Gly Asn Asn Gln Asp Lys
    130                 135                 140

Gly Asn Lys Val Ser Ser Ser Asp Lys Asp Asn Lys Gly Thr Thr Gln
145                 150                 155                 160

Leu Leu Cys Asn Ser Arg Asp Lys Gly Asn Gln Gly Thr Thr Gln Leu
                165                 170                 175

Leu Cys Ser Ser
            180

<210> SEQ ID NO 76
<211> LENGTH: 101
<212> TYPE: PRT
<213> ORGANISM: Artificial
<220> FEATURE:
<223> OTHER INFORMATION: synthetic polypeptide

<400> SEQUENCE: 76

Asp Lys Gly Asn Gln Gly Thr Thr Gln Leu Leu Arg Ser Asn Gln Asp
1               5                   10                  15

Lys Gly Ser Ser Gln Asp Asn Cys Asn Asn Gln His Lys Gly Ser Asn
            20                  25                  30

Gln Asp Lys Gly Asn Lys Val Ser Ser Gln Asp Lys Gly Asn Lys Ala
        35                  40                  45

Ser Ser Gln Asp Lys Gly Ser Asn Arg Asp Lys Gly Asn Gln Gly Thr

```
                    50                  55                  60

Thr Gln Leu Leu Arg Ser Ser Gln Asp Lys Gly Asn Gln Gly Thr Thr
 65                  70                  75                  80

Gln Leu Leu Arg Ser Ser Gln His Asn Arg Ser Asn Gln Asp Lys Gly
                     85                  90                  95

Asn Lys Val Ser Arg
            100

<210> SEQ ID NO 77
<211> LENGTH: 38
<212> TYPE: PRT
<213> ORGANISM: Artificial
<220> FEATURE:
<223> OTHER INFORMATION: synthetic polypeptide

<400> SEQUENCE: 77

Asp Lys Gly Asn Lys Leu Ser Ser Gln Asp Lys Gly Ser Asn Arg Asp
  1               5                  10                  15

Lys Gly Ser Gln Gly Thr Thr Gln Leu Leu Arg Ser Ser Gln Asp Lys
                 20                  25                  30

Gly Asn Gln Gly Thr Thr
            35

<210> SEQ ID NO 78
<211> LENGTH: 128
<212> TYPE: PRT
<213> ORGANISM: Artificial
<220> FEATURE:
<223> OTHER INFORMATION: synthetic polypeptide

<400> SEQUENCE: 78

Leu Leu Arg Ser Ser Gln Asp Lys Gly Ser Ser Gln Asp Asn Cys Asn
  1               5                  10                  15

Asn Gln His Lys Gly Lys Lys Asp Ser Asn Gln Asp Lys Val Asn Ser
                 20                  25                  30

Gln Gly Lys Gly Asn Lys Val Ser Ser Gln Asp Lys Gly Asn Lys Val
                 35                  40                  45

Ser Asn Arg Gly Lys Gly Ser Gln Gly Thr Thr Gln Leu Leu Arg Ser
 50                  55                  60

Asn Gln Asp Lys Gly Asn Ser Gln Asp Asn Gly Asn Asn Gln Asp Lys
 65                  70                  75                  80

Gly Asn Gln Asp Thr Thr Gln Leu Leu Arg Cys Ser Gln Asp Lys Gly
                     85                  90                  95

Asn Gln Gly Thr Thr Gln Leu Leu Arg Asn Ser Gln Asp Lys Gly Ser
                100                 105                 110

Asn Gln Asp Asn Cys Asn Asn Gln His Lys Gly Asn Lys Gly Ser Asn
                115                 120                 125

<210> SEQ ID NO 79
<211> LENGTH: 35
<212> TYPE: PRT
<213> ORGANISM: Artificial
<220> FEATURE:
<223> OTHER INFORMATION: synthetic polypeptide

<400> SEQUENCE: 79

His Lys Gly Asn Lys Gly Ser Asn Gln His Lys Cys Asn Lys Gly Ser
  1               5                  10                  15

Gly Gln His Lys Gly Asn Lys Val Ser Ser Gln Asp Lys Gly Asn Lys
                 20                  25                  30
```

Val Ser Ser
        35

<210> SEQ ID NO 80
<211> LENGTH: 86
<212> TYPE: PRT
<213> ORGANISM: Artificial
<220> FEATURE:
<223> OTHER INFORMATION: synthetic polypeptide

<400> SEQUENCE: 80

Asp Lys Gly Asn Lys Val Ser Ser Gln Asp Lys Gly Asn Lys Gly Ser
1               5                   10                  15

Asn Gln His Lys Gly Asn Lys Val Ser Ser Gln Asp Lys Gly Asn Lys
            20                  25                  30

Val Ser Ser Gln Asp Lys Gly Asn Lys Val Ser Ser Gln Asp Lys Gly
        35                  40                  45

Ser Asn Arg Asp Lys Gly Ser His Gly Thr Thr Gln Leu Leu Arg Arg
    50                  55                  60

Ser Gln Asp Lys Gly Asn Ser Gln Asp Asn Gly Asn Asn Gln Asp Lys
65                  70                  75                  80

Gly Asn Gln Gly Thr Thr
            85

<210> SEQ ID NO 81
<211> LENGTH: 5
<212> TYPE: PRT
<213> ORGANISM: Artificial
<220> FEATURE:
<223> OTHER INFORMATION: synthetic polypeptide

<400> SEQUENCE: 81

Leu Leu Arg Cys Ser
1               5

<210> SEQ ID NO 82
<211> LENGTH: 74
<212> TYPE: PRT
<213> ORGANISM: Artificial
<220> FEATURE:
<223> OTHER INFORMATION: synthetic polypeptide

<400> SEQUENCE: 82

Asp Lys Gly Asn Lys Gly Thr Thr Gln Leu Leu Cys Asn Asn Gln Asp
1               5                   10                  15

Lys Gly Ser Asn Gln Asp Asn Gly Asn Asn Arg Asp Lys Gly Asn Ile
            20                  25                  30

Gly Thr Thr Gln Leu Leu Arg Ser Cys Gln Asp Lys Gly Asn Gly Gln
            35                  40                  45

Asp Asn Gly Cys Asn Gln Asp Lys Gly Asn Lys Gly Thr Thr Gln Leu
    50                  55                  60

Leu Arg Asn Ser Gln Asp Lys Gly Asn Asn
65                  70

<210> SEQ ID NO 83
<211> LENGTH: 48
<212> TYPE: PRT
<213> ORGANISM: Artificial
<220> FEATURE:
<223> OTHER INFORMATION: synthetic polypeptide

<400> SEQUENCE: 83

```
Asp Asn Gly Cys Asn Gln Asp Lys Gly Asn Lys Gly Thr Thr Gln Leu
1               5                   10                  15

Leu Cys Asn Arg Gln Asp Lys Gly Ser Asn Gln Asp Lys Gly Asn Lys
            20                  25                  30

Ala Thr Thr Ala His Thr Met Leu Ala Trp Ser Thr Arg Arg Pro Ala
        35                  40                  45

<210> SEQ ID NO 84
<211> LENGTH: 28
<212> TYPE: PRT
<213> ORGANISM: Artificial
<220> FEATURE:
<223> OTHER INFORMATION: synthetic polypeptide

<400> SEQUENCE: 84

Arg Trp Gln Arg Arg Ser Ser Ser Arg His Ser Cys Arg Gln Cys Ala
1               5                   10                  15

Gly Trp Arg Ala Ala Thr His Cys Arg Pro Ala Ser
            20                  25

<210> SEQ ID NO 85
<211> LENGTH: 18
<212> TYPE: PRT
<213> ORGANISM: Artificial
<220> FEATURE:
<223> OTHER INFORMATION: synthetic polypeptide

<400> SEQUENCE: 85

Ala Val Ser Pro Leu Cys Gly Gly Ser Arg Arg Pro Arg Gly Ser His
1               5                   10                  15

Arg Arg

<210> SEQ ID NO 86
<211> LENGTH: 4
<212> TYPE: PRT
<213> ORGANISM: Artificial
<220> FEATURE:
<223> OTHER INFORMATION: synthetic polypeptide

<400> SEQUENCE: 86

Ala Thr Thr Val
1

<210> SEQ ID NO 87
<211> LENGTH: 25
<212> TYPE: PRT
<213> ORGANISM: Artificial
<220> FEATURE:
<223> OTHER INFORMATION: synthetic polypeptide

<400> SEQUENCE: 87

Ala Arg Ala Pro Gly Ala Pro Gly Ala Arg Ala Gln Gly Met Pro Ala
1               5                   10                  15

Gly His Gly Pro Thr Ala Pro Arg His
            20                  25

<210> SEQ ID NO 88
<211> LENGTH: 753
<212> TYPE: PRT
<213> ORGANISM: Artificial
<220> FEATURE:
<223> OTHER INFORMATION: synthetic polypeptide

<400> SEQUENCE: 88
```

```
Pro Arg Val Pro Pro Arg Arg Gln Pro Gly Arg Gly Thr Ile Arg
1               5                   10                  15

Ala Ala Asn Arg Gly Ala Ala Gln Gly Arg Ile Phe Leu Pro Arg Arg
            20                  25                  30

Asp His Ala Thr Ala Ala Thr Pro Thr Thr Tyr Ile Leu Gly Asn Thr
        35                  40                  45

Cys Thr Thr Lys Lys Val Leu Pro Lys Cys Asn Leu Ser Ala Ala Gly
        50                  55                  60

Phe Ile Leu Ser Arg Pro Ser Phe Ser Ala Thr Ala Arg Thr Arg Ser
65                  70                  75                  80

Ala Ala Arg Thr Arg Thr Thr Arg Val Leu Pro Asn Phe Ser Ala Thr
            85                  90                  95

Ala Arg Thr Met Ala Thr Thr Gly Thr Arg Ala Thr Lys Val Leu Pro
            100                 105                 110

Asn Phe Ser Ala Ala Val Arg Thr Ile Ala Thr Thr Ser Thr Arg Ala
            115                 120                 125

Ala Thr Arg Thr Arg Ala Thr Arg Ser Ala Ala Arg Thr Arg Ala Thr
            130                 135                 140

Arg Val Leu Pro Asn Phe Phe Ala Ala Ala Ala Arg Thr Ile Ala Thr
145                 150                 155                 160

Thr Ser Thr Arg Ala Thr Arg Ala Ala Thr Arg Thr Ser Ala Thr Arg
            165                 170                 175

Ser Thr Ala Arg Thr Arg Ala Thr Thr Arg Thr Arg Thr Thr Arg Ser
            180                 185                 190

Thr Ala Arg Thr Arg Ala Thr Thr Arg Thr Arg Ala Thr Arg Ser Ala
            195                 200                 205

Ala Arg Thr Arg Thr Thr Arg Val Leu Pro Asn Phe Ser Ala Thr Val
            210                 215                 220

Gly Thr Arg Ala Thr Arg Val Leu Pro Asn Phe Ser Ala Ala Ala Arg
225                 230                 235                 240

Thr Arg Ala Ile Arg Val Leu Pro Asn Phe Ser Ala Ala Thr Arg Thr
            245                 250                 255

Arg Ala Ala Ala Arg Thr Ile Ala Thr Thr Ser Thr Arg Ala Ala Thr
            260                 265                 270

Arg Thr Arg Ala Thr Arg Ser Ala Ala Arg Thr Arg Ala Thr Arg Pro
            275                 280                 285

Ala Ala Arg Thr Arg Ala Ala Thr Gly Thr Arg Ala Thr Arg Val Leu
            290                 295                 300

Pro Asn Phe Ser Ala Ala Val Arg Thr Arg Ala Thr Arg Val Leu Pro
305                 310                 315                 320

Asn Phe Phe Ala Ala Ala Asn Thr Ile Ala Ala Thr Arg Thr Arg Ala
            325                 330                 335

Thr Arg Ser Ala Gly Arg Thr Arg Ala Thr Ser Ser Ala Ala Arg Thr
            340                 345                 350

Arg Ala Ala Thr Gly Thr Arg Ala Arg Val Leu Pro Asn Phe Ser
            355                 360                 365

Ala Ala Val Arg Thr Arg Ala Thr Arg Val Leu Pro Asn Phe Ser Ala
            370                 375                 380

Ala Val Arg Thr Arg Ala Ala Arg Thr Ile Ala Thr Ile Ser Thr
385                 390                 395                 400

Arg Ala Lys Arg Thr Ala Thr Arg Thr Arg Ser Thr Ala Arg Ala Arg
            405                 410                 415
```

Ala Thr Arg Ser Ala Ala Arg Thr Arg Ala Thr Ser Ala Thr Gly
            420                 425                 430

Ala Arg Ala Ala Arg Val Leu Pro Asn Phe Ser Ala Ala Ile Arg Thr
        435                 440                 445

Arg Ala Thr Ala Arg Thr Met Ala Thr Thr Arg Thr Arg Ala Thr Arg
450                 455                 460

Ile Leu Pro Asn Phe Ser Val Ala Ala Arg Thr Arg Ala Thr Arg Val
465                 470                 475                 480

Arg Pro Asn Phe Ser Ala Thr Ala Arg Thr Arg Ala Ala Thr Arg Thr
                485                 490                 495

Ile Ala Thr Thr Ser Thr Arg Ala Thr Arg Ala Ala Thr Ser Thr Arg
            500                 505                 510

Ala Thr Arg Ala Ala Thr Ser Thr Ser Ala Thr Arg Ala Ala Ala Ser
        515                 520                 525

Thr Arg Ala Thr Arg Ser Ala Ala Arg Thr Arg Ala Thr Arg Ser Ala
    530                 535                 540

Ala Arg Thr Arg Ala Thr Arg Ser Ala Ala Arg Thr Arg Ala Thr Arg
545                 550                 555                 560

Ala Ala Thr Ser Thr Arg Ala Thr Arg Ser Ala Ala Arg Thr Arg Ala
                565                 570                 575

Thr Arg Ser Ala Ala Arg Thr Arg Ala Thr Arg Ser Ala Ala Arg Thr
            580                 585                 590

Arg Ala Ala Thr Gly Thr Arg Ala Ala Met Val Leu Pro Asn Phe Ser
        595                 600                 605

Ala Gly Val Arg Thr Arg Ala Thr Ala Arg Thr Met Ala Thr Thr Arg
610                 615                 620

Thr Arg Ala Thr Arg Val Leu Pro Asn Phe Ser Val Ala Ala Arg Thr
625                 630                 635                 640

Arg Ala Thr Arg Val Leu Pro Asn Phe Ser Ala Thr Arg Thr Arg
                645                 650                 655

Ala Ala Thr Arg Thr Met Ala Thr Ile Gly Thr Arg Ala Thr Leu Val
            660                 665                 670

Leu Pro Asn Phe Ser Ala Ala Val Arg Thr Arg Ala Thr Ala Arg Thr
        675                 680                 685

Met Ala Ala Thr Arg Thr Arg Ala Thr Arg Val Leu Pro Asn Phe Ser
    690                 695                 700

Ala Thr Ala Arg Thr Arg Ala Thr Thr Arg Thr Met Ala Ala Thr Arg
705                 710                 715                 720

Thr Arg Ala Thr Arg Val Leu Pro Asn Phe Ser Ala Thr Asp Arg Thr
                725                 730                 735

Arg Ala Ala Ile Arg Thr Arg Ala Thr Arg Leu Leu Gln Leu Ile Pro
            740                 745                 750

Cys

<210> SEQ ID NO 89
<211> LENGTH: 37
<212> TYPE: PRT
<213> ORGANISM: Artificial
<220> FEATURE:
<223> OTHER INFORMATION: synthetic polypeptide

<400> SEQUENCE: 89

Arg Gly Ala Pro Gly Gly Gln Pro Lys Gly Gly Lys Gly Ala Ala Ala
1               5                   10                  15

Arg Gly Thr Ala Ala Gly Asn Val Pro Ala Gly Gly Arg Arg Arg Ile

Val Gly Gln Pro Val
        35

<210> SEQ ID NO 90
<211> LENGTH: 848
<212> TYPE: PRT
<213> ORGANISM: Triticum aestivum

<400> SEQUENCE: 90

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
            20                  25                  30

Arg Glu Leu Gln Glu Leu Gln Glu Arg Glu Leu Lys Ala Cys Gln Gln
            35                  40                  45

Val Met Asp Gln Gln Leu Arg Asp Ile Ser Pro Glu Cys His Pro Val
50                  55                  60

Val Val Ser Pro Val Ala Gly Gln Tyr Glu Gln Gln Ile Val Val Pro
65                  70                  75                  80

Pro Lys Gly Gly Ser Phe Tyr Pro Gly Glu Thr Thr Pro Pro Gln Gln
                85                  90                  95

Leu Gln Gln Arg Ile Phe Trp Gly Ile Pro Ala Leu Leu Lys Arg Tyr
            100                 105                 110

Tyr Pro Ser Val Thr Cys Pro Gln Gln Val Ser Tyr Tyr Pro Gly Gln
            115                 120                 125

Ala Ser Pro Gln Arg Pro Gly Gln Gly Gln Gln Pro Gly Gln Gly Gln
        130                 135                 140

Gln Gly Tyr Tyr Pro Thr Ser Pro Gln Gln Pro Gly Gln Trp Gln Gln
145                 150                 155                 160

Pro Glu Gln Gly Gln Pro Arg Tyr Tyr Pro Thr Ser Pro Gln Gln Ser
                165                 170                 175

Gly Gln Leu Gln Gln Pro Ala Gln Gly Gln Gln Pro Gly Gln Gly Gln
            180                 185                 190

Gln Gly Gln Gln Pro Gly Gln Gly Gln Pro Gly Tyr Tyr Pro Thr Ser
        195                 200                 205

Ser Gln Leu Gln Pro Gly Gln Leu Gln Pro Ala Gln Gly Gln Gln
        210                 215                 220

Gly Gln Gln Pro Gly Gln Ala Gln Gly Gln Gln Pro Gly Gln Gly
225                 230                 235                 240

Gln Gln Pro Gly Gln Gly Gln Gly Gln Gln Pro Gly Gln Gly Gln
                245                 250                 255

Gln Pro Gly Gln Gly Gln Gly Gln Gln Leu Gly Gln Gly Gln Gln
            260                 265                 270

Gly Tyr Tyr Pro Thr Ser Leu Gln Gln Ser Gly Gln Gly Gln Pro Gly
            275                 280                 285

Tyr Tyr Pro Thr Ser Leu Gln Gln Leu Gly Gln Gly Gln Ser Gly Tyr
        290                 295                 300

Tyr Pro Thr Ser Pro Gln Gln Pro Gly Gln Gln Pro Gly Gln
305                 310                 315                 320

Leu Gln Gln Pro Ala Gln Gly Gln Pro Gly Gln Gly Gln Gly
                325                 330                 335

Gln Gln Pro Gly Gln Gly Gln Gly Gln Gln Pro Gly Gln Gly Gln
            340                 345                 350

```
Gln Pro Gly Gln Gly Gln Pro Gly Tyr Tyr Pro Thr Ser Pro Gln Gln
            355                 360                 365

Ser Gly Gln Gly Gln Pro Gly Tyr Tyr Pro Thr Ser Ser Gln Gln Pro
        370                 375                 380

Thr Gln Ser Gln Gln Pro Gly Gln Gly Gln Gln Gly Gln Gln Val Gly
385                 390                 395                 400

Gln Gly Gln Gln Ala Gln Pro Gly Gln Gly Gln Pro Gly Gln
                405                 410                 415

Gly Gln Pro Gly Tyr Tyr Pro Thr Ser Pro Gln Gln Ser Gly Gln Gly
            420                 425                 430

Gln Pro Gly Tyr Tyr Leu Thr Ser Pro Gln Gln Ser Gly Gln Gly Gln
            435                 440                 445

Gln Pro Gly Gln Leu Gln Gln Ser Ala Gln Gly Gln Lys Gly Gln Gln
        450                 455                 460

Pro Gly Gln Gly Gln Pro Gly Gln Gly Gln Gln Gly Gln Gln Pro
465                 470                 475                 480

Gly Gln Gly Gln Gln Gly Gln Gln Pro Gly Gln Gly Gln Pro Gly Tyr
                485                 490                 495

Tyr Pro Thr Ser Pro Gln Gln Ser Gly Gln Gly Gln Gln Pro Gly Gln
            500                 505                 510

Trp Gln Gln Pro Gly Gln Gly Gln Pro Gly Tyr Tyr Pro Thr Ser Pro
        515                 520                 525

Leu Gln Pro Gly Gln Gly Gln Pro Gly Tyr Asp Pro Thr Ser Pro Gln
        530                 535                 540

Gln Pro Gly Gln Gly Gln Pro Gly Gln Leu Gln Gln Pro Ala Gln Gln
545                 550                 555                 560

Gly Gln Gln Gly Gln Gln Leu Ala Gln Gly Gln Gln Gly Gln Gln Pro
                565                 570                 575

Ala Gln Val Gln Gln Gly Gln Arg Pro Ala Gln Gly Gln Gln Gly Gln
            580                 585                 590

Gln Pro Gly Gln Gly Gln Gly Gln Gln Leu Gly Gln Gln Gln Gln
        595                 600                 605

Gly Gln Gln Pro Gly Gln Gly Gln Gly Gln Gln Pro Ala Gln Gly
610                 615                 620

Gln Gln Gly Gln Gln Pro Gly Gln Gly Gln Gly Gln Gln Pro Gly
625                 630                 635                 640

Gln Gly Gln Gln Gly Gln Gln Pro Gly Gln Gly Gln Gln Pro Gly Gln
                645                 650                 655

Gly Gln Pro Trp Tyr Tyr Pro Thr Ser Pro Gln Glu Ser Gly Gln Gly
            660                 665                 670

Gln Gln Pro Gly Gln Trp Gln Gln Pro Gly Gly Gln Pro Gly Tyr
        675                 680                 685

Tyr Leu Thr Ser Pro Leu Gln Leu Gly Gln Gly Gln Gln Tyr Tyr
690                 695                 700

Pro Thr Ser Leu Gln Gln Pro Gly Gln Gly Gln Pro Gly Gln Trp
705                 710                 715                 720

Gln Gln Ser Gly Gln Gly Gln His Trp Tyr Tyr Pro Thr Ser Pro Gln
                725                 730                 735

Leu Ser Gly Gln Gly Gln Arg Pro Gln Gly Gln Trp Leu Gln Pro Gly Gln
            740                 745                 750

Gly Gln Gln Gly Tyr Tyr Pro Thr Ser Pro Gln Gln Pro Gly Gln Gly
            755                 760                 765

Gln Gln Leu Gly Gln Trp Leu Gln Pro Gly Gln Gly Gln Gln Gly Tyr
```

-continued

```
                770                 775                 780
Tyr Pro Thr Ser Leu Gln Gln Thr Gly Gln Gly Gln Gln Ser Gly Gln
785                 790                 795                 800

Gly Gln Gln Gly Tyr Tyr Ser Ser Tyr His Val Ser Val Glu His Gln
                805                 810                 815

Ala Ala Ser Leu Lys Val Ala Lys Ala Gln Gln Leu Ala Ala Gln Leu
            820                 825                 830

Pro Ala Met Cys Arg Leu Glu Gly Gly Asp Ala Leu Ser Ala Ser Gln
            835                 840                 845

<210> SEQ ID NO 91
<211> LENGTH: 810
<212> TYPE: PRT
<213> ORGANISM: Artificial
<220> FEATURE:
<223> OTHER INFORMATION: synthetic polypeptide

<400> SEQUENCE: 91

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
                20                  25                  30

Arg Glu Leu Gln Glu Leu Gln Glu Arg Glu Leu Lys Ala Cys Gln Gln
            35                  40                  45

Val Met Asp Gln Gln Leu Arg Asp Ile Pro Arg Val Pro Arg Arg
    50                  55                  60

Arg Gln Pro Gly Arg Gly Thr Ile Arg Ala Ala Asn Arg Gly Ala Ala
65                  70                  75                  80

Gln Gly Arg Ile Phe Leu Pro Arg Arg Asp His Ala Thr Ala Ala Thr
                85                  90                  95

Pro Thr Thr Tyr Ile Leu Gly Asn Thr Cys Thr Thr Lys Lys Val Leu
            100                 105                 110

Pro Lys Cys Asn Leu Ser Ala Ala Gly Phe Ile Leu Ser Arg Pro Ser
        115                 120                 125

Phe Ser Ala Thr Ala Arg Thr Arg Ser Ala Ala Arg Thr Arg Thr Thr
130                 135                 140

Arg Val Leu Pro Asn Phe Ser Ala Thr Ala Arg Thr Met Ala Thr Thr
145                 150                 155                 160

Gly Thr Arg Ala Thr Lys Val Leu Pro Asn Phe Ser Ala Ala Val Arg
                165                 170                 175

Thr Ile Ala Thr Thr Ser Thr Arg Ala Ala Thr Arg Thr Arg Ala Thr
            180                 185                 190

Arg Ser Ala Ala Arg Thr Arg Ala Thr Arg Val Leu Pro Asn Phe Phe
        195                 200                 205

Ala Ala Ala Arg Thr Ile Ala Thr Thr Ser Thr Arg Ala Thr Arg
    210                 215                 220

Ala Ala Thr Arg Thr Ser Ala Thr Arg Ser Ala Arg Thr Arg Ala
225                 230                 235                 240

Thr Thr Arg Thr Arg Thr Thr Arg Ser Thr Ala Arg Thr Arg Ala Thr
                245                 250                 255

Thr Arg Thr Arg Ala Thr Arg Ser Ala Ala Arg Thr Arg Thr Thr Arg
            260                 265                 270

Val Leu Pro Asn Phe Ser Ala Thr Val Gly Thr Arg Ala Thr Arg Val
        275                 280                 285

Leu Pro Asn Phe Ser Ala Ala Ala Arg Thr Arg Ala Ile Arg Val Leu
```

```
            290                 295                 300
Pro Asn Phe Ser Ala Ala Thr Arg Thr Arg Ala Ala Arg Thr Ile
305                 310                 315                 320

Ala Thr Thr Ser Thr Arg Ala Ala Thr Arg Thr Arg Ala Thr Arg Ser
                325                 330                 335

Ala Ala Arg Thr Arg Ala Thr Arg Pro Ala Ala Arg Thr Arg Ala Ala
                340                 345                 350

Thr Gly Thr Arg Ala Thr Arg Val Leu Pro Asn Phe Ser Ala Ala Val
        355                 360                 365

Arg Thr Arg Ala Thr Arg Val Leu Pro Asn Phe Phe Ala Ala Ala Asn
370                 375                 380

Thr Ile Ala Ala Thr Arg Thr Arg Ala Thr Arg Ser Ala Gly Arg Thr
385                 390                 395                 400

Arg Ala Thr Ser Ser Ala Ala Arg Thr Arg Ala Ala Thr Gly Thr Arg
                405                 410                 415

Ala Ala Arg Val Leu Pro Asn Phe Ser Ala Ala Val Arg Thr Arg Ala
                420                 425                 430

Thr Arg Val Leu Pro Asn Phe Ser Ala Ala Val Arg Thr Arg Ala Ala
                435                 440                 445

Ala Arg Thr Ile Ala Thr Ile Ser Thr Arg Ala Lys Arg Thr Ala Thr
        450                 455                 460

Arg Thr Arg Ser Thr Ala Arg Ala Arg Ala Thr Arg Ser Ala Ala Arg
465                 470                 475                 480

Thr Arg Ala Thr Arg Ser Ala Thr Gly Ala Arg Ala Ala Arg Val Leu
                485                 490                 495

Pro Asn Phe Ser Ala Ala Ile Arg Thr Arg Ala Thr Ala Arg Thr Met
                500                 505                 510

Ala Thr Thr Arg Thr Arg Ala Thr Arg Ile Leu Pro Asn Phe Ser Val
        515                 520                 525

Ala Ala Arg Thr Arg Ala Thr Arg Val Arg Pro Asn Phe Ser Ala Thr
        530                 535                 540

Ala Arg Thr Arg Ala Ala Thr Arg Thr Ile Ala Thr Thr Ser Thr Arg
545                 550                 555                 560

Ala Thr Arg Ala Ala Thr Ser Thr Arg Ala Thr Arg Ala Ala Thr Ser
                565                 570                 575

Thr Ser Ala Thr Arg Ala Ala Ser Thr Arg Ala Thr Arg Ser Ala
        580                 585                 590

Ala Arg Thr Arg Ala Thr Arg Ser Ala Ala Arg Thr Arg Ala Thr Arg
        595                 600                 605

Ser Ala Ala Arg Thr Arg Ala Thr Arg Ala Ala Thr Ser Thr Arg Ala
        610                 615                 620

Thr Arg Ser Ala Ala Arg Thr Arg Ala Thr Ser Ala Ala Arg Thr
625                 630                 635                 640

Arg Ala Thr Arg Ser Ala Ala Arg Thr Arg Ala Ala Thr Gly Thr Arg
                645                 650                 655

Ala Ala Met Val Leu Pro Asn Phe Ser Ala Gly Val Arg Thr Arg Ala
        660                 665                 670

Thr Ala Arg Thr Met Ala Thr Thr Arg Thr Arg Ala Thr Arg Val Leu
        675                 680                 685

Pro Asn Phe Ser Val Ala Ala Arg Thr Arg Ala Thr Arg Val Leu Pro
        690                 695                 700

Asn Phe Ser Ala Thr Thr Arg Thr Arg Ala Ala Thr Arg Thr Met Ala
705                 710                 715                 720
```

```
Thr Ile Gly Thr Arg Ala Thr Leu Val Leu Pro Asn Phe Ser Ala Ala
                725                 730                 735

Val Arg Thr Arg Ala Thr Ala Arg Thr Met Ala Ala Thr Arg Thr Arg
                740                 745                 750

Ala Thr Arg Val Leu Pro Asn Phe Ser Ala Thr Ala Arg Thr Arg Ala
                755                 760                 765

Thr Thr Arg Thr Met Ala Ala Thr Arg Thr Ala Thr Arg Val Leu
770                 775                 780

Pro Asn Phe Ser Ala Thr Asp Arg Thr Arg Ala Ala Ile Arg Thr Arg
785                 790                 795                 800

Ala Thr Arg Leu Leu Gln Leu Ile Pro Cys
                805                 810

<210> SEQ ID NO 92
<211> LENGTH: 296
<212> TYPE: PRT
<213> ORGANISM: Artificial
<220> FEATURE:
<223> OTHER INFORMATION: synthetic polypeptide

<400> SEQUENCE: 92

Met Ala Lys Arg Leu Val Leu Phe Val Ala Val Val Ala Leu Val
1               5                   10                  15

Ala Leu Thr Val Ala Glu Gly Glu Ala Ser Glu Gln Leu Gln Cys Glu
                20                  25                  30

Arg Glu Leu Gln Glu Leu Gln Glu Arg Glu Leu Lys Ala Cys Gln Gln
                35                  40                  45

Val Met Asp Gln Gln Leu Arg Asp Ile Ser Pro Glu Cys His Pro Val
50                  55                  60

Val Val Ser Pro Val Ala Gly Gln Tyr Glu Gln Ile Val Val Pro
65                  70                  75                  80

Pro Lys Gly Gly Ser Phe Tyr Pro Gly Glu Thr Thr Pro Pro Gln Gln
                85                  90                  95

Leu Gln Gln Arg Ile Phe Trp Gly Ile Pro Ala Leu Leu Lys Arg Tyr
                100                 105                 110

Tyr Pro Ser Val Leu Val Arg Ser Arg Phe His Thr Ile Gln Ala Lys
                115                 120                 125

Leu Leu Arg Asn Gly Gln Asp Lys Val Ser Ser Gln Asp Lys Asp Asn
                130                 135                 140

Lys Gly Thr Thr Gln Leu Leu Arg Asn Ser Gln Asp Asn Gly Asn Asn
145                 150                 155                 160

Arg Asn Lys Gly Asn Gln Gly Thr Thr Gln Leu Leu Arg Ser Ser Gln
                165                 170                 175

Asp Asn Cys Asn Asn Gln His Lys Gly Ser Asn Gln Asp Lys Gly Asn
                180                 185                 190

Lys Val Ser Ser Gln Asp Lys Gly Asn Gln Gly Thr Thr Gln Leu Leu
                195                 200                 205

Arg Ser Cys Ser Gln Asp Asn Cys Asn Asn Gln His Lys Gly Asn Lys
                210                 215                 220

Gly Ser Asn Gln Asp Lys Arg Asn Lys Val Asn Ser Gln Asp Lys Gly
225                 230                 235                 240

Asn Asn Gln Asp Lys Asp Asn Lys Val Asn Ser Gln Asp Lys Gly Asn
                245                 250                 255

Asn Gln Asp Lys Gly Asn Lys Val Ser Ser Ser Asp Lys Asp Asn Lys
                260                 265                 270
```

```
Gly Thr Thr Gln Leu Leu Cys Asn Ser Arg Asp Lys Gly Asn Gln Gly
        275                 280                 285

Thr Thr Gln Leu Leu Cys Ser Ser
    290                 295

<210> SEQ ID NO 93
<211> LENGTH: 9
<212> TYPE: PRT
<213> ORGANISM: Artificial
<220> FEATURE:
<223> OTHER INFORMATION: consensus

<400> SEQUENCE: 93

Leu Ala Gly Leu Ile Asp Ala Asp Gly
1               5

<210> SEQ ID NO 94
<211> LENGTH: 50
<212> TYPE: DNA
<213> ORGANISM: Glycine max

<400> SEQUENCE: 94
tcgtgacagt ggaaggaggt ctcagcgtta tcagccccaa gtggcaagaa            50

<210> SEQ ID NO 95
<211> LENGTH: 106
<212> TYPE: PRT
<213> ORGANISM: Artificial
<220> FEATURE:
<223> OTHER INFORMATION: synthetic polypeptide

<400> SEQUENCE: 95

Met Lys Met Lys Met Lys Thr Lys Met Met Lys Met Asn Lys Phe Pro
1               5                   10                  15

Leu Thr Leu Leu Ala Asp Gln Ala Met Glu Ser Val Asn Lys Thr Arg
            20                  25                  30

Thr Arg Thr Lys Met Lys Ile Asn Leu Val Leu Val Asp Gln Ala Lys
        35                  40                  45

Glu Ser Val Asn Lys Thr Arg Thr Arg Thr Lys Met Lys Met
    50                  55                  60

Lys Ile Asn Leu Ala Arg Lys Ser Arg Glu Trp Arg Ser Lys Lys Thr
65                  70                  75                  80

Gln Pro Arg Arg Pro Arg Gln Glu Glu Pro Arg Glu Arg Gly Cys Glu
                85                  90                  95

Thr Arg Asn Gly Val Glu Glu Asn Ile Cys
            100                 105

<210> SEQ ID NO 96
<211> LENGTH: 57
<212> TYPE: DNA
<213> ORGANISM: Triticum aestivum

<400> SEQUENCE: 96
atgaagacct ttctcatcct tgccctccgt gctattgtag caaccaccgc cacaatt    57

<210> SEQ ID NO 97
<211> LENGTH: 14
<212> TYPE: PRT
<213> ORGANISM: Artificial
<220> FEATURE:
<223> OTHER INFORMATION: synthetic polypeptide
```

```
<400> SEQUENCE: 97

Thr Gly Pro Gly Leu Cys Pro Ala Ser Thr Thr Ala Pro Val
1               5                   10

<210> SEQ ID NO 98
<211> LENGTH: 21
<212> TYPE: PRT
<213> ORGANISM: Artificial
<220> FEATURE:
<223> OTHER INFORMATION: synthetic polypeptide

<400> SEQUENCE: 98

Thr Asp Arg Thr Arg Ala Ala Ile Arg Thr Arg Ala Thr Arg Leu Leu
1               5                   10                  15

Gln Leu Ile Pro Cys
            20

<210> SEQ ID NO 99
<211> LENGTH: 20
<212> TYPE: PRT
<213> ORGANISM: Artificial
<220> FEATURE:
<223> OTHER INFORMATION: synthetic polypeptide

<400> SEQUENCE: 99

Leu Leu Cys Asn Ser Arg Asp Lys Gly Asn Gln Gly Thr Thr Gln Leu
1               5                   10                  15

Leu Cys Ser Ser
            20
```